US009458467B2

(12) United States Patent
Steidler et al.

(10) Patent No.: US 9,458,467 B2
(45) Date of Patent: *Oct. 4, 2016

(54) MODIFIED GRAM POSITIVE BACTERIA AND USES THEREOF

(71) Applicant: INTREXON ACTOBIOTICS NV, Zwijnaarde (BE)

(72) Inventors: Lothar Steidler, Lokeren (BE); Karolien Van Huynegem, Asper (BE); Klaas Vandenbroucke, De Pinte (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/346,504

(22) PCT Filed: Sep. 21, 2012

(86) PCT No.: PCT/EP2012/068633
§ 371 (c)(1),
(2) Date: Mar. 21, 2014

(87) PCT Pub. No.: WO2013/041672
PCT Pub. Date: Mar. 28, 2013

(65) Prior Publication Data
US 2014/0234371 A1 Aug. 21, 2014

(30) Foreign Application Priority Data
Sep. 23, 2011 (EP) .................................... 11182642

(51) Int. Cl.
| | | |
|---|---|---|
| *A61K 39/02* | (2006.01) |
| *A01N 63/02* | (2006.01) |
| *A01N 63/00* | (2006.01) |
| *C12N 1/20* | (2006.01) |
| *C12N 1/00* | (2006.01) |
| *C12N 15/74* | (2006.01) |
| *C12N 1/04* | (2006.01) |
| *C12N 9/10* | (2006.01) |
| *A23L 1/30* | (2006.01) |
| *A61K 38/00* | (2006.01) |
| *A61K 39/00* | (2006.01) |
| *C07K 14/325* | (2006.01) |
| *C12N 15/86* | (2006.01) |
| *A61K 35/744* | (2015.01) |

(52) U.S. Cl.
CPC ........... *C12N 15/746* (2013.01); *A23L 1/3014* (2013.01); *C12N 1/04* (2013.01); *C12N 9/1051* (2013.01); *A61K 35/744* (2013.01); *A61K 38/00* (2013.01); *A61K 2039/522* (2013.01); *C07K 14/325* (2013.01); *C12N 1/20* (2013.01); *C12N 15/86* (2013.01)

(58) Field of Classification Search
CPC ........... A61K 2039/522; A61K 38/00; C07K 14/325; C12N 15/86; C12N 1/20
See application file for complete search history.

(56) References Cited

U.S. PATENT DOCUMENTS

| 5,559,007 A | 9/1996 | Suri et al. |
|---|---|---|
| 6,790,444 B2 | 9/2004 | Le et al. |
| 2014/0227229 A1 | 8/2014 | Steidler et al. |

FOREIGN PATENT DOCUMENTS

| CN | 1922305 A | 2/2007 |
|---|---|---|
| EP | 1 116 849 A2 | 7/2001 |
| EP | 1 117 358 A1 | 7/2001 |
| WO | WO-96/11277 A1 | 4/1996 |
| WO | WO-97/14806 A2 | 4/1997 |
| WO | WO 00/18340 A1 | 4/2000 |
| WO | WO-00/18340 A1 | 4/2000 |
| WO | WO-00/23471 A2 | 4/2000 |
| WO | WO-01/02570 A1 | 1/2001 |
| WO | WO-01/94585 A1 | 12/2001 |
| WO | WO-02/090551 A2 | 11/2002 |
| WO | WO-2004/046346 A2 | 6/2004 |
| WO | WO 2005/080548 A1 | 9/2005 |
| WO | WO-2005/111194 A1 | 11/2005 |
| WO | WO 2006/018446 A2 | 2/2006 |
| WO | WO-2007/025977 A2 | 3/2007 |
| WO | WO-2007/063075 A1 | 6/2007 |
| WO | WO-2007/128757 A2 | 11/2007 |
| WO | WO-2008/071751 A1 | 6/2008 |
| WO | WO-2008/084115 A2 | 7/2008 |
| WO | WO 2008/090223 A2 * | 7/2008 |
| WO | WO-2010/034844 A1 | 4/2010 |
| WO | WO-2010/124855 A1 | 11/2010 |

OTHER PUBLICATIONS

Castro et al., "Characterization of the individual glucose uptake systems of *Lactococcus lactis*: mannose-PTS, cellobiose-PTS and the novel GlcU permease," Molecular Microbiology, vol. 71(3), pp. 795-806 (2009).

(Continued)

*Primary Examiner* — Gary Nickol
*Assistant Examiner* — Lakia Tongue
(74) *Attorney, Agent, or Firm* — Drinker Biddle & Reath LLP

(57) ABSTRACT

The present invention relates to a gram positive bacterium, preferably a lactic acid bacterium (LAB) or *Bifidobacterium*, with increased stress resistance and/or improved manufacturing, processing and/or storage characteristics. In particular, the invention relates to a gram positive bacterium which accumulate intracellular trehalose. The gram positive bacterium according to the invention lack trehalose 6-phosphate phosphorylase (TrePP) activity. The gram positive bacterium may further lack cellobiose-specific PTS system IIC component (ptcC) activity. The gram positive bacterium may further overexpress trehalose transporters. The invention further relates to compositions comprising such gram positive bacterium as well as methods and uses thereof.

25 Claims, 14 Drawing Sheets

(56) References Cited

OTHER PUBLICATIONS

Old et al., "Genomic variation in Streptococcus mutans: deletions affecting the multiple pathways of 1β-glucoside metabolism," Oral Microbiology Immunology, vol. 21, pp. 21-27 (2006).

Andersson et al., "Trehalose-6-phosphate Phosphorylase Is Part of a Novel Metabolic Pathway for Trehalose Utilization in *Lactococcus lactis*," *The Journal of Biological Chemistry*, vol. 276(46), pp. 42707-42713 (Nov. 16, 2001).

Carvalho et al., "Engineering Trehalose Synthesis in *Lactococcus lactis* for Improved Stress Tolerance," *Applied and Environmental Microbiology*, vol. 77(12), pp. 4189-4199 (Jun. 2011).

Duong et al., "Characterization of the tre Locus and Analysis of Trehalose Cryoprotection in *Lactobacillus acidophilus* NCFM," *Applied and Environmental Microbiology*, vol. 72(2), pp. 1218-1225 (Feb. 2006).

Termont et al., "Intracellular Accumulation of Trehalose Protects *Lactococcus lactis* from Freeze-Drying Damage and Bile Toxicity and Increases Gastric Acid Resistance," *Applied and Environmental Microbiology*, vol. 72(12), pp. 7694-7700 (Dec. 2006).

Tatusova et al., "BLAST 2 Sequences, a new tool for comparing protein and nucleotide sequences," FEMS Microbiology Letters, vol. 174, 1999, pp. 247-250.

Office Action dated Jun. 16, 2015 in U.S. Appl. No. 14/346,488 with a double patenting rejection at pp. 2-4.

\* cited by examiner

A

B

A

B

A

B

MODIFIED GRAM POSITIVE BACTERIA AND USES THEREOF

CROSS-REFERENCE TO RELATED APPLICATIONS

This application is the U.S. National Phase under 35 U.S.C. §371 of International Application PCT/EP2012/068633, filed Sep. 21, 2012, which claims priority to EP 11182642.6, filed Sep. 23, 2011.

REFERENCE TO SEQUENCE LISTING

This application incorporates by reference the sequence listing submitted as ASCII text filed via EFS-Web on Mar. 21, 2014. The Sequence Listing is provided as a file entitled "seqlst_decle132_009apc," created on Mar. 20, 2014, and which is approximately 33 kilobytes in size.

FIELD OF THE INVENTION

The present invention relates to microorganisms, such as gram positive bacteria, with improved stress resistance and improved manufacturing, processing and storage characteristics. The invention in particular relates to genetically modified microorganisms which accumulate intracellular trehalose. The invention further relates to uses of these microorganisms in food technology and medical applications.

BACKGROUND OF THE INVENTION

Gram-positive bacteria are collectively classified as having a single lipid bilayer plasma membrane. Gram positive bacteria include a multitude of bacilliform and cocciform bacterial genera, among which *Bifidobacteria* and a group of genera collectively known as lactic acid bacteria (LAB). LAB comprise a Glade of Gram-positive, low-GC, acid-tolerant, generally non-sporulating, non-respiring rod or cocci that are associated by their common metabolic and physiological characteristics. These bacteria, usually found in (decomposing) plants and dairy products, produce lactic acid as the major metabolic end-product of carbohydrate fermentation. This trait has, throughout history, linked LAB with food fermentations, as acidification inhibits the growth of spoilage agents. A prototype LAB *Lactococcus lactis* is a mesophilic and microaerophilic fermenting lactic acid bacterium. While the bacterium is extensively used in food fermentations, especially in the dairy industry, there is an increasing interest for its use in medicaments and nutraceuticals, as medication to treat infections in bodily cavities such as vaginal infections, or as carrier for the delivery of biological active molecules. In all those cases, there is a need for highly viable starter cultures, or pharmaceutical or nutraceutical formulations comprising a high proportion of viable bacteria. *L. lactis*, however, tends to lose viability during storage, or during processing (for a.o the production of a dry powder formula, tablet formation, . . . ). The drop in viability is even more pronounced when the bacterium after lyophilisation is submitted to additional stress such as high acidity or the presence of bile salts.

Several methods have been proposed to overcome this problem. The use of trehalose is of particular interest. Trehalose (α-D-glucopyranosyl-1,1-α-D-glucopyranoside) is a non-reducing disaccharide that occurs in a large variety of organisms, ranging from bacteria to invertebrate animals. Trehalose, sometimes in combination with dextran, is often used as and externally added cryopreservant. Externally added trehalose functions as a saccharide matrix (Conrad et al., 2000,), and exerts it protective effect especially during freeze drying, where it acts as a glass former. Moreover, trehalose is well recognized as stress metabolite, and it has been extensively studied in fungi, especially in *Saccharomyces cerevisiae*. High concentrations of internal trehalose do improve the storage capacity and result in a higher viability upon cryopreservation. However, it is important to note that externally added trehalose rarely leads to internal trehalose accumulation in micro-organisms, either because it is not taken up, or it is metabolized rapidly after uptake.

Termont et al. (Appl Environ Microbiol 72:7694; 2006) reported that de-novo synthesized trehalose, through plasmid driven overexpression of otsA (trehalose-6-phosphate synthase) and otsB (trehalose-6-phosphate phosphatase) accumulates intracellularly in *L. lactis*. Intracellular trehalose accumulation but not exogenously added trehalose protects *L. lactis* from bile lysis and cell death through freeze-drying. As *L. lactis* is extremely sensitive, protection to bile lysis can be used as a superb functional assay of intracellular trehalose accumulation.

Andersson et al. (J Biol Chem 276:42707; 2001) have described a novel pathway for trehalose utilization in *L. lactis*. This pathway employs the activity of trehalose-6-phosphate phosphorylase (trePP), converting trehalose-6-phosphate to β-glucose 1-phosphate and glucose 6-phosphate. They describe insertional inactivation of trePP in *L. lactis*, resulting in loss of capacity to grow on trehalose.

For the intracellular accumulation of trehalose, Carvalho et al. (Appl Environ Microbiol 77:4189; 2011) describe a method that makes use of plasmid driven overexpression of *L. lactis* trePP and β-phosphoglucomutase (pgmB). As indicated by these authors, given that the bacteria lack trehalose 6-phosphate phosphatase, the respective gene, otsB, from food-grade organism *P. freudenreichii* was used to provide the required activity. The resulting cells showed improved resistance to cold shock, heat shock and acidity.

Although these processes certainly lead to an improvement of the storage, there is a further need of methods that can lead to an improved storage of gram positive bacteria, such as LAB or *Bifidobacteria*, not only in those cases where the bacterium is used for the delivery of biological active compounds in medical applications, but also when the bacterium is used in the food industry, such as the dairy industry.

SUMMARY OF THE INVENTION

Intracellular trehalose can protect microorganisms such as lactic acid bacteria (LAB), for instance *Lactococcus lactis* cells, from various detrimental agents or conditions. Examples are bile acid lysis, experienced by live LAB during intestinal transit, or freezing and/or drying stress during freezing, drying, spray drying, lyophilization, as used for preservation of LAB.

Only a limited number of approaches are available that allow for the accumulation of trehalose inside the cell. These make use of plasmid driven overexpression of homologous or heterologous genes. This is however not a desirable configuration for use in pharmaceutical or food products.

Here we report a novel approach that allows for the intracellular accumulation of trehalose, based merely on the absence of trehalose 6-phosphate phosphorylase (TrePP) activity in gram positive bacteria, preferably through rendering the gene encoding endogenous TrePP partially or completely deleted, disrupted or inactivated such as being incapable of producing functional trePP gene product. In contrast to the present approach, previous works (WO 2006/018446) taught to express heterologous trehalose 6-phosphatase such as otsB to achieve trehalose accumulation. Carvalho et al. 2011 (supra) even instructed to overexpress TrePP to obtain intracellular trehalose accumulation. Moreover, although LAB such as *Lactococcus lactis* may be able to utilize trehalose, up to now no trehalose synthesizing *Lactococcus lactis* strain has been described. No endogenous trehalose-6-phosphate synthase and trehalose-6-phosphate phosphatase genes have been identified, which were believed to be a prerequisite for trehalose production starting from glucose-6-phosphate, a metabolite present in *L. lactis*.

In an aspect, the invention relates to a gram positive bacterium, preferably a lactic acid bacterium (LAB) or *Bifidobacterium*, lacking trehalose 6-phosphate phosphorylase (TrePP) activity for use as a medicament.

A further aspect provides a medicament comprising a gram positive bacterium, preferably a lactic acid bacterium (LAB) or *Bifidobacterium*, lacking TrePP activity. Such medicaments may for example encompass pharmaceutical formulations, nutraceuticals, medical foods or functional foods, or probiotics.

In another aspect, the invention provides the use of a gram positive bacterium, preferably a lactic acid bacterium (LAB) or *Bifidobacterium*, lacking TrePP activity as a probiotic or food additive, more specifically as a non-medicinal probiotic or food additive. Without limitation, such food additive may be a starter culture, preferably a starter culture for the preparation of a food product. Hence, a related aspect provides the use of a gram positive bacterium, preferably a lactic acid bacterium (LAB) or *Bifidobacterium*, lacking TrePP activity as a starter culture, preferably a starter culture for the preparation of a food product, more particularly wherein the food product is a non-medicinal food product.

A further aspect provides a probiotic composition or food additive, more specifically a non-medicinal probiotic composition or food additive, comprising a gram positive bacterium, preferably a lactic acid bacterium (LAB) or *Bifidobacterium*, lacking TrePP activity. Without limitation, such food additive may be a starter culture, preferably a starter culture for the preparation of a food product. Hence, a related aspect provides a starter culture, preferably a starter culture for the preparation of a food product, comprising a gram positive bacterium, preferably a lactic acid bacterium (LAB) or *Bifidobacterium*, lacking TrePP activity.

Also provided by an aspect of the invention is a method for preparing a food product, comprising admixing a gram positive bacterium, preferably a lactic acid bacterium (LAB) or *Bifidobacterium*, lacking TrePP activity, or said food additive or said starter culture with a substrate material that is capable of being fermented by the gram positive bacterium, preferably a lactic acid bacterium (LAB) or *Bifidobacterium*. In embodiments, such method may further comprise the step of fermenting said substrate material. As well provided is thus a food product obtainable by any such method. A food product may encompass without limitation probiotics.

Another aspect provides a method for preparing a medicament, such as a pharmaceutical formulation, nutraceutical, medical food or functional food or probiotic, or for preparing a probiotic composition or food additive, more specifically a non-medicinal probiotic composition or food additive, or for preparing a starter culture, preferably a starter culture for the preparation of a food product, comprising the steps of: i) propagating a gram positive bacterium, preferably a lactic acid bacterium (LAB) or *Bifidobacterium*, lacking TrePP activity in a medium comprising a substrate material capable of being fermented by said gram positive bacterium, preferably a lactic acid bacterium (LAB) or *Bifidobacterium*, and ii) formulating the so propagated gram positive bacterium, preferably a lactic acid bacterium (LAB) or *Bifidobacterium*, into, respectively, the medicament or probiotic composition or food additive or starter culture. Hence, also covered is the use of a gram positive bacterium, preferably a lactic acid bacterium (LAB) or *Bifidobacterium*, lacking TrePP activity for the preparation of a medicament, such as a pharmaceutical formulation, nutraceutical, medical food or functional food or probiotic, or for preparation of a probiotic composition or food additive, more specifically a non-medicinal probiotic composition or food additive, or for preparation of a starter culture, preferably a starter culture for the preparation of a food product.

The inventors have found that gram positive bacteria, such as LAB or *Bifidobacteria*, as described herein not only are capable of intracellular trehalose accumulation, even independent of the carbon source, but also that the gram positive bacterium show greatly enhanced resistance to various stress- and storage-associated conditions. For example, the gram positive bacterium are more resistant to storage-associated manipulations, such as drying, freezing, spray drying, or freeze-drying (lyophilisation). The gram positive bacterium also display enhanced survival, independent of the feeding or fasting status, in the gastro-intestinal system, indicating improved resistance to acidity and bile lysis. The performance of the gram positive bacterium as described herein, whether in a medicinal setting or in the food industry, is more reproducible than previously known. Hence the gram positive bacterium embodying the principles of the invention provide for a more robust environmental as well as bio-resistance.

In an aspect, the invention thus also relates to a method for internally accumulating trehalose in a gram positive bacterium, preferably a lactic acid bacterium (LAB) or *Bifidobacterium*, comprising propagating a gram positive bacterium, preferably a lactic acid bacterium (LAB) or *Bifidobacterium*, lacking TrePP activity in a medium comprising a substrate material capable of being fermented by said gram positive bacterium.

In a further aspect, the invention relates to a method for improving stress resistance or manufacturing, processing and/or storage characteristics of a gram positive bacterium, preferably a lactic acid bacterium (LAB) or *Bifidobacterium*, comprising modifying the gram positive bacterium, preferably a lactic acid bacterium (LAB) or *Bifidobacterium*, such as to lack TrePP activity. Preferably, the stress resistance or manufacturing, processing and/or storage characteristics may be one or more selected from the group comprising resistance to acid conditions, resistance to bile salts, resistance to heat, resistance to salt, resistance to drying, freezing, spray-drying, or freeze-drying, and osmotic resistance.

Preferably, in the aforementioned gram positive bacterium, preferably a lactic acid bacterium (LAB) or *Bifidobacterium*, lacking TrePP activity, the gene encoding endogenous TrePP has been partially or completely deleted, disrupted or inactivated such as being incapable of producing functional trePP gene product. It shall be appreciated that such deletion, disruption or inactivation may target for example the coding sequence of the trePP gene and/or the promoter from which trePP is expressed.

In preferred embodiments, the gram positive bacterium, preferably a lactic acid bacterium (LAB) or *Bifidobacterium*, lacking TrePP activity as employed herein does not contain functional heterologous trehalose 6-phosphate phosphatase. As already explained, overexpression of heterologous trehalose 6-phosphate phosphatase, such as for example otsB from *Escherichia coli* or from *Propionibacterium freudenreichii*, was previously presumed to be requisite for achieving trehalose accumulation in gram positive bacterium, preferably a lactic acid bacterium (LAB) or *Bifidobacterium*.

In preferred embodiments, the gram positive bacterium, preferably a lactic acid bacterium (LAB) or *Bifidobacterium*, lacking TrePP activity as employed herein does not contain functional heterologous trehalose 6-phosphate synthase. As already explained, overexpression of heterologous trehalose 6-phosphate synthase, such as for example otsA from *Escherichia coli*, was previously indicated for achieving trehalose accumulation in LAB.

In preferred embodiments, the gram positive bacterium, preferably a lactic acid bacterium (LAB) or *Bifidobacterium*, lacking TrePP activity as employed herein does not contain functional heterologous trehalose 6-phosphate phosphatase and does not contain functional heterologous trehalose 6-phosphate synthase.

In preferred embodiments, the gram positive bacterium, preferably a lactic acid bacterium (LAB) or *Bifidobacterium*, lacking TrePP activity as employed herein may lack cellobiose-specific PTS system II C component (ptcC) activity. Preferably, in such gram positive bacterium, preferably a lactic acid bacterium (LAB) or *Bifidobacterium*, also lacking ptcC activity, the gene encoding endogenous ptcC has been partially or completely deleted, disrupted or inactivated such as being incapable of producing functional ptcC gene product. It shall be appreciated that such deletion, disruption or inactivation may target for example the coding sequence of the ptcC gene and/or the promoter from which ptcC is expressed. The inventors have unexpectedly observed that over time the accumulated trehalose leaks to some extent out of the cells through an up to now unanticipated and unidentified trehalose exit port, whereby the trehalose can be detected in the supernatant. Surprisingly, they found that inactivation of ptcC prevents release of trehalose. These findings are all the more unexpected, because ptcC up to now has never been associated with trehalose transport, and has not been suggested as a trehalose exit port responsible for trehalose leakage and release into the surroundings. Also surprisingly, the known and characterized trehalose transporters do not seem responsible for this mechanism of trehalose leakage.

In preferred embodiments, the gram positive bacterium, preferably a lactic acid bacterium (LAB) or *Bifidobacterium*, lacking TrePP activity as employed herein may overexpress one or more trehalose transporters, preferably endogenous trehalose transporters, such as one or more phosphotransferase system genes comprised in the trehalose operon. The inventors have surprisingly found that such overexpression, in contrast to the native trehalose induced expression, further enhances the capacity of the gram positive bacterium, preferably a lactic acid bacterium (LAB) or *Bifidobacterium*, to accumulate and/or retain intracellular trehalose.

To recap, in some embodiments the gram positive bacterium, preferably a lactic acid bacterium (LAB) or *Bifidobacterium*, lacking TrePP activity as employed herein may additionally display any one, any two or all three of the following characteristics: (a) the gram positive bacterium does not contain functional heterologous trehalose 6-phosphate phosphatase; (b) the gram positive bacterium lacks ptcC activity; (c) the gram positive bacterium overexpresses one or more trehalose transporters. In preferred embodiments, the gram positive bacterium lacking TrePP activity may additionally display characteristic (a), or more preferably may additionally display characteristics (a) and (b), or may even more preferably additionally display characteristics (b) and (c), or may very preferably additionally display characteristics (a) and (b) and (c).

In this connection, a further aspect of the present invention is a gram positive bacterium, preferably a lactic acid bacterium (LAB) or *Bifidobacterium*, lacking TrePP activity and further displaying any one or preferably both of the following characteristics: (i) the gram positive bacterium lacks ptcC activity; (ii) the gram positive bacterium overexpresses one or more trehalose transporters.

A related aspect concerns a LAB lacking TrePP activity and not containing functional heterologous trehalose 6-phosphate phosphatase, and further displaying any one or preferably both of the following characteristics: (i) the LAB lacks ptcC activity; (ii) the LAB overexpresses one or more trehalose transporters.

In preferred embodiments, the gram positive bacterium, preferably a lactic acid bacterium (LAB) or *Bifidobacterium*, as disclosed or employed herein may additionally contain one or more heterologous gene product. In some preferred embodiments, particularly wherein the gram positive bacterium, preferably a lactic acid bacterium (LAB) or *Bifidobacterium*, is intended for a medicinal use, such gene product(s) may be prophylactic and/or therapeutic gene product(s) or antigen(s).

In this connection, a further aspect of the present invention is a gram positive bacterium, preferably a lactic acid bacterium (LAB) or *Bifidobacterium*, lacking TrePP activity and additionally containing one or more heterologous gene products, preferably prophylactic and/or therapeutic gene product(s). This gram positive bacterium may further optionally display any one or preferably both of the following characteristics: (i) the gram positive bacterium lacks ptcC activity; (ii) the gram positive bacterium overexpresses one or more trehalose transporters.

A related aspect is a gram positive bacterium, preferably a lactic acid bacterium (LAB) or *Bifidobacterium*, lacking TrePP activity and not containing functional heterologous trehalose 6-phosphate phosphatase and additionally containing one or more heterologous gene products, preferably prophylactic and/or therapeutic gene product(s). This gram positive bacterium may further optionally display any one or preferably both of the following characteristics: (i) the gram positive bacterium lacks ptcC activity; (ii) the gram positive bacterium overexpresses one or more trehalose transporters.

In certain embodiments, the gram positive bacterium, preferably a lactic acid bacterium (LAB) or *Bifidobacterium*, or medicament or food additive or probiotic composition or starter culture as disclosed or employed herein may be dried, frozen, spray-dried, or freeze-dried (lyophilized). Accordingly, in some embodiments, any of the aforementioned methods for preparing a medicament, or for preparing a food additive, or for preparing a starter culture, or for preparing a probiotic compositions, or for internally accumulating trehalose in a gram positive bacterium, preferably a lactic acid bacterium (LAB) or *Bifidobacterium*, or for improving stress resistance or manufacturing, processing and/or storage characteristics of a gram positive bacterium, preferably a lactic acid bacterium (LAB) or *Bifidobacterium*, may further comprise drying, spray-drying, freezing or freeze-drying (lyophilizing) the LAB, medicament, food additive, probiotic composition, or starter culture.

In certain embodiments of the aforementioned method for preparing a medicament, or for preparing a food additive, or for preparing a starter culture, or in certain embodiments of the aforementioned method for internally accumulating trehalose in the gram positive bacterium, preferably a lactic acid bacterium (LAB) or *Bifidobacterium*, the culture medium may comprise maltose or glucose or a combination of maltose and glucose, as a carbon source, preferably as main or even sole carbon source. In certain embodiments, the culture medium substantially does not contain externally (exogenously) added trehalose. The inventors have surprisingly found that gram positive bacteria, such as lactic acid bacteria (LAB) or *Bifidobacteria*, as disclosed herein have acquired the capacity to utilize carbon sources such as maltose or glucose to accumulate trehalose inside the cells. Accordingly, the gram positive bacteria according to the invention can advantageously be grown on for instance maltose as the sole carbon source, which is cheaper than trehalose, yet will accumulate intracellular trehalose. Nevertheless, it shall be appreciated that in certain embodiments, the culture medium may contain externally (exogenously) added trehalose.

The above and further aspects and preferred embodiments of the invention are described in the following sections and in the appended claims. The subject matter of appended claims is hereby specifically incorporated in this specification.

DETAILED DESCRIPTION OF THE INVENTION

Figure 1:
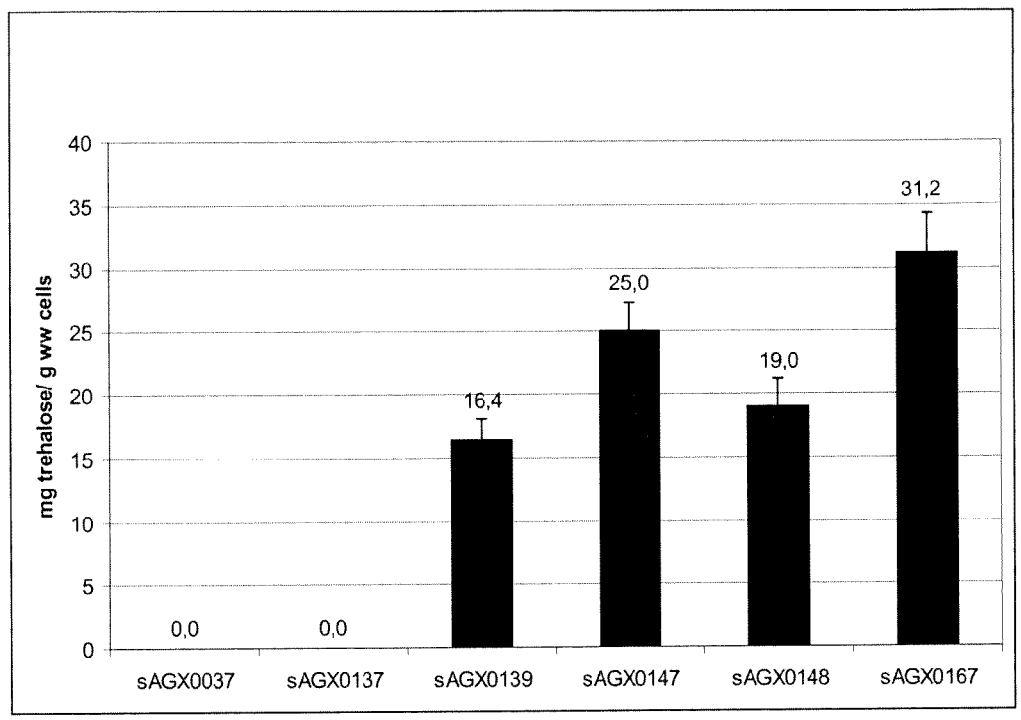
FIG. 1: Intracellular trehalose accumulation is possible following trePP inactivation, following otsB expression or a combination thereof.
Figure 1:
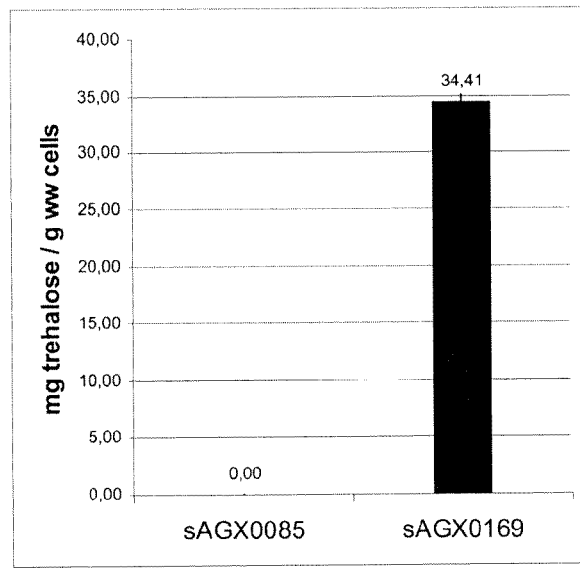

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980).

Disclosed herein is a gram positive bacterium, preferably a lactic acid bacterium (LAB) or *Bifidobacterium*, lacking trehalose 6-phosphate phosphorylase (TrePP) activity.

In an aspect, the gram positive bacterium, preferably a lactic acid bacterium (LAB) or *Bifidobacterium*, is for use as a medicament, i.e., for use in treatment. A further aspect provides a medicament comprising a gram positive bacterium, preferably a lactic acid bacterium (LAB) or *Bifidobacterium*, lacking TrePP activity. Disclosed is also the use of a gram positive bacterium, preferably a lactic acid bacterium (LAB) or *Bifidobacterium*, lacking TrePP activity for the manufacture of a medicament. Such medicament may be provided, for example, as a pharmaceutical formulation, nutraceutical, probiotic, medical or functional food.

Another aspect provides the use of a gram positive bacterium, preferably a lactic acid bacterium (LAB) or *Bifidobacterium*, lacking TrePP activity as a probiotic or a food additive, more specifically as a non-medicinal probiotic or food additive. A related aspect provides the use of a gram positive bacterium, preferably a lactic acid bacterium (LAB) or *Bifidobacterium*, lacking TrePP activity as a starter culture, preferably a starter culture for the preparation of a food product, more particularly wherein the food product is a non-medicinal food product.

A further aspect thus provides a probiotic or food additive, more specifically a non-medicinal probiotic or food additive, comprising a gram positive bacterium, preferably a lactic acid bacterium (LAB) or *Bifidobacterium*, lacking TrePP activity. A related aspect provides a starter culture, preferably a starter culture for the preparation of a food product, more particularly wherein the food product is a non-medicinal food product, said starter culture comprising a gram positive bacterium, preferably a lactic acid bacterium (LAB) or *Bifidobacterium*, lacking TrePP activity.

As used herein, the term "gram-positive bacterium" has its common meaning known in the art. By means of further guidance, a gram-positive bacterium can be identified by Gram staining as retaining crystal violet stain.

In a preferred embodiment, the gram-positive bacterium according to the invention is non-pathogenic in the sense that it does not cause harm or does not lead to deleterious effects when administered to an intended subject.

As used herein, the term "lactic acid bacterium" of "LAB" relates to a gram-positive bacterium which is non-pathogenic in the sense that it does not cause harm or does not lead to deleterious effects when administered to an intended subject, and which preferably belongs to the bacterial genera of *Lactococcus, Lactobacillus, Leuconostoc, Pediococcus, Streptococcus, Aerococcus, Carnobacterium, Enterococcus, Oenococcus, Sporolactobacillus, Tetragenococcus, Vagococcus*, and *Weisella*. More preferably, the LAB may be a *Lactococcus* species, such as, but not limited to *Lactococcus lactis, Lactococcus garvieae, Lactococcus piscium, Lactococcus plantarum* and *Lactococcus raffinolactis*, and any subspecies and strains thereof. Most preferably, the *Lactococcus* species may be *Lactococcus lactis*, and any subspecies and strain thereof, such as without limitation *Lactococcus lactis* ssp. *cremoris, Lactococcus lactis* ssp. *hordniae, Lactococcus lactis* ssp. *lactis, Lactococcus lactis* ssp. bv. *diacetylactis*. Further preferably, the *Lactococcus lactis* may be *Lactococcus lactis* ssp. *cremoris* or *Lactococcus lactis* ssp. *lactis*, more preferably *Lactococcus lactis* ssp. *cremoris*, and encompasses any strains thereof, such as, e.g., *Lactococcus lactis* ssp. *cremoris* SK11, *Lactococcus lactis* ssp. *cremoris* MG1363, or *Lactococcus lactis* ssp *lactis* IL1403. Also preferably, the LAB may an *Enterococcus* sp., preferably *Enterococcus faecalis, Enterococcus faecium* and any subspecies and strains thereof, such as, without limitation *Enterococcus faecium* strain LMG15709.

*Bifidobacterium* is a genus of Gram-positive, non-motile, often branched anaerobic bacteria. Bifidobacteria as used herein may include *B. adolescentis, B. angulatum, B. animalis, B. asteroides, B. bifidum, B. boum, B. breve, B. catenulatum, B. choerinum, B. coryneforme, B. cuniculi, B. denticolens, B. dentium, B. gallicum, B. gallinarum, B. indicum, B. infantis, B. inopinatum, B. lactis, B. longum, B. magnum, B. merycicum, B. minimum, B. pseudocatenulatum, B. pseudolongum, B. pullorum, B. ruminantium, B. saeculare, B. subtile, B. suis, B. thermacidophilum, B. thermophilum*. Preferably, the *Bifidobacterium* is *B. adolescentis, B. bifidum, B. breve, B. infantis, B. longum*. It is to be understood that all subspecies and strains of *Bifidobacteria* are also included.

As used herein, the term "trehalose 6-phosphate phosphorylase", "trePP", or "TrePP" relates to an enzyme which phosphorylates trehalose 6-phosphate, preferably an enzyme which catalyzes the reaction, preferably the reversible reaction, of α,α-trehalose-6-phosphate with phosphate to yield glucose-6-phosphate and β-D-glucose-1-phosphate, or vice versa. Synonyms for trePP are for instance trehalose-6-phosphate:phosphate β-D-glucosyltransferase and α,α-trehalose-6-phosphate:phosphate β-D-glucosyltransferase. By means of example, the nucleic acid and protein sequence of trePP of *Lactococcus lactis* ssp. cremoris MG1363 is represented by SEQ ID NOs: 1 and 2, respectively (corresponding to Genbank accession numbers NC_009004.1 (region 449195-451504) and YP_001031805.1, respectively). In an embodiment, the trePP as used herein relates to a gene or protein having the nucleic acid or amino acid sequence of SEQ ID NOs: 1 and 2, respectively, or having a nucleic acid encoding SEQ ID NO: 2. In a further embodiment, the trePP as used herein relates to a gene or protein having the nucleic acid or amino acid sequence which is at least 75% identical to SEQ ID NOs: 1 and 2, respectively, such as for instance at least 75%, 80%, 85%, 90%, 95% or more % identical. In another embodiment, the trePP as used herein encodes a protein which is at least 75% identical to SEQ ID NO: 2, such as for instance at least 75%, 80%, 85%, 90%, 95% or more % identical. Preferably, the above described sequences relate to or encode a functional trePP protein. In another embodiment, the trePP as used herein is a gram positive bacterium, preferably a lactic acid bacterium (LAB) or *Bifidobacterium*, orthologue of SEQ ID NOs: 1 and 2.

Methods for comparing sequences and determining sequence identity are well known in the art. By means of example, percentage of sequence identity refers to a percentage of identical nucleic acids or amino acids between two sequences after alignment of these sequences. Alignments and percentages of identity can be performed and calculated with various different programs and algorithms known in the art. Preferred alignment algorithms include BLAST®, which is a registered trademark of the National Library of Medicine (Altschul, 1990; available for instance at the NCBI website) and Clustal (reviewed in Chema, 2003; available for instance at the EBI website). Preferably, BLAST® is used to calculate the percentage of identity between two sequences, such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

The activity of trePP can be measured directly or indirectly. One way to indirectly determine the activity is by means of gene sequencing. In this way, partial or complete deletions, disruptions or inactivating mutations can be readily identified. A direct way to determine the activity can for instance be based on assays with cell extracts wherein substrate consumption or reaction product formation is measured (e.g. the substrate trehalose 6-phosphate or the reaction products glucose-6-phosphate and β-D-glucose-1-phosphate), possibly combined with prior metabolic labelling. Substrate and products can also be readily determined by for instance high performance anion exchange chromatography (HPAEC), as for instance described in Andersson et al. 2001 (supra).

As used herein, the term "lacking trePP activity" means that no or substantially no trePP activity is present. By means of further guidance, the trePP activity is less than 20% of the trePP activity of wild type gram positive bacterium, preferably a lactic acid bacterium (LAB) or *Bifidobacterium*. For instance, the trePP activity is less than 15%, preferably less than 10%, more preferably less than 5%, even more preferably less than 1% of wild type trePP activity. As indicated before, most preferably the trePP activity is undetectable or substantially or completely absent.

As used herein, the term "medicament" also encompasses the terms "drug", "therapeutic", and other terms which are used in the field of medicine to indicate a preparation with therapeutic or prophylactic effect.

As used herein, the terms "treat" or "treatment" refer to both therapeutic treatment and prophylactic or preventative measures, wherein the object is to prevent or slow down (lessen) an undesired physiological change or disorder. The terms "treatment", "treating", and the like, as used herein also include amelioration or elimination of a developed disease or condition once it has been established or alleviation of the characteristic symptoms of such disease or condition. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement.

As used herein, "nutraceuticals" generally encompass foods or food products that provide health and medical benefits. Nutraceuticals are edible and may be eaten directly by humans, but are preferably provided to humans in the form of additives or nutritional supplements, e.g., in the form of tablets of the kind sold in health food stores, or as ingredients in edible solids, more preferably processed food products such as cereals, breads, tofu, cookies, ice cream, cakes, potato chips, pretzels, cheese, etc., and in drinkable liquids e.g., beverages such as milk, soda, sports drinks, and fruit juices. Especially preferred processes for producing nutraceuticals involve only naturally derived solvents. Nutraceuticals may preferably contain relatively high levels of health-enhancing substances Nutraceuticals may be intermixed with one another to increase their health-enhancing effects.

In contrast to nutraceuticals, the so-called "medical foods" are not meant to be used by the general public and are not available in stores or supermarkets. Medical foods are not those foods included within a healthy diet to decrease the risk of disease, such as reduced-fat foods or low-sodium foods, nor are they weight loss products. A physician prescribes a medical food when a patient has special nutrient needs in order to manage a disease or health condition, and the patient is under the physician's ongoing care. The label states that the product is intended to be used to manage a specific medical disorder or condition. An example of a medical food is nutritionally diverse medical food designed to provide targeted nutritional support for patients with chronic inflammatory conditions. Active compounds of this product are for instance one or more of the compounds described herein. Functional foods may encompass those foods included within a healthy diet to decrease the risk of disease, such as reduced-fat foods or low-sodium foods, or weight loss products.

As used herein, the term "probiotics" refers to bacteria that help maintain the natural balance of microorganisms (microflora) in the intestines camera. Also, the normal human digestive tract contains probiotic bacteria that reduce the growth of harmful bacteria and promote a healthy digestive system. The largest group of probiotic bacteria in the intestine is LAB. As used herein, a "probiotic composition" is a composition, preferably an edible composition, comprising a probiotic. The term "probiotic composition" as used herein may be used interchangeably with "dietary supplement". The probiotic composition as defined herein can find use as supplement to food and beverages, and as pharmaceutical formulations for enteral or parenteral application which may be solid formulations such as capsules or tablets, or liquid formulations, such as solutions or suspensions. Such formulations may include without limitation drinks (e.g. Actimel®, Yakult®, DanActive® . . . ), drink yoghurts, yoghurt, fresh cheese, cream, sour cream, etc. Hence, it shall be appreciated that a probiotic or probiotic composition may be for medicinal or non-medicinal applications.

The term "starter culture" refers to a microbiological culture which actually performs fermentation. These starters usually consist of a cultivation medium, such as grains, seeds, or nutrient liquids that have been well colonized by the microorganisms used for the fermentation. As used herein, the term starter culture preferably refers to a high density starter culture. Accordingly, a starter culture may refer to a composition comprising live microorganisms that are capable of initiating or effecting fermentation of organic material, optionally after being cultivated in a separate starter medium for obtaining a high density culture. Alternatively, the starter culture may be dried, spray-dried, frozen or freeze-dried.

As indicated before, the present inventors have surprisingly found that the mere absence of trePP is sufficient for intracellular trehalose accumulation in gram positive bacterium, preferably a lactic acid bacterium (LAB) or *Bifidobacterium*. In contrast herewith, it has been previously thought that the presence of a heterologous trehalose 6-phosphate phosphatase and/or a heterologous trehalose 6-phosphate synthase, such as otsB and otsA, respectively, is essential for intracellular trehalose accumulation. Accordingly, in an embodiment, the invention relates to the gram positive bacterium, preferably a lactic acid bacterium (LAB) or *Bifidobacterium*, as described herein, not containing functional heterologous otsB, preferably no functional heterologous trehalose 6-phosphate phosphatase. In a further embodiment, the gram positive bacterium, preferably a lactic acid bacterium (LAB) or *Bifidobacterium*, as described herein does not contain a functional heterologous otsA, preferably no functional heterologous trehalose 6-phosphate synthase. In yet another embodiment, the gram positive bacterium, preferably a lactic acid bacterium (LAB) or *Bifidobacterium*, as described herein does not contain a functional heterologous otsA and does not contain a functional heterologous otsB. In a further embodiment, the gram positive bacterium, preferably a lactic acid bacterium (LAB) or *Bifidobacterium*, as described herein does not contain a functional heterologous trehalose 6-phosphate synthase and does not contain a functional heterologous trehalose 6-phosphate phosphatase. In yet a further embodiment, the gram positive bacterium, preferably a lactic acid bacterium (LAB) or *Bifidobacterium*, as described herein does not contain a functional heterologous gene involved in the metabolism (either catabolic or anabolic) of trehalose or trehalose 6-phosphate. Such genes encompass, without limitation trehalase, trehalose phosphorylase, and trehalose 6-phosphate hydrolase.

As used herein, the term "does not contain" or "not containing" preferably relates to gram positive bacterium, preferably a lactic acid bacterium (LAB) or *Bifidobacterium*, which do not express a particular gene product, i.e. no functional or active protein is produced in said gram positive bacterium, preferably a lactic acid bacterium (LAB) or *Bifidobacterium*.

As used herein, the term "trehalose 6-phosphate phosphatase" relates to an enzyme which dephosphorylates trehalose 6-phosphate, preferably an enzyme which catalyzes the reaction of trehalose-6-phosphate to yield phosphate and trehalose. Trehalose 6-phosphate phosphatase belongs to the family of Phosphoric Monoester Hydrolases. Synonyms for trehalose 6-phosphate phosphatase are for instance α,α-trehalose-6-phosphate phosphohydrolase, trehalose-6-phosphate phosphohydrolase, and trehalose 6-phosphatase. By means of example, the nucleic acid and protein sequence of trehalose 6-phosphate phosphatase of *E. coli* (i.e., otsB) is represented by SEQ ID NOs: 3 and 4, respectively (corresponding to Genbank accession numbers X69160.1 (nucleotide positions 675-1475) and P31678.2, respectively). In an embodiment, the trehalose 6-phosphate phosphatase as used herein relates to a gene or protein having the nucleic acid or amino acid sequence of SEQ ID NOs: 3 and 4, respectively, or having a nucleic acid encoding SEQ ID NO: 4. In a further embodiment, the trehalose 6-phosphate phosphatase as used herein relates to a gene or protein having the nucleic acid or amino acid sequence which is at least 75% identical to SEQ ID NOs: 3 and 4, respectively, such as for instance at least 75%, 80%, 85%, 90%, 95% or more % identical. In another embodiment, the trehalose 6-phosphate phosphatase as used herein encodes a protein which is at least 75% identical to SEQ ID NO: 4, such as for instance at least 75%, 80%, 85%, 90%, 95% or more % identical. Preferably, the above described sequences relate to or encode a functional trehalose 6-phosphate phosphatase protein. In another embodiment, the trehalose 6-phosphate phosphatase as used herein is a gram positive bacterium, preferably a lactic acid bacterium (LAB) or *Bifidobacterium*, orthologue of SEQ ID NOs: 3 and 4.

As used herein, the term "trehalose 6-phosphate synthase" relates to an enzyme which dephosphorylates trehalose 6-phosphate, preferably an enzyme which catalyzes the reaction of glucose 6-phosphate with UDP-glucose to yield trehalose 6-phosphate. Trehalose 6-phosphate synthase belongs to the family of glycosyltransferases. Synonyms for trehalose 6-phosphate synthase are for instance trehalose phosphate-uridine diphosphate glucosyltransferase, phosphotrehalose-uridine diphosphate transglucosylase, uridine diphosphoglucose phosphate glucosyltransferase, and α,α-trehalose-6-phosphate synthase. By means of example, the nucleic acid and protein sequence of trehalose 6-phosphate synthase of *E. coli* (i.e. otsA) is represented by SEQ ID NOs: 5 and 6, respectively (corresponding to Genbank accession numbers X69160.1 (nucleotide positions 1450-2874) and P31677.3, respectively). In an embodiment, the trehalose 6-phosphate synthase as used herein relates to a gene or protein having the nucleic acid or amino acid sequence of SEQ ID NOs: 5 and 6, respectively, or having a nucleic acid encoding SEQ ID NO: 6. In a further embodiment, the trehalose 6-phosphate synthase as used herein relates to a gene or protein having the nucleic acid or amino acid sequence which is at least 75% identical to SEQ ID NOs: 5 and 6, respectively, such as for instance at least 75%, 80%, 85%, 90%, 95% or more % identical. In another embodiment, the trehalose 6-phosphate synthase as used herein encodes a protein which is at least 75% identical to SEQ ID NO: 6, such as for instance at least 75%, 80%, 85%, 90%, 95% or more % identical. Preferably, the above described sequences relate to or encode a functional trehalose 6-phosphate synthase protein. In another embodiment, the trehalose 6-phosphate synthase as used herein is a gram positive bacterium, preferably a lactic acid bacterium (LAB) or *Bifidobacterium*, orthologue of SEQ ID NOs: 5 and 6.

It is to be understood that, as used herein, the absence of functional heterologous trehalose 6-phophase phosphatase or synthase (or any other trehalose related metabolic enzyme) relates to the absence of any or substantially any heterologous trehalose 6-phophase phosphatase or synthase activity. Such activity can be determined as described herein elsewhere. In an embodiment, the gram positive bacterium, preferably a lactic acid bacterium (LAB) or *Bifidobacterium*, as described herein do not express these enzymes.

The inventors have found that trehalose to some extent leaks from cells through an up to now unidentified or unanticipated trehalose exit port and can be recovered in the supernatant. Surprisingly, the inventors found that the disruption of ptcC circumvents the release of trehalose. Accordingly, in an embodiment, the invention relates to gram positive bacterium, preferably a lactic acid bacterium (LAB) or *Bifidobacterium*, as described herein, lacking cellobiose-specific PTS system IIC component (ptcC) activity.

"Cellobiose-specific PTS system IIC component" or "ptcC" as used herein refers to a phosphotransferase system component. The phosphotransferase system is involved in catalyzing the transfer of the phosphoryl group from phosphoenolpyruvate to incoming sugar substrates concomitant with their translocation across the cell membrane. ptcC is the transmembrane component of a cellobiose-specific PTS system. ptcC has up till now not been implicated in trehalose transport, let alone being involved in trehalose leakage from gram positive bacterium, preferably a lactic acid bacterium (LAB) or *Bifidobacterium*. By means of example, the nucleic acid and protein sequence of ptcC of *Lactococcus lactis* ssp. *cremoris* MG1363 is represented by SEQ ID NOs: 7 and 8, respectively (corresponding to Genbank accession numbers NC_009004.1 (region 430271-431608) and YP_001031790.1, respectively). In an embodiment, the ptcC as used herein relates to a gene or protein having the nucleic acid or amino acid sequence of SEQ ID NOs: 7 and 8, respectively, or having a nucleic acid encoding SEQ ID NO: 8. In a further embodiment, the ptcC as used herein relates to a gene or protein having the nucleic acid or amino acid sequence which is at least 75% identical to SEQ ID NOs: 7 and 8, respectively, such as for instance at least 75%, 80%, 85%, 90%, 95% or more % identical. In another embodiment, the ptcC as used herein encodes a protein which is at least 75% identical to SEQ ID NO: 8, such as for instance at least 75%, 80%, 85%, 90%, 95% or more % identical. Preferably, the above described sequences relate to or encode a functional ptcC protein. In another embodiment, the ptcC as used herein is a gram positive bacterium, preferably a lactic acid bacterium (LAB) or *Bifidobacterium*, orthologue of SEQ ID NOs: 7 and 8.

The gram positive bacterium, preferably a lactic acid bacterium (LAB) or *Bifidobacterium*, lacking trePP and/or ptcC activity according to the invention can be obtained by any means known in the art, be it using molecular biological methodology or obtained through high throughput screening of natural variants or variants obtained from random chemical or irradiation mutagenesis. (High throughput screening fro trePP KO can be performed by a method using the absence of growth on trehalose of the trePP defective strain or by high throughput sequencing and bioinformatic analysis of trePP orthologs or other methods). (for background relating to recombinant techniques and genetic manipulation of LAB see for instance "Genetics and Biotechnology of Lactic Acid Bacteria", eds. Gasson & de Vos, Blackie Academic & Professional, 1994 and "Genetics of Lactic Acid Bacteria", eds. Wood & Warner, Springer, 2003) In an embodiment, in the gram positive bacterium, preferably a lactic acid bacterium (LAB) or *Bifidobacterium*, according to the invention the gene encoding endogenous TrePP and/or PtcC and/or the promoters from which trePP and/or ptcC are expressed has been partially or completely deleted, disrupted or inactivated such as being incapable of producing functional trePP and/or ptcC gene product. Techniques for gene disruption are generally known in the art. By means of example, the endogenous trePP and/or ptcC gene can be inactivated by complete or partial removal of the coding region (knock-out) or alternatively complete or partial removal or mutagenesis of the promoter region. Alternatively, the trePP and/or ptcC gene may be insertionally inactivated (knock-in), thereby disrupting the endogenous coding sequence. For instance, premature stop codons or frame shift mutations may be introduced. The trePP and/or ptcC gene may also be mutagenized by introduction of one or more missense or nonsense mutations, as long as no or substantially no functional trePP and/or ptcC protein can be produced anymore, i.e. trePP and/or ptcC activity is (substantially) absent. It is to be understood that spontaneous mutations are also covered.

The inventors have further found that overexpressing one or more trehalose transporters further augments intracellular trehalose accumulation and/or retention in gram positive bacterium, preferably a lactic acid bacterium (LAB) or *Bifidobacterium*. Accordingly, in an embodiment, the invention relates to gram positive bacterium, preferably a lactic acid bacterium (LAB) or *Bifidobacterium*, as described herein, overexpressing, preferably constitutively overexpressing, one or more genes encoding a trehalose transporter. In a preferred embodiment, said trehalose transporters are endogenous trehalose transporters of gram positive bacterium, preferably a lactic acid bacterium (LAB) or *Bifidobacterium*. In a further preferred embodiment, the trehalose transporters are endogenous trehalose transporters located in the trehalose operon of gram positive bacterium, preferably a lactic acid bacterium (LAB) or *Bifidobacterium*. In yet another embodiment, the trehalose transporters are endogenous trehalose transporters of the phosphotransferase system (PTS) located within the trehalose operon of gram positive bacterium, preferably a lactic acid bacterium (LAB) or *Bifidobacterium*. In a preferred embodiment, the overexpression of the one or more trehalose transporters as described herein is accomplished by insertion of a promoter 5' to the one or more transporters such that the promoter is operably linked to the transporter sequence(s). Operably linked refers to a juxtaposition wherein the components so described are in a relationship permitting them to function in their intended manner. A promoter sequence "operably linked" to a coding sequence is ligated in such a way that expression of the coding sequence is achieved under conditions compatible with the promoter sequence. In an embodiment, said promoter is a strong promoter. In a further embodiment, said promoter is a constitutive promoter. In yet another embodiment, said promoter is an endogenous gram positive bacterium, preferably a lactic acid bacterium (LAB) or *Bifidobacterium*, promoter. Suitable promoters can be found for instance in WO 2008/084115, which incorporated herein in its entirety. In particular, the promoters listed in Table 12 of WO 2008/084115 are particularly suited to overexpress the transporters as described herein. Most preferably, the promoter is PhIIA (i.e. the promoter of the HU-like DNA-binding protein). Accordingly, in a preferred embodiment the PhIIA promoter is inserted upstream of the coding regions of the endogenous trehalose transporter(s) located in the trehalose operon of gram positive bacterium, preferably a lactic acid bacterium (LAB) or *Bifidobacterium*. In an embodiment, the PhIIA promoter has the sequence of SEQ ID NO: 13, corresponding to the PhIIA promoter of *Lactococcus lactis* ssp. *cremoris* MG1363. In another embodiment, the PhIIA promoter has a sequence which is at least 75% identical to SEQ ID NO: 13, such as at least 75%, 80%, 85%, 90%, 95% or more identical to SEQ ID NO: 13. In a further embodiment, the PhIIA is a gram positive bacterium, preferably a lactic acid bacterium (LAB) or *Bifidobacterium*, orthologue of SEQ ID NO: 13.

By means of example, the trehalose transporters referred to herein are represented by the *Lactococcus lactis* ssp. *cremoris* MG1363 nucleic acid and amino acid sequence of SEQ ID NOs: 9 and 10, respectively (corresponding to Genbank accession numbers NC_009004.1 (region 446937-447422) and YP_001031803.1, respectively), and/or SEQ ID NOs: 11 and 12, respectively (corresponding to Genbank accession numbers NC_009004.1 (region 447563-449128) and YP_001031804.1, respectively). In an embodiment, the overexpressed transporter(s) as used herein relate to a gene or protein having the nucleic acid or amino acid sequence of SEQ ID NOs: 9 and 10, respectively, and/or SEQ ID NOs: 11 and 12, respectively, or having a nucleic acid encoding SEQ ID NO: 10 and/or SEQ ID NO: 12. In a further embodiment, the overexpressed transporter(s) as used herein relates to a gene or protein having the nucleic acid or amino acid sequence which is at least 75% identical to SEQ ID NOs: 9 and 10, respectively, and/or SEQ ID NOs: 11 and 12, respectively, such as for instance at least 75%, 80%, 85%, 90%, 95% or more % identical. In another embodiment, the overexpressed transporter(s) as used herein encodes a protein which is at least 75% identical to SEQ ID NO: 10 and/or SEQ ID NO: 12, such as for instance at least 75%, 80%, 85%, 90%, 95% or more % identical. Preferably, the above described sequences relate to or encode (a) functional overexpressed, preferably constitutively overexpressed, transporter(s) protein(s). In another embodiment, the (constitutively) overexpressed transporter(s) as used herein is(are) a gram positive bacterium, preferably a lactic acid bacterium (LAB) or *Bifidobacterium*, orthologue(s) of SEQ ID NOs: 9 and 10 and/or SEQ ID NOs: 11 and 12.

In an embodiment, the invention relates to gram positive bacterium, preferably a lactic acid bacterium (LAB) or *Bifidobacterium*, which lack trePP and further displaying any one or preferably both of the following characteristics: (i) the gram positive bacterium lacks ptcC activity; (ii) the gram positive bacterium overexpresses, preferably constitutively overexpresses, one or more trehalose transporters, wherein the gram positive bacterium in addition contains functional heterologous trehalose 6-phosphate phosphatase, such as otsB and/or functional heterologous trehalose 6-phosphate synthase, such as otsA, more preferably wherein the gram positive bacterium contains at least said functional heterologous trehalose 6-phosphate phosphatase, even more preferably wherein the gram positive bacterium contains said functional heterologous trehalose 6-phosphate phosphatase but does not contain said functional heterologous trehalose 6-phosphate synthase. Each of these proteins is as described herein elsewhere. Particularly preferred is a genomic integration of the trehalose 6-phosphate phosphatase, wherein the integration is preferably as disclosed in European patent applications with application numbers 11168495.7 and 11173588.2. These applications relate to dual cistron expression systems and are incorporated herein by reference in their entirety. The preferred position of trehalose 6-phosphate phosphatase, preferably otsB, as it is used here, is as a second cistron behind the endogenous usp45 gene.

The gram positive bacterium, preferably a lactic acid bacterium (LAB) or *Bifidobacterium*, as described herein show an increased tolerance towards various environmental and storage associated insults or stress, such as an increased drying, spray-drying, freezing or freeze-drying resistance, as well as an increased resistance towards the harsh conditions in the gastrointestinal tract (e.g. acids and bile salts). The gram positive bacterium, preferably a lactic acid bacterium (LAB) or *Bifidobacterium*, according to the invention are therefore particularly well suited to be administered to a subject while showing an increased survival rate in the gastrointestinal tract. These gram positive bacterium, preferably a lactic acid bacterium (LAB) or *Bifidobacterium*, can therefore also be applied to deliver proteins to a subject. Accordingly, in an embodiment, the invention relates to gram positive bacterium, preferably a lactic acid bacterium (LAB) or *Bifidobacterium*, as described herein, containing one or more heterologous gene product, preferably one or more prophylactic and/or therapeutic gene product and/or antigen. Delivery of biological active polypeptides has for instance been described in WO 97/14806, WO 00/23471, WO 01/02570, WO 02/090551, WO 2005/111194, WO 2007/025977, WO 2007/063075, WO 2007/128757, WO 2008/071751, WO 2008/090223, WO 2004/046346, and WO 2010/034844. Preferably, the heterologous genes as described herein are integrated into the bacterial genome. A particularly preferred integration strategy is disclosed in European patent applications with application numbers 11168495.7 and 11173588.2, which are incorporated herein in their entirety by reference. In particular, the heterologous genes may be inserted polycistronically (e.g., bi-, tri- or multi-cistronically) as a second (or further) gene in a native (endogenous) locus, preferably an operon. In this way, the heterologous gene is expressed under control of a native (endogenous) promoter.

As used herein, the term "antigen" generally refers to a substance that evokes an immune response, including humoral immunity and/or cellular immunity response, and that is capable of binding with a product, e.g., an antibody or a T cell, of the immune response. An antigen as intended herein may in an alternative be such as to induce immunotolerance, e.g., may be an auto-antigen (including auto- and allo-antigens) or may be allergen. Hence, in a preferred example, an antigen requires a functioning immune system of a subject to which it is administered to elicit a physiological response from such a subject. The "antigen" as intended herein also encompasses "self-antigens" which do not provoke an immune response in a healthy individual but would do so in a person suffering from auto-immune disease, i.e. the failure of an organism to recognize its own constituent parts (down to the sub-molecular levels) as "self", which results in an immune response against its own cells and tissues. Any disease that results from such an aberrant immune response is termed an autoimmune disease. Accordingly, the "antigen" as intended herein also encompasses a (physiologically active) protein which would not provoke an immune response in a healthy individual but would do so in a person genetically deficient in said protein. In addition, the "antigen" as intended herein also encompasses an allergen which would not provoke an immune response in a healthy individual but would do so in a person suffering from an allergic disease.

An antigen as intended herein may be derived from any polypeptide to which an immune response in a human or animal subject would be therapeutically useful, e.g., from a pathogen, e.g., from a viral, prokaryotic (e.g., bacterial) or eukaryotic pathogen, from a non-physiological protein (e.g., a protein derived from cancer tissue), from allergen (e.g., for eliciting immune tolerance), etc. An antigen could also be a metabolite of a protein. As an example, the antigen could be a polysaccharide, a lipid or other. Strong promoters as described here could drive the expression of the necessary enzymes to synthesize or assemble said polysaccharide, lipid or other.

The term "a prophylactically and/or therapeutically gene product", polypeptide or protein refers generally to a peptide, polypeptide or protein that, in a human or animal subject to which it is administered, does not elicit an immune response against itself (i.e., is non-vaccinogenic) and is able to achieve a prophylactic and/or therapeutic effect. Hence, the prophylactic and/or therapeutic effect of such a peptide, polypeptide or protein would be expected to be directly linked to its own natural biological function whereby it can achieve particular effects in a body of a subject; rather than producing a prophylactic and/or therapeutic effect by acting as an immunogenic and/or immunoprotective antigen in the subject. Hence, the non-vaccinogenic prophylactically and/or therapeutically active peptide, polypeptide or protein should be biologically active in its expressed form or, at least, must be converted into the biologically active form once released from the expressing host cell. Preferably, such biologically active form of the said peptide, polypeptide or protein may display a secondary and preferably also tertiary conformation which is the same or closely analogous to its native configuration.

Preferably, the prophylactic and/or therapeutic gene product, polypeptide or protein is also non-toxic and non-pathogenic. In a preferred embodiment, the prophylactically and/or therapeutically gene product, polypeptide or protein may be derived from human or animal, and may preferably correspond to the same taxon as the human or animal subject to which it is to be administered.

Non-limiting examples of suitable prophylactically and/or therapeutically gene products, polypeptides or proteins include ones which are capable of functioning locally or systemically, e.g., is/are capable of exerting endocrine activities affecting local or whole-body metabolism and/or is/are capable of the regulation of the activities of cells belonging to the immunohaemopoeitic system and/or is/are capable of affecting the viability, growth and differentiation of a variety of normal or neoplastic cells in the body or affecting the immune regulation or induction of acute phase inflammatory responses to injury and infection and/or is/are capable of enhancing or inducing resistance to infection of cells and tissues mediated by chemokines acting on their target cell receptors, or the proliferation of epithelial cells or the promotion of wound healing and/or is/are capable of modulating the expression or production of substances by cells in the body. Specific examples of such peptides, polypeptides and proteins include, without limitation, insulin, growth hormone, prolactin, calcitonin, luteinising hormone, parathyroid hormone, somatostatin, thyroid stimulating hormone, vasoactive intestinal polypeptide, cytokines such as IL-2, IL-3, IL-4, IL-5, IL-6, IL-7, IL-9, IL-10, IL-11, IL-12, IL-13, any of IL-14 to IL-32, in particular IL-27, GM-CSF, M-CSF, SCF, IFNs, EPO, G-CSF, LIF, OSM, CNTF, GH, PRL, the TNF family of cytokines, e.g., TNFα, TNFα, CD40, CD27 or FAS ligands, the IL-1 family of cytokines, the fibroblast growth factor family, the platelet derived growth factors, transforming growth factors and nerve growth factors, the epidermal growth factor family of cytokines, the insulin related cytokines, etc. Alternatively, the prophylactically and/or therapeutically active polypeptide can be a receptor or antagonist for the prophylactically and/or therapeutically active polypeptides as defined above. Alternatively, the prophylactically and/or therapeutically active polypeptide can be an antibody, such as a neutralizing antibody, or the likes thereof. Further specific examples of such suitable polypeptides are listed, e.g., in WO 96/11277, page 14, lines 1-30, incorporated herein by reference; in WO 97/14806, page 12, line 1 through page 13, line 27, incorporated herein by reference; or U.S. Pat. No. 5,559,007, col. 8, line 31 through col. 9, line 9, incorporated by reference herein. In an example, said prophylactically and/or therapeutically active peptide, polypeptide or protein may be IL-10, more preferably hIL-10, glucagon-like peptide-1 (GLP-1), more preferably hGLP-1, glucagon-like peptide-2 (GLP-2), more preferably hGLP-2, trefoil factors (TFF, e.g., TFF1, 2 and/or 3), or PYY, more preferably hPYY.

As mentioned, in embodiments the prophylactically and/or therapeutically active polypeptide can be an antibody, such as a neutralizing antibody, or the likes thereof. The antibody as described herein can be a full size antibody or a functional fragment thereof such as Fab, a fusion protein or a multimeric protein. In a preferred embodiment, the one or more heterologous genes encodes an antibody or a functional antibody fragment. As used herein, the term "functional" refers to an antibody fragment, which can still exert its intended function, i.e. antigen binding. The term antibody, as used here, includes, but is not limited to conventional antibodies, chimeric antibodies, dAb, bispecific antibody, trispecific antibody, multispecific antibody, bivalent antibody, trivalent antibody, multivalent antibody, VHH, nanobody, Fab, Fab', F(ab')$_2$ scFv, Fv, dAb, Fd, diabody, triabody, single chain antibody, single domain antibody, single antibody variable domain.

In the present context, the term "antibody" is used to describe an immunoglobulin whether natural or partly or wholly engineered. As antibodies can be modified in a number of ways, the term "antibody" should be construed as covering any specific binding molecule or substance having a binding domain with the required binding specificity for the other member of the pair of molecules, i.e. the target molecule, as defined supra. Thus, this term covers antibody fragments, derivatives, functional equivalents and homologues of antibodies, as well as single chain antibodies, bifunctional antibodies, bivalent antibodies, VHH, nanobodies, Fab, Fab', F(ab)$_2$, scFv, Fv, dAb, Fd, diabodies, triabodies and camelid antibodies, including any polypeptide comprising an immunoglobulin binding domain, whether natural or wholly or partially engineered. Chimeric molecules comprising an immunoglobulin binding domain, or equivalent, fused to another polypeptide are therefore included. The term also covers any polypeptide or protein having a binding domain which is, or is homologous to, an antibody binding domain, e.g. antibody mimics. Examples of antibodies are the immunoglobulin isotypes and their isotypic subclasses, including IgG (IgG1, IgG2a, IgG2b, IgG3, IgG4), IgA, IgD, IgM and IgE. The person in the art will thus appreciate that the present invention also relates to antibody fragments, comprising an antigen binding domain such as VHH, nanobodies Fab, scFv, Fv, dAb, Fd, diabodies and triabodies. In an embodiment, the invention relates to a gram-positive bacterium or a recombinant nucleic acid as described herein, wherein one exogenous gene encodes the light chain ($V_L$) of an antibody or of a functional fragment thereof, and another exogenous gene encodes the heavy chain ($V_H$) of the antibody or of a functional fragment thereof, more preferably wherein the functional fragment is Fab. In an embodiment, the exogenous gene encoding $V_L$ or functional fragment thereof is transcriptionally coupled to the 3' end of the exogenous gene encoding $V_H$ or functional fragment thereof.

In an embodiment, the (neutralizing) antibody as described herein at least partially or fully blocks, inhibits, or neutralises a biological activity of a target molecule, such as a cytokine or chemokine or a toxin. As used herein, the expression "neutralises" or "neutralisation" means the inhibition of or reduction in a biological activity of a cytokine or toxin as measured in vivo or in vitro, by methods known in the art, such as, for instance, as detailed in the examples. In particular, the inhibition or reduction may be measured by determining the colitic score or by determining the target molecule in a tissue or blood sample. As used herein, the expression "neutralises" or "neutralisation" means the inhibition of or reduction in a biological activity of a cytokine or toxin as measured in vivo or in vitro, by at least 10% or more, preferably by at least 20%, 30%, 40%, 50%, 60%, 70%, 80%, 90% and even more preferably by 100%.

Preferably, said antibody or functional fragment thereof inhibit the biological effect of cytokines chosen from the list of IL-1β, IL-2, IL-4, IL-5, IL-6, IL-7, IL-8, IL-9, IL-12 (or its subunits IL-12p35 and IL12p40), IL-13, IL-15, IL-16, IL-17, IL-18, IL-21, IL-23 (or its subunit IL-23p19), IL-27, IL-32 (and its splice variants), IFN (α, β, γ) and TNFα. Alternatively, these cytokines may be inhibited by binding molecules which are not antibodies. Preferably, said binding molecules are soluble cytokine receptors such as gp130, or are binding to the receptors of said cytokines, for example IL-2R (CD25, CD122, CD132), IL-12R (beta1, beta2), IL15R, IL-17R, IL-23R or IL-6R, without triggering an inflammatory signal. Preferably, said binding molecules are neutralizing chemokines chosen from the list of MIF, MIP-1α, MCP-1, RANTES and Eotaxin. Preferably, said binding molecules are solving the blockade of immune activation via binding to costimulatory molecules from the list of CD3/CD28, HVEM, B7.1/B7.2, CD40/CD40L(CD154), ICOS/ICOSL, OX40/X40L, CD27/CD27L(CD70), CD30/CD30L (CD153) and 41BB/41BBL. Preferably, said binding molecules are solving the blockade of inflammation via binding to adhesion molecules from the list I-CAM1, α4 integrin and α4β7 integrin. Preferably, said binding molecules have a costimulatory and agonistic effect on CD3, CTLA4 and/or PD1. Preferably, said binding molecules are neutralizing T-cells or B-cell activity by targeting CD25, CD20, CD52, CD95, BAFF, APRIL and/or IgE. Preferably, said binding molecules are solving the blockade of inflammation via binding to enzymes from the MMP family. Preferably, said binding molecules assert an anti-angiogenic effect, such as neutralizing αvβ3/α5β1 and IL-8 activity. In a further preferred embodiment said binding molecule or antibody (or functional fragment) is capable of neutralizing the biological effect of TNFα, IL-12, IFNγ, IL-23 or IL-17.

Non-limiting examples of antibodies or binding molecules which can be used as heterologous genes in the gram positive bacterium, preferably a lactic acid bacterium (LAB) or *Bifidobacterium*, as described herein include:

an anti-TNFα antibody, anti-TNFα antibody fragment, anti-TNFα single antibody variable domain, soluble TNF receptor or dominant negative variant of TNFα;

anti-IL-12 antibody, anti-IL-12 antibody fragment, anti-IL-12 single antibody variable domain, soluble IL-12 receptor, dominant negative variant of IL-12 or IL-12 dAb;

anti-IL-12p35 antibody, anti-IL-12p35 antibody fragment, anti-IL-12p35 single antibody variable domain, soluble IL-12p35 receptor, dominant negative variant of IL-12p35 or IL-12p35 dAb;

anti-IL-12p40 antibody, anti-IL-12p40 antibody fragment, anti-IL-12p40 single antibody variable domain, soluble IL-12p40 receptor, dominant negative variant of IL-12p40 or IL-12p40 dAb;

anti-IL-23 antibody, anti-IL-23 antibody fragment, anti-IL-23 single antibody variable domain, soluble IL-23 receptor, dominant negative variant of IL-23 or IL-23 dAb;

anti-IL-23p19 antibody, anti-IL-23p19 antibody fragment, anti-IL-23p19 single antibody variable domain, soluble IL-23p19 receptor, dominant negative variant of IL-23p19 or IL-23p19 dAb;

an anti-IFNγ antibody, anti-IFNγ antibody fragment, anti-IFNγ single antibody variable domain, soluble IFNγ receptor or dominant negative variant of IFNγ;

anti-IL-17 antibody, anti-IL-17 antibody fragment, anti-IL-17 single antibody variable domain, soluble IL-17 receptor, dominant negative variant of IL-17 or IL-17 dAb; and anti-MCP-1 antibody, anti-MCP-1 antibody fragment, anti-MCP-1 single antibody variable domain, soluble IL-17 receptor, dominant negative variant of MCP-1 or MCP-1 dAb.

In a preferred embodiment, said antibody is a Fab fragment (fragment antigen-binding). Fab fragments are well known in the art. By means of further guidance, a Fab fragment is a region on an antibody that binds to antigens. It is composed of one constant and one variable domain of each of the heavy and the light chain.

In an embodiment, the Fab is cA2 anti-TNF Fab (of which the polynucleotide and polypeptide sequences of the variable domain of the heavy chain and the light chain are disclosed in U.S. Pat. No. 6,790,444 as SEQ ID NO: 4 and 5 (heavy chain) and SEQ ID NO: 2 and 3 (light chain), respectively) or CDP870 anti-TNF Fab (of which the polynucleotide and polypeptide sequences of the heavy chain and the light chain are disclosed in WO 01/94585 as SEQ ID NO: 114 and 115 (heavy chain) and SEQ ID NO: 112 and 113 (light chain), respectively).

The skilled person will appreciate that antibodies, as are functional antibody fragments, and in particular Fab fragments, are composed of different individual polypeptides which may be covalently linked by disulphide bridges. In particular, the heavy chain and the light chain are encoded by separate individual coding sequences.

Accordingly, in an embodiment the heterologous gene disclosed herein encodes an antigen and/or a (neutralizing) antibody or functional fragment or variant thereof and/or a prophylactically and/or therapeutically active peptide, polypeptide or protein, wherein the said antigen is capable of eliciting an immune response, preferably protective immune response or immune tolerance response, in a human or animal subject, and/or the said prophylactically and/or therapeutically gene product, polypeptide or protein is capable of producing a prophylactic and/or therapeutic effect in a human or animal subject.

In an embodiment, the invention relates to gram positive bacterium, preferably a lactic acid bacterium (LAB) or *Bifidobacterium*, as described herein or the gram positive bacterium, preferably a lactic acid bacterium (LAB) or *Bifidobacterium*, for use as described herein which are formulated for storage. In particular, in an embodiment, the invention relates to gram positive bacterium, preferably a lactic acid bacterium (LAB) or *Bifidobacterium*, as described herein which are frozen, dried, freeze-dried, spray-dried or stored in medium.

As explained heretofore, the invention also relates to compositions comprising the gram positive bacterium, preferably a lactic acid bacterium (LAB) or *Bifidobacterium*, as described herein or comprising the gram positive bacterium, preferably a lactic acid bacterium (LAB) or *Bifidobacterium*, for use as described herein. Such composition may be a pharmaceutical composition. In a further embodiment, the invention relates to a composition or a pharmaceutical composition for use in treatment or for use as a medicament, a nutraceutical, a medical food, a functional food, a probiotic composition, a food additive or a starter culture. In yet another embodiment, the invention relates to the use of such composition or pharmaceutical composition as a medicament, nutraceutical, medical food, functional food, probiotic, food additive, starter culture, or for the preparation of a medicament, nutraceutical, medical food, functional food, probiotic composition, food additive, starter culture.

As used herein, the medicinal compositions as described herein, such as pharmaceutical formulation, nutraceutical, medical or functional food or probiotic, preferably comprises a therapeutically effective amount of the gram positive bacterium, preferably a lactic acid bacterium (LAB) or *Bifidobacterium*, of the invention and a pharmaceutically acceptable carrier, i.e., one or more pharmaceutically acceptable carrier substances and/or additives, e.g., buffers, carriers, excipients, stabilisers, etc. The term "pharmaceutically acceptable" as used herein is consistent with the art and means compatible with the other ingredients of a pharmaceutical composition and not deleterious to the recipient thereof.

In an embodiment, the pharmaceutical composition comprises a therapeutically effective amount of the gram positive bacterium, preferably a lactic acid bacterium (LAB) or *Bifidobacterium*, as described herein. The term "therapeutically effective amount" refers to an amount of a therapeutic substance or composition effective to treat a disease or disorder in a subject, e.g., human or animal, i.e., to obtain a desired local or systemic effect and performance. By means of example, a therapeutically effective amount of bacteria may comprise at least 1 bacterium, or at least 10 bacteria, or at least $10^2$ bacteria, or at least $10^3$ bacteria, or at least $10^4$ bacteria, or at least $10^5$ bacteria, or at least $10^6$ bacteria, or at least $10^7$ bacteria, or at least $10^8$ bacteria, or at least $10^9$, or at least $10^{10}$, or at least $10^{11}$, or at least $10^{12}$, or at least $10^{13}$, or at least $10^{14}$, or at least $10^{15}$, or more host cells, e.g., bacteria, e.g., in a single or repeated dose. The gram positive bacterium, preferably a lactic acid bacterium (LAB) or *Bifidobacterium*, of the present invention may be administered alone or in combination with one or more active compounds. The latter can be administered before, after or simultaneously with the administration of the gram positive bacterium, preferably a lactic acid bacterium (LAB) or *Bifidobacterium*, according to the invention.

Preferably the gram positive bacterium, preferably a lactic acid bacterium (LAB) or *Bifidobacterium*, as described herein or composition comprising these gram positive bacterium, preferably a lactic acid bacterium (LAB) or *Bifidobacterium*, is provided in a unit dosage form, for example a tablet, capsule, enema or metered aerosol dose, so that a single dose is administered to the subject, e.g. a human or animal patient.

The active ingredients may be administered from 1 to 6 times a day, sufficient to exhibit the desired activity. These daily doses can be given as a single dose once daily, or can be given as two or more smaller doses at the same or different times of the day which in total give the specified daily dose. Preferably, the active ingredient is administered once or twice a day. For instance, one dose could be taken in the morning and one later in the day.

In all aspects of the invention, the daily maintenance dose can be given for a period clinically desirable in the patient, for example from 1 day up to several years (e.g. for the mammal's entire remaining life); for example from about (2 or 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Other constituents of the liquid formulations may include preservatives, inorganic salts, acids, bases, buffers, nutrients, vitamins, or other pharmaceuticals.

The human or animal subjects as taught herein may refer to human or animal in need of therapy or treatment, comprising administering to the said human or animal a therapeutically effective amount of gram positive bacterium, preferably a lactic acid bacterium (LAB) or *Bifidobacterium*, as taught herein. The animal may preferably be a warm-blooded animal, more preferably a vertebrate, even more preferably a mammal, such as, e.g., domestic animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Generally, the term "subject" or "patient" may be used interchangeably and particularly refer to animals, preferably warm-blooded animals, more preferably vertebrates, even more preferably mammals, still more preferably primates, and specifically includes human patients and non-human animals, mammals and primates. Preferred patients may be human subjects.

Further non-limiting examples of the types of diseases treatable in humans or animals by delivery of gram positive bacterium, preferably a lactic acid bacterium (LAB) or *Bifidobacterium*, as described herein, optionally expressing prophylactic and/or therapeutic peptides, polypeptides or proteins, include, but are not limited to, e.g., inflammatory bowel diseases including Crohn's disease and ulcerative colitis (treatable with, e.g., IL-Ira or IL-10 or IL-27 or trefoil peptides); autoimmune diseases, including but not limited to type-1 diabetes, psoriasis, rheumatoid arthritis, lupus erythematosus (treatable with, e.g., IL-Ira or IL-10 or IL-27 or the relevant auto-antigen); allergic diseases including but not limited to asthma, food allergies, (treatable with the relevant allergen); celiac disease (treatable with gluten allergens and/or IL-27); neurological disorders including, but not limited to Alzheimer's disease, Parkinson's disease and amyotrophic lateral sclerosis (treatable with, e.g., brain devated neurotropic factor and ciliary neurotropic factor); cancer (treatable with, e.g., IL-1, colony stimulating factors or interferon-W); osteoporosis (treatable with, e.g., transforming growth factor f3); diabetes (treatable with, e.g., insulin); cardiovascular disease (treatable with, e.g., tissue plasminogen activator); atherosclerosis (treatable with, e.g., cytokines and cytokine antagonists); hemophilia (treatable with, e.g., clotting factors); degenerative liver disease (treatable with, e.g., hepatocyte growth factor or interferon a); pulmonary diseases such as cystic fibrosis (treatable with, e.g., alpha antitrypsin); obesity; pathogen infections, e.g., viral or bacterial infections (treatable with any number of the above-mentioned compositions or antigens); etc.

The gram positive bacterium, preferably a lactic acid bacterium (LAB) or *Bifidobacterium*, according to the invention can also be used to treat infectious diseases. In an embodiment, passive immunization against *Clostridium* associated disease, preferably *Clostridium dificile* associated disease (CDAD), with toxin-neutralizing antibodies locally produced and secreted via the gram positive bacterium, preferably a lactic acid bacterium (LAB) or *Bifidobacterium*, according to the invention can be obtained. CDAD is mediated by two exotoxins, toxin A (enterotoxin; see for instance Genbank NC_009089.1, region: 795843.803975 for DNA sequence or YP_001087137.1 for protein sequence) and toxin B (cytotoxin; see for instance Genbank NC_009089.1, region: 787393.794493 for DNA sequence or YP_001087135.1 for protein sequence). Both are highmolecular-mass proteins that bind to the surface of intestinal epithelial cells, where they are internalized and catalyze the glucosylation of cytoplasmic rho proteins, leading to cell death, inflammation and diarrhea. They have also been implicated in promoting *C. difficile* virulence, colonization, and neutrophil chemotaxis and activation. The bacteria itself is not invasive and does not cause tissue damage. By neutralizing the *C. difficile* toxins with antibodies, the pathogenic mechanism of the pathogen is blocked, its ability to thrive in the gut may be diminished, and the impact on the microbial ecology could be minimized, allowing recovery of the normal microflora. The medical advantage of this approach could include more rapid recovery, fewer relapses, and relief from selective pressure for antibiotic resistance in normal gut flora. Accordingly, in a preferred embodiment, the gram positive bacterium, preferably a lactic acid bacterium (LAB) or *Bifidobacterium*, as described herein further contain, express, produce, and/or secrete neutralizing antibodies against *Clostridium*, preferably *Clostridium dificile*, toxin A and/or toxin B, wherein each of these toxins preferably has the sequence as indicated above. The skilled reader will understand that besides full length antibodies, various functional fragments or modified or variant antibodies may be used, as described herein elsewhere.

The skilled reader shall appreciate that the herein specifically recited diseases are only exemplary and their recitation is in no way intended to confine the use of the gram positive bacterium, preferably a lactic acid bacterium (LAB) or *Bifidobacterium*, as taught herein, to these particular diseases. Instead, a skilled reader understands that the gram positive bacterium, preferably a lactic acid bacterium (LAB) or *Bifidobacterium*, disclosed herein can be used to express in principle any expression products, preferably polypeptides, of interest, which may be of therapeutic relevance in not only the recited ones but also in various further diseases or conditions of humans and animals. Consequently, once a suitable expression product, preferably a polypeptide, e.g., an antigen and/or a prophylactically and/or therapeutically gene product, polypeptide or protein, has been chosen or determined for a given ailment, a skilled person would be able to achieve its expression, isolation and/or delivery using the present reagents.

The gram positive bacterium, preferably a lactic acid bacterium (LAB) or *Bifidobacterium*, of the invention can be suspended in a pharmaceutical formulation for administration to the human or animal having the disease to be treated. Such pharmaceutical formulations include but are not limited to live host cells and a medium suitable for administration. The recombinant host cells may be lyophilized in the presence of common excipients such as lactose, other sugars, alkaline and/or alkali earth stearate, carbonate and/or sulphate (for example, magnesium stearate, sodium carbonate and sodium sulphate), kaolin, silica, flavorants and aromas.

The gram positive bacterium, preferably a lactic acid bacterium (LAB) or *Bifidobacterium*, according to the invention so-lyophilized may be prepared in the form of capsules, tablets, granulates and powders, each of which may be administered by the oral route.

Alternatively, some gram positive bacterium, preferably a lactic acid bacterium (LAB) or *Bifidobacterium*, may be prepared as aqueous suspensions in suitable media, or lyophilized bacteria may be suspended in a suitable medium just prior to use, such medium including the excipients referred to herein and other excipients such as glucose, glycine and sodium saccharinate.

For oral administration, gastroresistant oral dosage forms may be formulated, which dosage forms may also include compounds providing controlled release of the gram positive bacterium, preferably a lactic acid bacterium (LAB) or *Bifidobacterium*, and thereby provide controlled release of the desired protein encoded therein. For example, the oral dosage form (including tablets, pellets, granulates, powders) may be coated with a thin layer of excipient (usually polymers, cellulosic derivatives and/or lipophilic materials) that resists dissolution or disruption in the stomach, but not in the intestine, thereby allowing transit through the stomach in favour of disintegration, dissolution and absorption in the intestine.

The oral dosage form may be designed to allow slow release of the gram positive bacterium, preferably a lactic acid bacterium (LAB) or *Bifidobacterium*, (and optionally of the therapeutic and/or phrophylactice gene product thereof), for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990, Pharmaceutical dosage forms and drug delivery systems, 5th edition, William and Wilkins); Chien 1992, Novel drug delivery system, 2nd edition, M. Dekker); Prescott et al. (1989, Novel drug delivery, J. Wiley & Sons); Cazzaniga et al., (1994, Oral delayed release system for colonic specific delivery, Int. J. Pharm.i08:7').

Preferably, an enema formulation may be used for rectal administration. The term "enema" is used to cover liquid preparations intended for rectal use. The enema may be usually supplied in single-dose containers and contains one or more active substances dissolved or dispersed in water, glycerol or macrogols or other suitable solvents.

A preferred embodiment of invention provides an enteric coated capsule comprising stabilized freeze-dried, dried, or spray-dried viable gram positive bacterium, preferably a lactic acid bacterium (LAB) or *Bifidobacterium*, as described herein characterized in that the viable gram positive bacterium, preferably a lactic acid bacterium (LAB) or *Bifidobacterium*, are stabilized using a non-hygroscopic agent. As used herein a non-hygroscopic agent is meant to include any excipient typically used in the formulation of a pharmaceutical composition and wherein said agent exhibits an equilibrium moisture uptake at ambient 40% RH of not more than about 8 wt %, preferably not more than about wt 7%, and more preferably not more than about 6 wt %, for example about 1 wt % to about 5 wt %, more in particular less or equal to 2 wt %. The non-hygroscopic agent can be a polyol such as for example mannitol, maltitol, isomalt (polyol sugar) or a phosphate salt such as for example anhydrous dicalcium phosphate dibasic calcium phosphate, calcium hydrogen phosphate, or for example a sugar such as sucrose.

The capsule used in the aforementioned formulation is typically selected from the group consisting of a gelatin capsule, a starch capsule, a hydroxypropylmethylcellulose (HPMC) capsule and the like; in particular a HPMC capsule. For the intestinal delivery of viable bacteria, the enteric-coated capsules of the present invention should be stable at low pH (up to pH 5.5) and have an accelerated dissolution profile at higher pH (above pH 5.5). The optimal release is realized when the capsules desintegrate at a pH of about 6.8 within 1 hour. Thus, in a further embodiment of the present invention the capsules are coated with an enteric polymer to provide an enteric coated capsule that is stable at a pH up to 5.5 and that is soluble at a pH above 5.5; in particular at a pH above 6.0; more in particular with a fast dissolution profile at a pH of about 6.8.

The enteric polymer used for the enteric coating typically consists of a film-formable polymeric substance, which is soluble at a pH above 5.5, in particular at a pH above 6.0. Film-formable polymers useful in the different embodiments of the present invention are usually selected from the group consisting of a cellulose derivative, an acrylic copolymer, a maleic copolymer, a polyvinyl derivative, shellac and the like; in particular an acrylic copolymer selected from the group consisting of styrene-acrylic acid copolymer, methyl acrylate-acrylic acid copolymer, methyl acrylate-methacrylic acid copolymer, butyl acrylate-styrene-acrylic acid copolymer, methacrylic acid-methyl methacrylate copolymer such as Eudragit L100, Eudragit S or Eudragit S100 (each being trade name, commercially available from Röhm Pharma, Germany), methacrylic acid-ethyl acrylate copolymer such as Eudragit L100-55 (trade name, commercially available from Röhm Pharma, Germany), methyl acrylate-methacrylic acid-octyl acrylate copolymer, and the like; more in particular the film-formable polymer consists of methacrylic acid-methyl methacrylate copolymer.

Also a combination of different stabilizing compounds (cryoprotectants) is added to the bacterial biomass before drying, spray-drying, or freeze-drying. This combination of stabilizing compounds, comprising a starch hydrolysate and a glutamic acid salt and/or a polyol, results in improved survival and stability of dried, spray-dried, or freeze-dried gram positive bacterium, preferably a lactic acid bacterium (LAB) or *Bifidobacterium*.

The formulations and capsules as described herein can be used as a medicament, nutraceutical, food additive, functional food, medical food, starter culture and/or probiotic composition.

Thus, according the invention, in a preferred embodiment, gram positive bacterium, preferably a lactic acid bacterium (LAB) or *Bifidobacterium*, as described herein, or the (pharmaceutical) compositions comprising these gram positive bacterium, preferably a lactic acid bacterium (LAB) or *Bifidobacterium*, may be administered to the animal or human via mucosal, e.g., an oral, nasal, rectal, vaginal or bronchial route by any one of the state-of-the art formulations applicable to the specific route. Dosages of gram positive bacterium, preferably a lactic acid bacterium (LAB) or *Bifidobacterium*, for administration will vary depending upon any number of factors including the type of bacteria and the gene encoded thereby, the type and severity of the disease to be treated and the route of administration to be used. Thus, precise dosages cannot be defined for each and every embodiment of the invention, but will be readily apparent to those skilled in the art once armed with the present invention. The dosage could be anyhow determined on a case by case way by measuring the serum level concentrations of the therapeutic and/or prophylactic protein after administration of predetermined numbers of cells, using well known methods, such as those known as ELISA or Biacore (See examples). The analysis of the kinetic profile and half life of the delivered recombinant protein provides sufficient information to allow the determination of an effective dosage range for the gram positive bacterium, preferably a lactic acid bacterium (LAB) or *Bifidobacterium*.

In an embodiment, when the gram positive bacterium, preferably a lactic acid bacterium (LAB) or *Bifidobacterium*, express an antigen, the invention may thus also provide a vaccine. Preferably, the antigen may be capable of eliciting an immune response in and used as a vaccine in a human or animal. The term "vaccine" identifies a pharmaceutically acceptable composition that, when administered in an effective amount to an animal or human subject is capable of inducing antibodies to an immunogen comprised in the vaccine and/or elicits protective immunity in the subject. The vaccine of the invention would comprise the gram positive bacterium, preferably a lactic acid bacterium (LAB) or *Bifidobacterium*, as taught herein, optionally transformed with the nucleic acids or vectors encoding the antigen and further optionally an excipient. Such vaccines may also comprise an adjuvant, i.e., a compound or composition that enhances the immune response to an antigen. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful pharmaceutically acceptable human adjuvants such as BCG (bacille Calmetle-Guerin) and *Corynebacterium parvum*.

In an aspect, the invention relates to a method for treatment or to a therapy, comprising administering the gram positive bacterium, preferably a lactic acid bacterium (LAB) or *Bifidobacterium*, or compositions, preferably a therapeutic and/or prophylactic pharmaceutical composition to an individual in need thereof.

As described above, the composition comprising the gram positive bacterium, preferably a lactic acid bacterium (LAB) or *Bifidobacterium*, according to the invention may be a starter culture, a probiotic composition, or a food additive. Accordingly, the invention in an aspect relates to a starter culture, a probiotic composition, or a food additive comprising the gram positive bacterium, preferably a lactic acid bacterium (LAB) or *Bifidobacterium*, as described herein.

A starter culture may be, e.g., a liquid culture, liquid pressed culture, frozen or dried form, including, e.g., dried, freeze-dried form and spray/fluid bed dried form, or frozen or freeze-dried concentrated. Accordingly, in and embodiment, the invention relates to a starter culture as described herein, which is dried, spray-dried, frozen or freeze-dried. The culture may be packed in vacuum, or under an atmosphere of, e.g., $N_2$, $CO_2$ and the like. For example, a starter culture may be produced and distributed in sealed enclosures, preferably non-pyrogenic, which can be made of a rigid, non-flexible or flexible suitable plastic or other material, to the fermentation place and may be either added to organic material to be fermented, or optionally first cultivated in a separate starter medium to obtain a high density culture.

A starter culture may also contain, in addition to the gram positive bacterium, preferably a lactic acid bacterium (LAB) or *Bifidobacterium*, according to the invention, buffering agents and growth stimulating nutrients (e.g., an assimilable carbohydrate or a nitrogen source), or preservatives (e.g., cryoprotective compounds) or other carriers, if desired, such as milk powder or sugars.

A starter culture may be a pure culture, i.e., may contain a biomass of one single isolate of gram positive bacterium, preferably a lactic acid bacterium (LAB) or *Bifidobacterium*, according to the invention, i.e. a clone originating in principle from one cell. In another embodiment, a starter culture may be a co-culture, i.e., may comprise more than one strain of gram positive bacterium, preferably a lactic acid bacterium (LAB) or *Bifidobacterium*, of the invention, optionally further comprising additional microorganisms such as bacteria or yeasts.

It may be preferred that a starter culture or a high density culture contains at least $10^2$ colony forming units (CFU) of one or more gram positive bacterium, preferably a lactic acid bacterium (LAB) or *Bifidobacterium*, of the invention, such as at least $10^3$ CFU/g, at least $10^4$ CFU/g, e.g., at least $10^5$ CFU/g, at least $10^6$ CFU/g, e.g., at least $10^7$ CFU/g, at least $10^8$ CFU/g, e.g., at least $10^9$ CFU/g, at least $10^{10}$ CFU/g, e.g., at least $10^{11}$ CFU/g, at least $10^{12}$ CFU/g, or at least $10^{13}$ CFU/g.

Typically, a starter culture or a high density culture may be added to a starter medium or to organic material or substrate to be fermented in a concentration of viable cells of one or more bacterial strains (and optionally of one or more yeast strains) which is at least $10^2$ (CFU) of one or more bacterial strains (and optionally of one or more yeast strains) of the invention, such as at least $10^3$ CFU/g, at least $10^4$ CFU/g, e.g., at least $10^5$ CFU/g, at least $10^6$ CFU/g, e.g., at least $10^7$ CFU/g, at least $10^8$ CFU/g, e.g., at least $10^9$ CFU/g, at least $10^{10}$ CFU/g, e.g., at least $10^{11}$ CFU/g, at least $10^{12}$ CFU/g, or at least $10^{13}$ CFU/g of the organic material, medium or substrate.

In an embodiment, the invention relates to a starter culture as defined herein for the preparation of a food product or relates to a food additive or a probiotic composition, comprising a gram positive bacterium, preferably a lactic acid bacterium (LAB) or *Bifidobacterium*, lacking trehalose 6-phosphate pohosphorylase (TrePP) activity. In a preferred embodiment the gene encoding endogenous TrePP has been partially or completely deleted, disrupted or inactivated such as being incapable of producing functional trePP gene product, as described herein elsewhere. In a further embodiment, the gram positive bacterium, preferably a lactic acid bacterium (LAB) or *Bifidobacterium*, in the starter culture, the probiotic composition, or the food additive does not contain functional heterologous trehalose 6-phosphate phosphatase (e.g. otsB) and/or a functional heterologous trehalose 6-phosphate synthase (e.g. otsA), as described herein elsewhere. In yet a further embodiment, the gram positive bacterium, preferably a lactic acid bacterium (LAB) or *Bifidobacterium*, in the starter culture, probiotic composition, or food additive as described herein does not contain a functional heterologous gene involved in the metabolism (either catabolic or anabolic) of trehalose or trehalose 6-phosphate. Such genes encompass, without limitation trehalase, trehalose phosphorylase, and trehalose 6-phosphate hydrolase.

In another embodiment, the invention relates to a starter culture, probiotic composition, or food additive as defined herein, wherein the gram positive bacterium, preferably a lactic acid bacterium (LAB) or *Bifidobacterium*, lacks cellobiose-specific PTS system IIC component (ptcC) activity. In a preferred embodiment the gene encoding endogenous the gene encoding endogenous ptcC has been partially or completely deleted, disrupted or inactivated such as being incapable of producing functional ptcC gene product, as described herein elsewhere.

In a further embodiment, the invention relates to a starter culture, probiotic composition, or food additive as described herein, wherein the gram positive bacterium, preferably a lactic acid bacterium (LAB) or *Bifidobacterium*, overexpresses, preferably constitutively overexpresses, one or more genes encoding a trehalose transporter, preferably an endogenous trehalose transporter, as described herein elsewhere.

In yet another embodiment, the invention relates to a starter culture, probiotic composition, or food additive as described herein, wherein the gram positive bacterium, preferably a lactic acid bacterium (LAB) or *Bifidobacterium*, expresses one or more heterologous gene product, preferably one or more prophylactic and/or therapeutic gene product, as described herein elsewhere.

In an embodiment, the starter culture, probiotic composition, or food additive as described herein is dried, frozen, spray-dried or freeze-dried.

As indicated above, in an aspect, the invention relates to the use of the gram positive bacterium, preferably a lactic acid bacterium (LAB) or *Bifidobacterium*, as described herein for the preparation of a starter culture, preferably for use as a food additive or probiotic composition or for use in the preparation of a food product. In a further aspect, the invention relates to the use of a starter culture as a food additive, probiotic composition or for the preparation of a food product.

As used herein, the term "food additive" refers to gram positive bacterium, preferably a lactic acid bacterium (LAB) or *Bifidobacterium*, preferably formulated in a composition, which can be added to a human or animal food or feed, suitable for consumption without further modification or alternatively after further modification, such as complete or partial fermentation of the food or feed or the complete or partial fermentation of one or more components of the food or feed. By means of example, and without limitation, the gram positive bacterium, preferably a lactic acid bacterium (LAB) or *Bifidobacterium*, according to the invention, or the compositions according to the invention, such as the starter cultures described herein, may be used in the dairy industry, in particular for the preparation of fermented milk products, also known as cultured dairy foods, cultured dairy products, or cultured milk products. The fermentation process increases the shelf-life of the product, as well as adds to the taste and improves the digestibility of milk. Examples of food products referred to herein, include, but are not limited to cheese, yoghurt, sour cream, buttermilk, acidophilus milk, . . . .

In an aspect, the invention also relates to a method for preparing a medicament, a food additive, a probiotic composition, or a starter culture as defined herein, wherein said starter culture is preferably a starter culture for the preparation of a food product, comprising the steps of:

i) propagating gram positive bacterium, preferably a lactic acid bacterium (LAB) or *Bifidobacterium*, as defined herein in a medium comprising a substrate material capable of being fermented by said gram positive bacterium, preferably a lactic acid bacterium (LAB) or *Bifidobacterium*; and ii) formulating the so propagated gram positive bacterium, preferably a lactic acid bacterium (LAB) or *Bifidobacterium*, as a medicament, food additive, probiotic composition, or starter culture, respectively.

Methods for propagating gram positive bacterium, preferably a lactic acid bacterium (LAB) or *Bifidobacterium*, as well as media and substrates capable of being fermented by gram positive bacterium, preferably a lactic acid bacterium (LAB) or *Bifidobacterium*, are well known in the art. In an embodiment, the formulation as a medicament, food additive, probiotic composition, or starter culture comprises formulating as a liquid culture, liquid pressed culture, frozen or dried form, including, e.g., dried, freeze-dried form and spray/fluid bed dried form, or frozen or freeze-dried concentrated. Preferably, the formulation comprises drying, spray-drying, freezing or freeze-drying.

In a further aspect, the invention also relates to a method for preparing a food product, comprising the step of admixing the gram positive bacterium, preferably a lactic acid bacterium (LAB) or *Bifidobacterium*, as defined herein, the food additive as defined herein, the probiotic composition as defined herein, or the starter culture as defined herein with a substrate material capable of being fermented by said gram positive bacterium, preferably a lactic acid bacterium (LAB) or *Bifidobacterium*. The substrate material is typically a carbon source, preferably a carbohydrate or sugar. Carbohydrates capable of being fermented by gram positive bacterium, preferably a lactic acid bacterium (LAB) or *Bifidobacterium*, include, but are not limited to monosaccharides or disaccharides such as glucose, fructose, galactose, sucrose, lactose, maltose, trehalose, cellobiose, . . . . In an embodiment, the method for preparing a food product comprises the steps of:

i) providing the gram positive bacterium, preferably a lactic acid bacterium (LAB) or *Bifidobacterium*, food additive, probiotic composition, or the starter culture as described herein;
ii) providing a substrate material or a composition, preferably a non-toxic or an edible composition, comprising a substrate material which is capable of being fermented by said gram positive bacterium, preferably a lactic acid bacterium (LAB) or *Bifidobacterium*;
iii) admixing the gram positive bacterium, preferably a lactic acid bacterium (LAB) or *Bifidobacterium*, as defined herein, food additive as defined herein, the probiotic composition as defined herein, or the starter culture as defined herein with the substrate material or composition
iv) optionally propagating said gram positive bacterium, preferably a lactic acid bacterium (LAB) or *Bifidobacterium*, and/or fermenting said substrate material or composition with said gram positive bacterium, preferably a lactic acid bacterium (LAB) or *Bifidobacterium*.

In an aspect, the invention also relates to a food product directly or indirectly obtained or obtainable by the herein described methods.

As described before, the gram positive bacterium, preferably a lactic acid bacterium (LAB) or *Bifidobacterium*, according to the invention advantageously accumulate trehalose intracellularly. Accordingly, in an aspect, the invention also relates to a method for internally accumulating trehalose in a gram positive bacterium, preferably a lactic acid bacterium (LAB) or *Bifidobacterium*, such as trehalose being present in the growth medium, or externally or exogenously added trehalose, comprising the step of propagating gram positive bacterium, preferably a lactic acid bacterium (LAB) or *Bifidobacterium*, according to the invention in a medium comprising a substrate material capable of being fermented by said gram positive bacterium, preferably a lactic acid bacterium (LAB) or *Bifidobacterium*. In an embodiment, the method for internally accumulating trehalose in a gram positive bacterium, preferably a lactic acid bacterium (LAB) or *Bifidobacterium*, comprises the steps of:

i) providing the gram positive bacterium, preferably a lactic acid bacterium (LAB) or *Bifidobacterium*, or the starter culture as described herein;
ii) providing a substrate material or a composition, preferably a non-toxic or an edible composition, comprising a substrate material which is capable of being fermented by said gram positive bacterium, preferably a lactic acid bacterium (LAB) or *Bifidobacterium*;
iii) admixing the gram positive bacterium, preferably a lactic acid bacterium (LAB) or *Bifidobacterium*, as defined herein, or the starter culture as defined herein with the substrate material or composition
iv) optionally propagating said gram positive bacterium, preferably a lactic acid bacterium (LAB) or *Bifidobacterium*, and/or fermenting said substrate material or composition with said gram positive bacterium, preferably a lactic acid bacterium (LAB) or *Bifidobacterium*.

The gram positive bacterium, preferably a lactic acid bacterium (LAB) or *Bifidobacterium*, according to the invention advantageously show an improved resistance to stress as well as improved manufacturing, processing and/or storage characteristics. Accordingly, in an aspect, the invention relates to a method for improving stress resistance or manufacturing, processing and/or storage characteristics of a gram positive bacterium, preferably a lactic acid bacterium (LAB) or *Bifidobacterium*, comprising modifying the gram positive bacterium, preferably a lactic acid bacterium (LAB) or *Bifidobacterium*, such as to lack TrePP activity. In an embodiment, the gene encoding endogenous TrePP has been partially or completely deleted, disrupted or inactivated such as being incapable of producing functional trePP gene product. Preferably the stress resistance or manufacturing, processing and/or storage characteristics is one or more stress resistance or manufacturing, processing and/or storage characteristics selected from the group comprising resistance to acid conditions, resistance to bile salts, resistance to heat, resistance to salt, resistance to drying, spray-drying, freezing or freeze-drying, and osmotic resistance.

In an embodiment, the invention relates to any of the methods as described herein, wherein the gram positive bacterium, preferably a lactic acid bacterium (LAB) or *Bifidobacterium*, does not contain functional heterologous trehalose 6-phosphate phosphatase (e.g. otsB) and/or a functional heterologous trehalose 6-phosphate synthase (e.g. otsA), as described herein elsewhere. In yet a further embodiment, the invention relates to any of the methods as described herein, wherein the gram positive bacterium, preferably a lactic acid bacterium (LAB) or *Bifidobacterium*, does not contain a functional heterologous gene involved in the metabolism (either catabolic or anabolic) of trehalose or trehalose 6-phosphate. Such genes encompass, without limitation trehalase, trehalose phosphorylase, and trehalose 6-phosphate hydrolase.

In another embodiment, the invention relates any of the methods as described herein, wherein the gram positive bacterium, preferably a lactic acid bacterium (LAB) or *Bifidobacterium*, lacks cellobiose-specific PTS system IIC component (ptcC) activity. In a preferred embodiment the gene encoding endogenous the gene encoding endogenous ptcC has been partially or completely deleted, disrupted or inactivated such as being incapable of producing functional ptcC gene product, as described herein elsewhere.

In a further embodiment, the invention relates to any of the methods as described herein, wherein the gram positive bacterium, preferably a lactic acid bacterium (LAB) or *Bifidobacterium*, overexpresses, preferably constitutively overexpresses, one or more genes encoding a trehalose transporter, preferably an endogenous trehalose transporter, as described herein elsewhere.

In yet another embodiment, the invention relates to any of the methods as described herein, wherein the gram positive bacterium, preferably a lactic acid bacterium (LAB) or *Bifidobacterium*, expresses one or more heterologous gene product, preferably one or more prophylactic and/or therapeutic gene product, as described herein elsewhere.

In an embodiment, the invention relates to any of the methods as described herein, further comprising the step of drying, freezing, spray-drying, or freeze-drying the gram positive bacterium, preferably a lactic acid bacterium (LAB) or *Bifidobacterium*, medicament, food additive, probiotic composition, or starter culture.

The inventors have surprisingly found that the gram positive bacterium, preferably a lactic acid bacterium (LAB) or *Bifidobacterium*, according to the invention are capable of intracellularly accumulating trehalose without the addition of externally added trehalose. Advantageously, the gram positive bacterium, preferably a lactic acid bacterium (LAB) or *Bifidobacterium*, according to the invention can be propagated in medium optionally even without externally added trehalose but still accumulate trehalose internally. Accordingly, in an embodiment, the invention relates to the methods as described herein, comprising the step of maintaining or propagating the gram positive bacterium, preferably a lactic acid bacterium (LAB) or *Bifidobacterium*, as described herein in a medium lacking or substantially lacking trehalose, or a medium lacking or substantially lacking externally or exogenously added trehalose. Advantageously, such medium can comprise another fermentable carbon source, such as, but without limitation maltose and/or glucose.

Accordingly, in an embodiment, the invention relates to any of the methods as described herein, wherein the gram positive bacterium, preferably a lactic acid bacterium (LAB) or *Bifidobacterium*, according to the invention are maintained or propagated in a medium comprising a substrate material capable of being fermented by said gram positive bacterium, preferably a lactic acid bacterium (LAB) or *Bifidobacterium*, wherein said substrate material comprises less (such as suboptimal), does not comprise or substantially does not comprise trehalose. Alternatively, the invention relates to any of the methods as described herein, wherein the gram positive bacterium, preferably a lactic acid bacterium (LAB) or *Bifidobacterium*, according to the invention are maintained or propagated in a medium comprising a substrate material capable of being fermented by said gram positive bacterium, preferably a lactic acid bacterium (LAB) or *Bifidobacterium*, wherein said substrate material comprises maltose. In a preferred embodiment, the invention relates to any of the methods as described herein, wherein the gram positive bacterium, preferably a lactic acid bacterium (LAB) or *Bifidobacterium*, according to the invention are maintained or propagated in a medium comprising a substrate material capable of being fermented by said gram positive bacterium, preferably a lactic acid bacterium (LAB) or *Bifidobacterium*, wherein said substrate material comprises maltose and wherein said substrate material comprises less (such as suboptimal), does not comprise or substantially does not comprise trehalose.

As used herein, a medium comprising no or substantially no trehalose or no externally added or exogenous trehalose refers to a medium which does not contain trehalose or which only contains small quantities of trehalose. Preferably, the amount or concentration of trehalose in such medium is too low to allow for the bacteria to be able to use as a sole carbon source. In an embodiment, the medium contains less than 100 mM, preferably less than 50 mM, more preferably less than 25 mM, such as less than 15 mM, less than 10 mM, less than 5 mM, less than 2 mM, or less than 1 mM. In a further embodiment, the medium contains less than 2 w/w % or less than 2 v/w % trehalose, preferably less than 1 w/w % or less than 1 v/w % trehalose, more preferably less than 0.5 w/w % or less than 0.5 v/w % trehalose, such as less than 0.3, less than 0.2, less than 0.1, less than 0.05, or less than 0.01 w/w % or v/w % trehalose. In another embodiment, the medium contains less than 20% trehalose of the total amount of carbon source or fermentable carbohydrate, preferably less than 10%, more preferably less than 5%, such as less than 3%, less than 2%, or less than 1%.

In a further aspect, the invention relates to the use of the gram positive bacterium, preferably a lactic acid bacterium (LAB) or *Bifidobacterium*, as described herein to accumulate intracellular trehalose in said gram positive bacterium, preferably a lactic acid bacterium (LAB) or *Bifidobacterium*. In a preferred embodiment, the invention relates to the use of the gram positive bacterium, preferably a lactic acid bacterium (LAB) or *Bifidobacterium*, as described herein to accumulate intracellular trehalose in said gram positive bacterium, preferably a lactic acid bacterium (LAB) or *Bifidobacterium*, in the absence or substantial absence of trehalose. In another embodiment, the invention relates to the use of the gram positive bacterium, preferably a lactic acid bacterium (LAB) or *Bifidobacterium*, as described herein to accumulate intracellular trehalose in said gram positive bacterium, preferably a lactic acid bacterium (LAB) or *Bifidobacterium*, when maintained or propagated on maltose, preferably as the sole or substantially sole carbon source.

As described above, the gram positive bacterium, preferably a lactic acid bacterium (LAB) or *Bifidobacterium*, according to the invention show an improved resistance to a variety of environmental stresses as well as improved manufacturing, processing and/or storage characteristics. Accordingly, in an aspect, the invention relates to the use of the gram positive bacterium, preferably a lactic acid bacterium (LAB) or *Bifidobacterium*, as described herein to improve stress resistance or to improve manufacturing, processing and/or storage characteristics in said gram positive bacterium, preferably a lactic acid bacterium (LAB) or *Bifidobacterium*. In a further aspect, the invention relates to a method for improving stress resistance or for improving manufacturing, processing and/or storage characteristics in gram positive bacterium, preferably a lactic acid bacterium (LAB) or *Bifidobacterium*, comprising generating the gram positive bacterium, preferably a lactic acid bacterium (LAB) or *Bifidobacterium*, as described herein.

In an embodiment, the stress resistance is selected from the group comprising resistance to acid conditions, resistance to bile salts, heat resistance, resistance to salt, cold resistance, osmotic resistance, preferably selected from resistance to acid conditions or bile salts, more preferably resistance to bile salts. In another embodiment, the manufacturing, processing and/or storage characteristics are selected from the group comprising drying, freezing, freeze-drying, spray-drying or storage in medium, preferably freezing or freeze-drying, more preferably freeze-drying.

In another aspect, the invention relates to a gram positive bacterium, preferably a lactic acid bacterium (LAB) or *Bifidobacterium*, lacking TrePP activity and further displaying any one or preferably both of the following characteristics: (i) the grampositive bacterium lacks ptcC activity; (ii) the gram positive bacterium overexpresses, preferably constitutively overexpresses, one or more trehalose transporters. In an embodiment, the invention relates to a gram positive bacterium, preferably a lactic acid bacterium (LAB) or *Bifidobacterium*, lacking TrePP activity and lacking ptcC activity. In another embodiment, the invention relates to a gram positive bacterium, preferably a lactic acid bacterium (LAB) or *Bifidobacterium*, lacking TrePP activity and (constitutively) overexpressing one or more trehalose transporters. In yet another embodiment, the invention relates to a gram positive bacterium, preferably a lactic acid bacterium (LAB) or *Bifidobacterium*, lacking TrePP activity, lacking ptcC activity, and (constitutively) overexpressing one or more trehalose transporters. In a further embodiment, the invention relates to any of these gram positive bacterium, preferably a lactic acid bacterium (LAB) or *Bifidobacterium*, which do not contain functional heterologous trehalose 6-phosphate phosphatase and/or functional heterologous trehalose 6-phosphate synthase. In another embodiment, the invention relates to any of these gram positive bacterium, preferably a lactic acid bacterium (LAB) or *Bifidobacterium*, which contain functional heterologous trehalose 6-phosphate phosphatase and/or functional heterologous trehalose 6-phosphate synthase. In a further embodiment, the invention relates to any of these gram positive bacterium, preferably a lactic acid bacterium (LAB) or *Bifidobacterium*, containing one or more heterologous gene products, preferably prophylactic and/or therapeutic gene product(s), preferably not containing functional heterologous trehalose 6-phosphate phosphatase and/or functional heterologous trehalose 6-synthase.

The aspects and embodiments of the invention are further supported by the following non-limiting examples.

EXAMPLES

Figure 4:
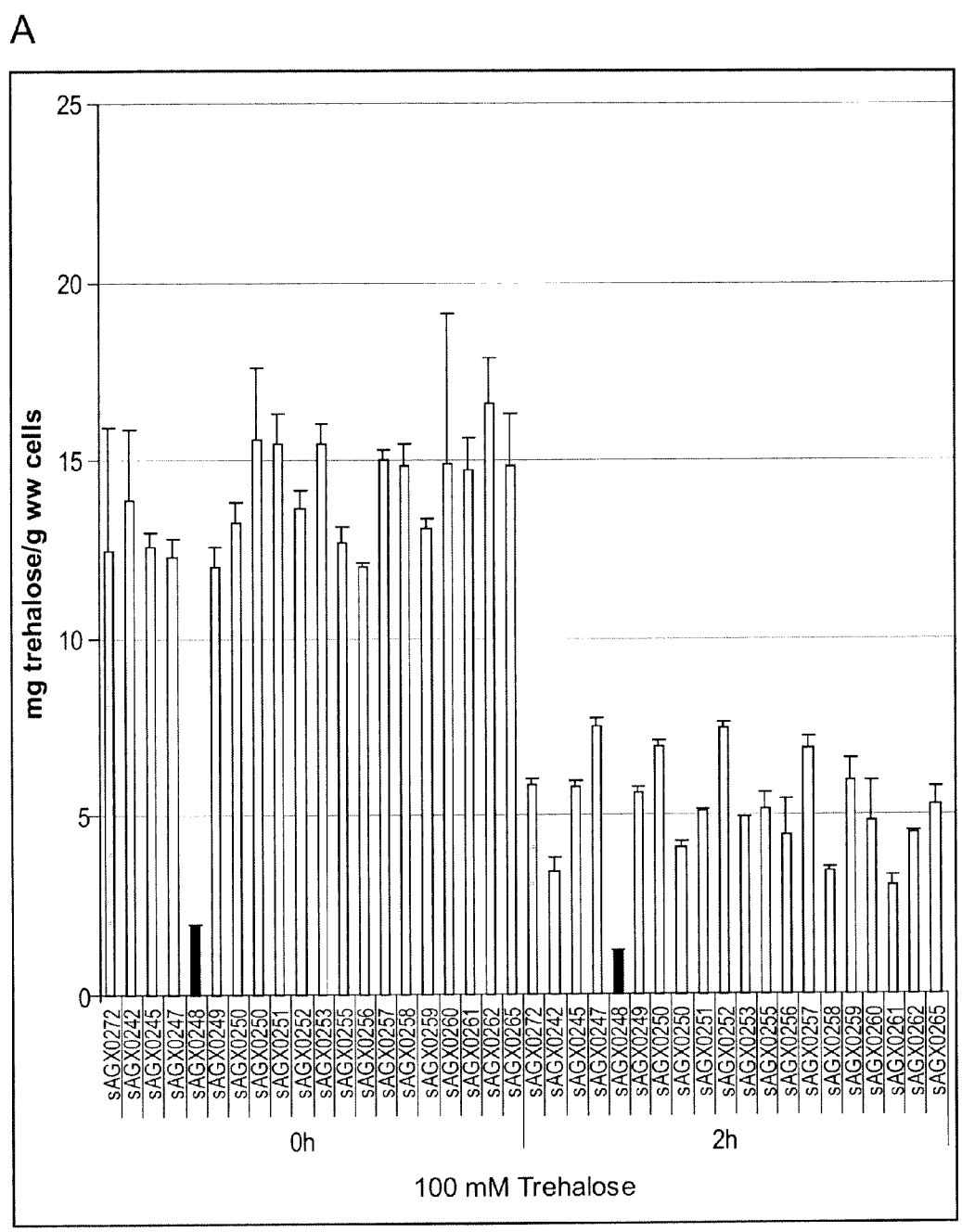
FIG. 4: Trehalose accumulation and release in various strains described in Table 2. Strains were supplemented with 100 mM (A) or 500 mM (B) trehalose.
Figure 4:
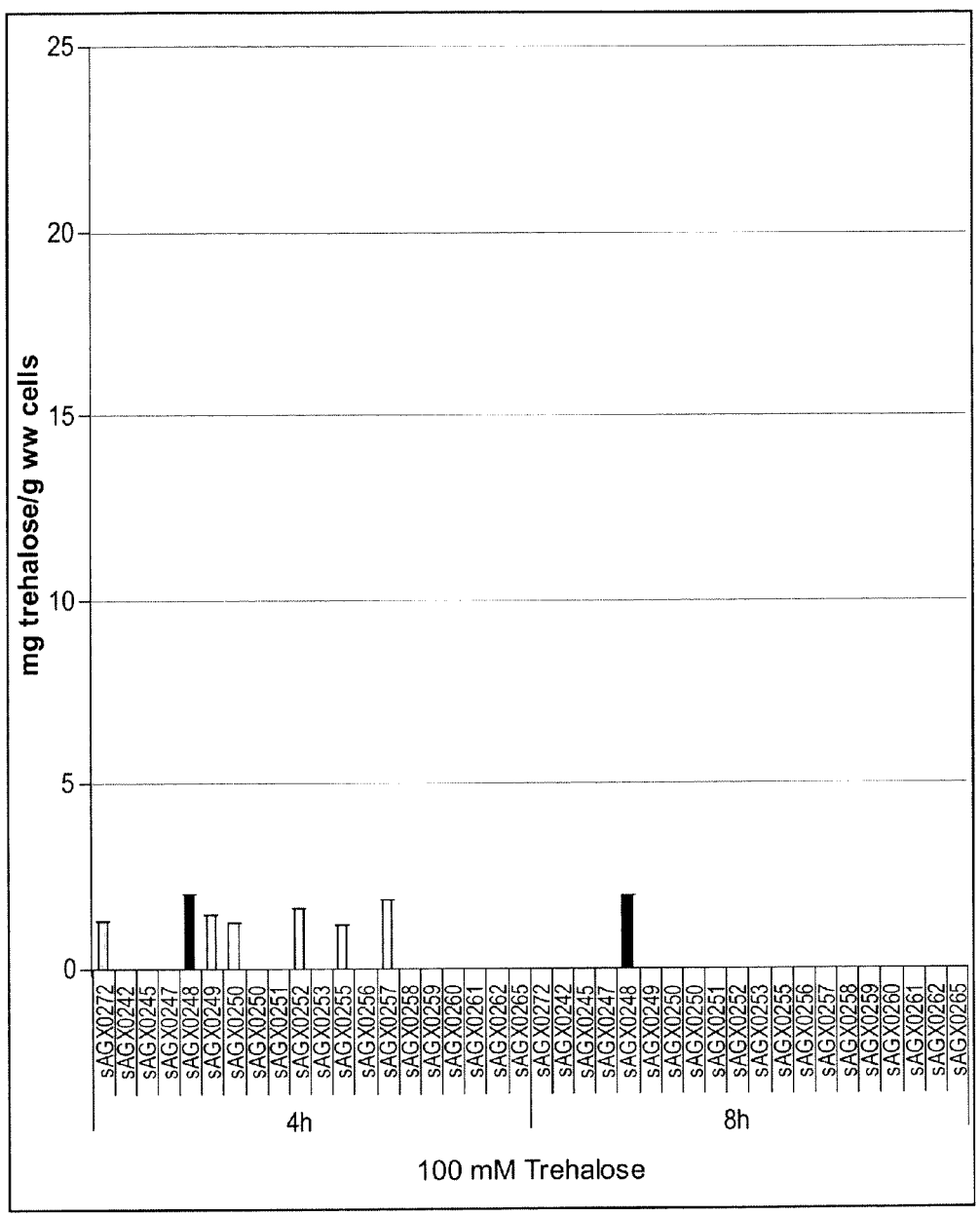
Figure 4:
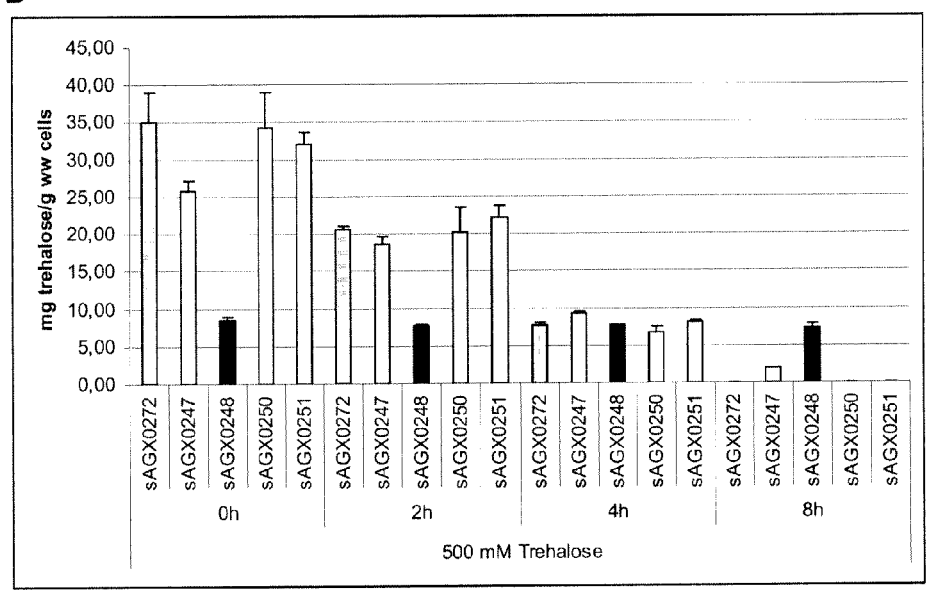

Table 1 provides an overview of genetic modifications in strains described herein, except for strains used in FIG. 4 which are given in Table 2.

Overview of genetic modifications in strains described herein. Indicated is a) the structure of the trehalose operon: whether the native trehalose operon promoter (Ptre) precedes the trehalose PTS transporters (Ptre>>PTS) and whether trePP was deleted (KO) or not (wild type; wt); b) structure of the ptcC gene: wild type (wt), inactivated (KO) by insertion of a stop codon or gene deletion; c) absence (−) or presence of functionally inactive (mutant) otsB or wild type otsB, either inserted at the thyA locus following the thyA promoter (PthyA>>otsB) or inserted as a second cistron following the usp45 gene (usp45>>otsB); d) structure of the thyA gene: wild type (wt) or inactivated (KO) by gene deletion or insertion of a cargo gene (gene replacement); e) absence (−) or nature and structure of uidA, hIL-10 or anti-TNF CDP870 cargo genes, inserted at the thyA locus under control of the hIIA promoter (PhIIA>>) or inserted downstream of the usp45 or gapB genes (usp45>>; gapB>>). All strains are derived from *L. lactis* MG1363.

TABLE 2

| Strain | Inactivated Gene | Inactivated Gene ID | Inactivated protein product |
| --- | --- | --- | --- |
| sAGX0241 | pmrB | 4799106 | multidrug resistance efflux pump |
| sAGX0242 | celB | 4796591 | cellobiose-specific PTS system IIC component |
| sAGX0245 | araJ | 4796972 | putative arabinose efflux permease |
| sAGX0246 | ptcB | 4797109 | cellobiose-specific PTS system IIB component |
| sAGX0247 | ptcA | 4798642 | cellobiose-specific PTS system IIA component |

TABLE 1

| strain | a) trehalose operon | | b) ptcC | c) otsB | d) thyA | e) Cargo |
| --- | --- | --- | --- | --- | --- | --- |
| | trehalose PTS I/II | TrePP | | | | |
| sAGX0037 | wt (Ptre>>PTS) | wt | wt | — | KO (gene replacement) | PhIIA>>hIL-10 (thyA locus) |
| sAGX0085 | wt (Ptre>>PTS) | wt | wt | — | KO (gene replacement) | PhIIA>>hTFF1 (thyA locus) |
| sAGX0137 | wt (Ptre>>PTS) | wt | wt | usp45>> mutant otsB | KO (gene replacement) | PhIIA>>hIL-10 (thyA locus) |
| sAGX0139 | wt (Ptre>>PTS) | wt | wt | usp45>>otsB | KO (gene replacement) | PhIIA>>hIL-10 (thyA locus) |
| sAGX0147 | wt (Ptre>>PTS) | KO | wt | usp45>> mutant otsB | KO (gene replacement) | PhIIA>>hIL-10 (thyA locus) |
| sAGX0148 | wt (Ptre>>PTS) | KO | wt | usp45>>otsB | KO (gene replacement) | PhIIA>>hIL-10 (thyA locus) |
| sAGX0167 | PhIIA>>PTS | KO | wt | usp45>>otsB | KO (gene replacement) | PhIIA>>hIL-10 (thyA locus) |
| sAGX0169 | wt (Ptre>>PTS) | KO | wt | — | KO (gene replacement) | PhIIA>>hTFF-1 (thyA locus) |
| sAGX0248 | wt (Ptre>>PTS) | KO | KO (stop codon) | — | wt | — |
| sAGX0272 | wt (Ptre>>PTS) | KO | wt | — | wt | — |
| sAGX0309 | PhIIA>>PTS | KO | wt | — | KO (gene deletion) | usp45>>CDP870 anti-TNF |
| sAGX0319 | KO | KO | wt | — | KO (gene deletion) | usp45>>CDP870 anti-TNF |
| sAGX0346 | PhIIA>>PTS | KO | KO (stop codon) | usp45>>otsB | KO (gene deletion) | — |
| sAGX0347 | PhIIA>>PTS | KO | KO (gene deletion) | usp45>>otsB | KO (gene deletion) | — |
| sAGX0354 | PhIIA>>PTS | KO | KO (stop codon) | usp45>>otsB | KO (gene deletion) | gapB>>CDP870 anti-TNF |

TABLE 2-continued

| Strain | Inactivated Gene | Inactivated Gene ID | Inactivated protein product |
|---|---|---|---|
| sAGX0248 | ptcC | 4796893 | cellobiose-specific PTS system IIC component |
| sAGX0249 | msmK | 4797024 | multiple sugar-binding transport ATP-binding protein |
| sAGX0250 | llmg_0453 | 4797778 | sucrose-specific PTS enzyme IIABC (tre operon) |
| sAGX0251 | llmg_0454 | 4797093 | beta-glucoside-specific PTS system IIABC component (tre operon) |
| sAGX0252 | llmg_0489 | 4796717 | sugar transport system permease protein |
| sAGX0253 | llmg_0490 | 4796719 | sugar transport system permease protein |
| sAGX0255 | malG | 4798664 | maltose ABC transporter permease protein malG |
| sAGX0256 | malF | 4798442 | maltose transport system permease protein malF |
| sAGX0257 | malE | 4798313 | maltose ABC transporter substrate binding protein |
| sAGX0258 | lplB | 4798767 | sugar ABC transporter substrate binding protein |
| sAGX0259 | lplC | 4796680 | sugar ABC transporter permease |
| sAGX0260 | lplA | 4797636 | sugar ABC transporter substrate-binding protein |
| sAGX0261 | bglP | 4797495 | PTS system, beta-glucosides specific enzyme IIABC |
| sAGX0262 | llmg_1104 | 4798113 | drug-export protein |
| sAGX0265 | tagG | 4798685 | teichoic acid ABC transporter permease protein |

Overview of strains constructed to identify the trehalose exit port. Strains were constructed that are deficient in trePP to allow trehalose accumulation and in which a selection of genes, taken from *L. lactis* COGs functional categories "Carbohydrate transport and metabolism" http://www.ncbi.nlm.nih.gov/sutils/cogtik.cgi?gi=20494&cog=G (from which gene and protein nomenclature was taken) are inactivated. The Gene ID of inactivated genes is indicated as well as the inactivated protein product.

Gene inactivation was performed by oligonucleotide directed recombineering, introducing in-frame stopcodons in the respective target genes. All strains are derived from *L. lactis* MG1363

EXAMPLE 1

Intracellular Trehalose Accumulation Following trePP Inactivation

Experimental

Strains were grown overnight (A) or for 24 hours (B) in 50 ml GM17T+500 mM trehalose at 30° C., cells were collected by centrifugation and trehalose content was determined: equivalents of 10 ml overnight culture were washed 3 times with 0.25 M carbonate buffer where after weight of the cell pellet (wet weight) was determined. Cells were lysed in 1 ml 0.25 M carbonate buffer using the lysing matrix B and the MP Fasprep-24 device at 6 m/s for 40 seconds (MP Biomedicals). Supernatant of the lysed cells was separated by centrifugation and heated for 30 minutes at 99° C. Cell debris was removed by centrifugation and the supernatant was assayed for trehalose concentration using a trehalose assay kit (K-TREH 010/10, Megazyme, Ireland). Briefly, trehalose in the samples is hydrolysed to D-glucose by trehalase, and the D-glucose released is phosphorylated by the enzyme hexokinase and adenosine-5' triphoshate (ATP) to glucose-6-phosphate with the simultaneous formation of adenosine-5' diphosphate (ADP). In the presence of the enzyme glucose-6-phosphate dehydrogenase, glucose-6-phosphate is oxidized by nicotinamide-adenine dinucleotide phosphate (NADP+) to gluconate-6-phosphate with the formation of reduced nicotinamide-adenine dinucleotide phosphate (NADPH). The amount of NADPH formed in this reaction is stoichiometric with the amount of D-glucose and thus with the amount of trehalose. It is the NADPH which is measured by the increase in absorbance at 340 nm (in comparison to the OD340 before the addition of threhalose). Trehalose values were calculated by use of a serial dilution of a trehalose standard and expressed as mg/g wet cell pellet weight (ww)

Results

Intracellular trehalose accumulation is possible following trePP inactivation, following otsB expression or a combination thereof, as indicated in FIG. 1. FIG. 1 (A) depicts trePP wild type strains (sAGX0037 and sAGX0137) do not accumulate trehalose. Inactivation of trePP in sAGX0137 (containing a non-functional mutant otsB), leading to sAGX0147, allows for the accumulation of trehalose. Insertion of wild type otsB sAGX0037, leading to sAGX0139, allows for the accumulation of trehalose. Combination of otsB and trePP KO leads to a moderate increase in trehalose accumulation (sAGX0148) which is greatly potentiated by the insertion of the strong constitutive PhllA promoter (which is disclosed in WO 2008/084115) in front of both phosphotransferase system (PTS) genes of the *L. lactis* trehalose operon (sAGX0167). FIG. 1 (B) shows that trePP wild type strain sAGX0085 cannot accumulate trehalose. Inactivation of trePP KO (sAGX0169) only allows for the accumulation of trehalose.

From FIG. 1 it is clear that trePP wild type strains do not accumulate trehalose. Gene disruption (gene deletion but also point mutation) of trePP allows intracellular accumulation of exogenous trehalose. In strain sAGX0147 a non-functional otsB mutant gene is present, while strains sAGX0169, sAGX0309 and sAGX0319 cary no otsB genes. Strain sAGX0169 carries, except for the hTFF1 cargo gene present in the thyA locus, no other genetic alteration than the disruption of trePP. Trehalose accumulation in a trePP KO strain is unexpected as one would deem, according to the prior art, this to be critically dependent on a trehalose-6-phosphate phosphatase (otsB or analogue). Such function has not been described in *L. lactis* and would not be expected to be present as it would counteract the metabolism of trehalose by *L. lactis* by converting trehalose-6-phosphate to the inert intracellular trehalose. We here observe that, unexpectedly, this function is present in *L. lactis*. trePP KO can be performed by gene deletion, as was done here or by the establishment of a stop codon or frame shift mutation or a promoter mutation or the identification of a spontaneous non-functional trePP mutant. Trehalose accumulation is possible when otsB is present as such (sAGX0139) or combined with trePP KO (sAGX0148) or even further combined with an insertion of the strong constitutive promoter PhllA positioned in front of both phosphotransferase system (PTS) genes (PhllA>>trePTC) of the *L. lactis* trehalose operon (sAGX0167). The preferred position of otsB, as it is used here, is as a second cistron behind the indigenous usp45 gene in a configuration as described European patent applications with application numbers 11168495.7 and 11173588.2 (usp45>>rpmD>>otsB, wherein rpmD is the intergenic region preceding rpmD).

EXAMPLE 2

The Accumulation of Exogenous Trehalose Provides Protection Towards Bile Lysis Experimental Strains were grown overnight in 50 ml GM17T or GM17T+500 mM trehalose at 30° C., cells were collected by centrifugation and resuspended in 25 ml 0.9% NaCl. Samples were taken and CFU were determined by plating appropriate dilutions (initial) At T0, 25 ml 1% oxgal in 0.9% NaCl was added and cell suspensions were incubated for 8 h at 37° C. Samples were taken at T0, 1, 2, 4, 6 and 8 h. CFU were determined by plating appropriate dilutions (FIG. 2 A), trehalose content was determined (FIG. 2 B) essentially as described in Example 1

Results

Intracellular trehalose protects against bile lysis and the loss of intracellular trehalose coincides with decreased resistance to bile lysis. Therefore, leakage of trehalose is problematic for long term stability in bile.

Figure 2:
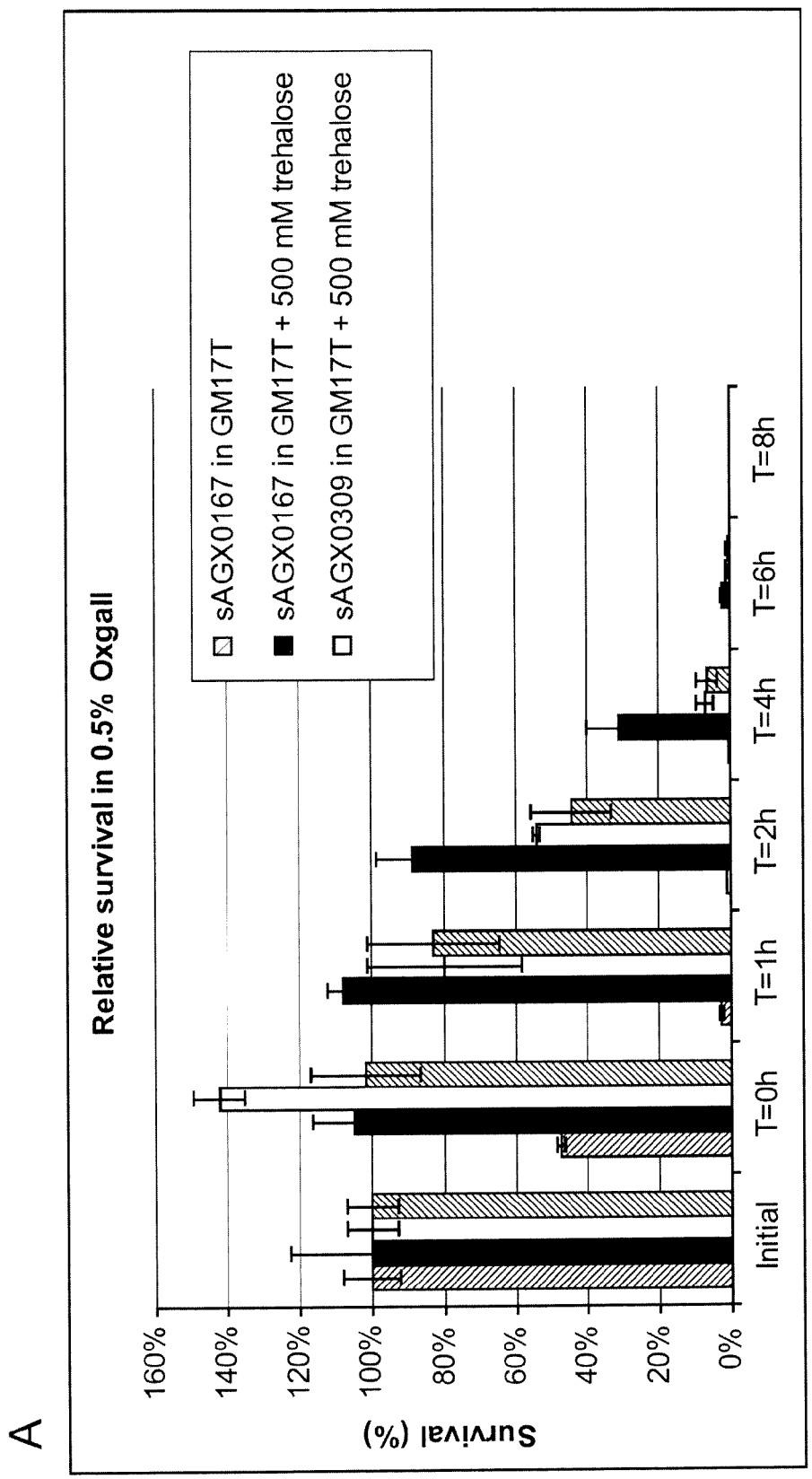
FIG. 2: The accumulation of exogenous trehalose in *L. lactis* cells provides protection towards bile lysis. (A) survival; and (B) trehalose content.
Figure 2:
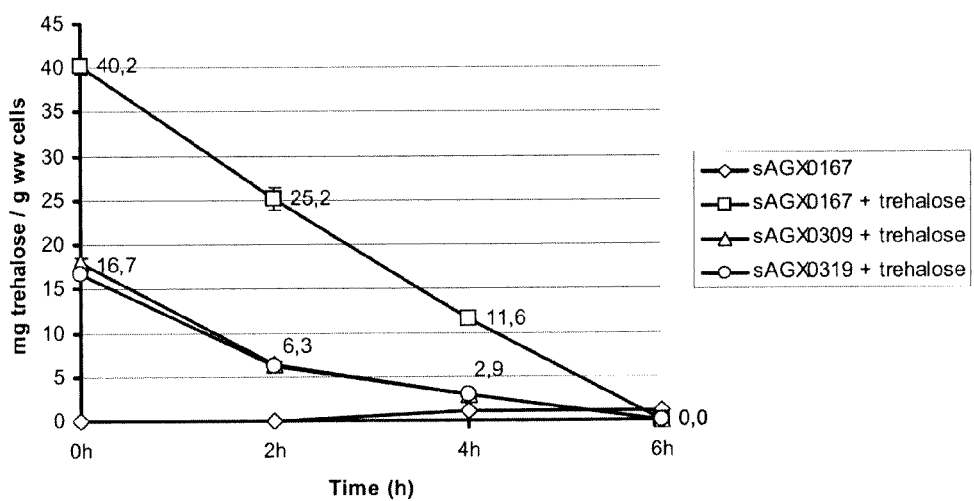

Indicated in FIG. 2 is that the accumulation of exogenous trehalose in L. lactis cells provides protection towards bile lysis. Release of intracellular trehalose limits the protective effect of trehalose in time. L. lactis cells that have accumulated trehalose (sAGX0167+trehalose, sAGX0309+trehalose and sAGX0319+trehalose) i.e. grown in 500 mM trehalose as described in (FIG. 2 B) show a substantial protection in time against bile lysis, proportional to the concentration of intracellular trehalose when compared to L. lactis cells without intracellular trehalose (sAGX0167, pre-cultured without trehalose). Decreasing survival in 0.5% oxgal (FIG. 2 A) coincides with release of intracellular trehalose (FIG. 2 B).

EXAMPLE 3

The Accumulation of Exogenous Trehalose in Provides Protection Towards Bile Lysis Experimental Cells were collected by centrifugation and resuspended in 1×M9 salts solution. Samples were taken and trehalose concentrations were determined at T0, 1, 2 and 4 hours, essentially as described in Example 1. Data are exemplary for all ptcC wt strains.

Results

Following accumulation, Trehalose to some extent leaks from cells through an up to now unidentified or unanticipated trehalose exit port and can be recovered in the supernatant.

Figure 3:
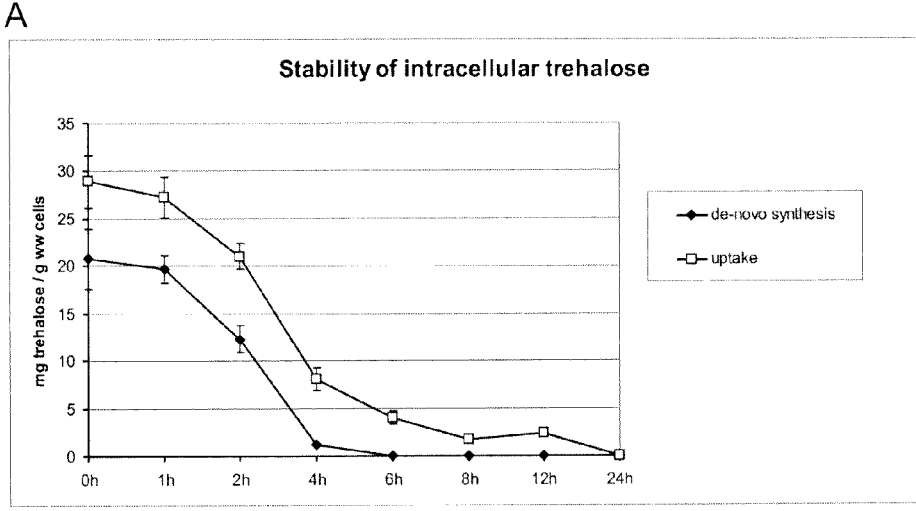
FIG. 3: Accumulation and stability of intracellular trehalose. (A) trehalose release over time; and (B) trehalose increase in supernatant.
Figure 3:
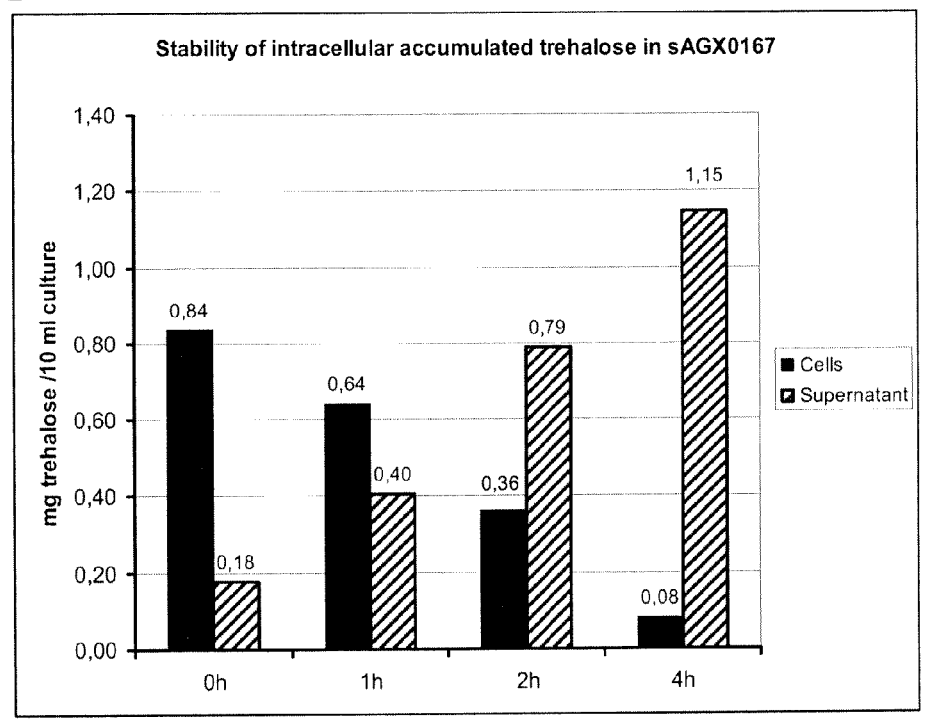

FIG. 3 A indicates that trehalose can be accumulated intracellular by de-novo synthesis as well as following uptake from the growth medium (sAGX0167 grown in 500 mM trehalose, as described in FIG. 1). Both de-novo synthesized as well as exogenously accumulated trehalose are released from the cells. FIG. 3 B indicates that loss of intracellular trehalose results in increase of trehalose present in the culture supernatant (here expressed as mg trehalose/10 ml culture to allow comparison between intracellular and extracellular trehalose concentration).

EXAMPLE 4

Trehalose Accumulation and Release in Various Strains Described in Table 2

Experimental

Strains described in Table 2 were grown in GM17 supplemented with 100 mM (FIG. 4 A) or 500 mM (FIG. 4 B) trehalose. Cells were collected and resuspended in M9 buffer (Difco). Intracellular trehalose content was determined at T0, 2, 4 and 8 h, essentially as described in Example 1. Except for sAGX0248 (ptcC KO) all strain show a similar release of trehalose as described in FIG. 3.

Results

20 L. lactis MG1363 oligosacharide transporters were selected from COG database (section Carbohydrate transport and metabolism) and their genes were disrupted by oligonucleotide directed recombineering in a trePP KO background (sAGX0272; required for trehalose accumulation) (Table 2; FIG. 4). Only the disruption of ptcC circumvents the release of trehalose.

One cannot predict which of the genes listed in Table 2 is involved in trehalose release. Disruption of either one of the PTS transporter genes present in the trehalose operon (IImg_0453; IImg_0454) has no effect on trehalose uptake or release. Disruption of the ptcC gene (encoding cellobiose-specific PTS system IIC component) resolves leakage of accumulated trehalose, therefore the PtcC is the trehalose exit port and this protein causes leakage of trehalose. Disruption of celB (cellobiose-specific PTS system IIC component) has no effect on trehalose uptake or release. Disruption of ptcC in trePP KO background prevents all release of trehalose.

EXAMPLE 5

Trehalose Accumulation and Release in Various Strains Described in Table 2

Experimental

Strains were grown overnight in GM17T+500 mM trehalose at 30° C., cells were collected by centrifugation and resuspended in an equal volume 1×M9 (FIG. 5 A) or 0.5% Oxgal in 0.9% NaCl (FIG. 5 B) and incubated for 24 h at 37° C. Samples were taken at T0, 1, 2, 4, 6, 8, 12 and 24 h. Intracellular trehalose content was determined as described in Example 1.

Results

Combined ptcC KO (stop codon insertion as well as gene deletion) and PhIIA>>trePTC (constitutive high expression of trehalose transporter) allows for high trehalose import and full intracellular retention.

Figure 5:
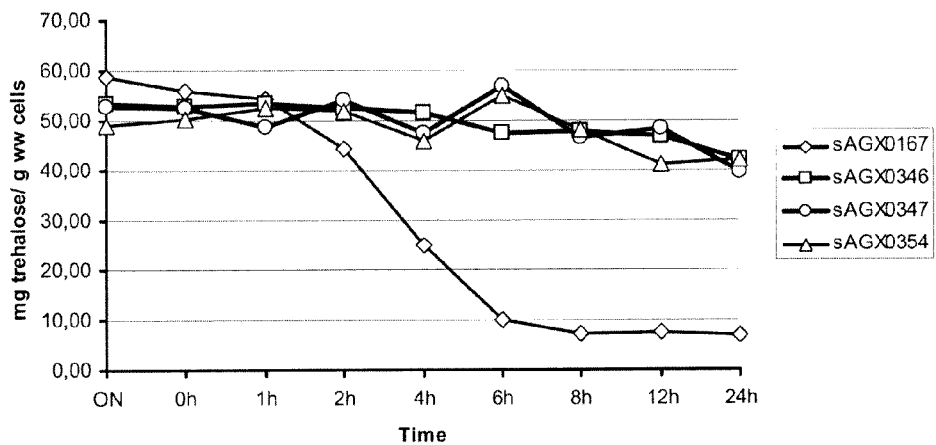
FIG. 5: Inactivation of ptcC prevents (in M9 salts, panel A) or delays (in 0.5% oxgal, panel B) the release of intracellular trehalose.
Figure 5:
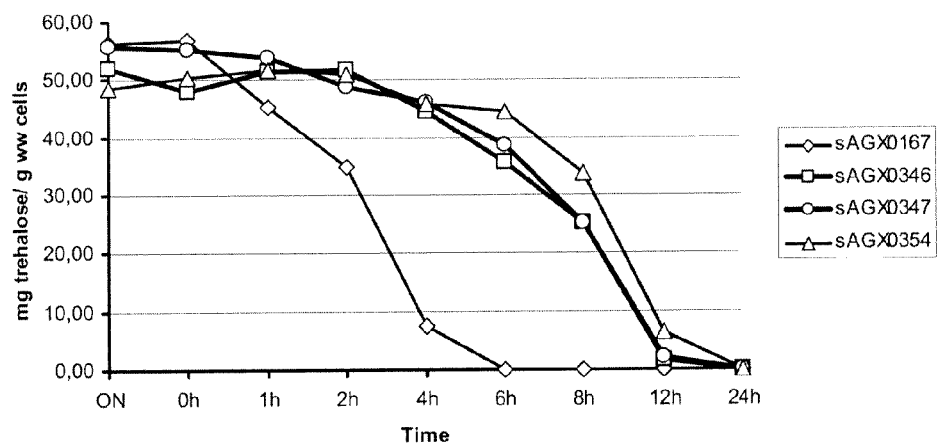

FIG. 5 indicates that inactivation of ptcC prevents (in M9 salts, panel A) or delays (in 0.5% oxgal, panel B) the release of intracellular trehalose. Presence of the strong constitutive PhIIA promoter (as disclosed in WO 2008/084115, which incorporated herein in its entirety by reference) in front of both PTS genes of the L. lactis trehalose operon restores the capacity to accumulate exogenous trehalose to that of a reference strain (see also FIG. 4).

EXAMPLE 6

The Accumulation of Exogenous Trehalose Provides Protection Towards Bile Lysis Experimental Strains were grown overnight in GM17T+500 mM trehalose at 30° C., cells were collected by centrifugation and resuspended in half a volume 0.9% NaCl. Samples were taken and CFU were determined by plating appropriate dilutions (initial). At T0, half a volume 1% oxgal in 0.9% NaCl was added and incubated for 8 h at 37° C. Samples were taken at T0, 1, 2, 4, 6, 8, 12 and 24 hours. Trehalose content was determined (FIG. 6 A, essentially as in Example 1) and CFU were determined by plating (0-8 hours only) appropriate dilutions and plotted as % of initial T0 values (FIG. 6 B).

Results

The enhanced capacity to retain intracellular trehalose leads to improved bile resistance.

Figure 6:
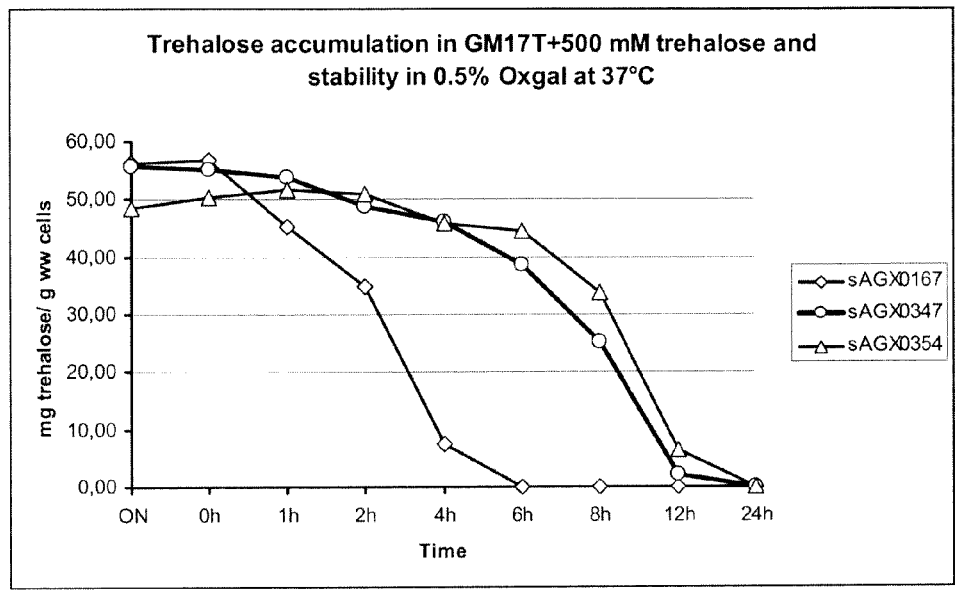
FIG. 6: The accumulation of exogenous trehalose in *L. lactis* cells provides protection towards bile lysis. (A) release of intracellular trehalose over time; and (B) survival over time in 0.5% oxgal
Figure 6:
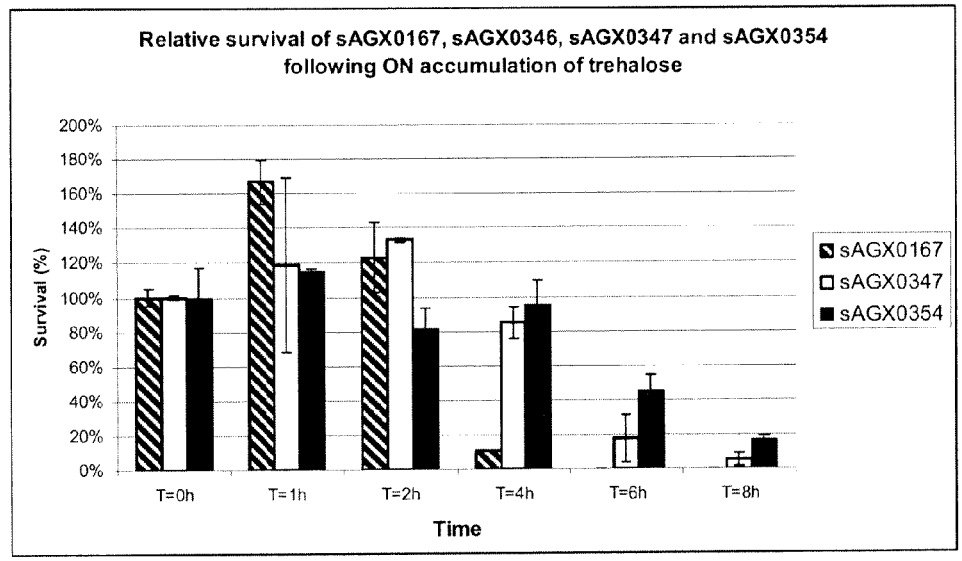

FIG. 6 indicates that the accumulation of exogenous trehalose in *L. lactis* cells provides protection towards bile lysis. Release of intracellular trehalose (A) coincides with decreasing survival in 0.5% oxgal (B). Inactivation of ptcC extends the presence in time of intracellular trehalose and consequently also improves resistance in time towards oxgal.

EXAMPLE 7 trePP KO Strains are Capable of Converting Glucose or Maltose to Intracellular Trehalose. Maltose Stimulates Trehalose Uptake by trePP KO Strains Experimental Strains were grown overnight in the indicated media. Trehalose was determined essentially as described in Example 1.

Results trePP KO strains have acquired the capacity to utilize carbon sources such as glucose or maltose to accumulate trehalose. This is not described in the prior art as trehalose can accumulate inside the cells in MM17T i.e. with maltose as the single carbon source.

Figure 7:
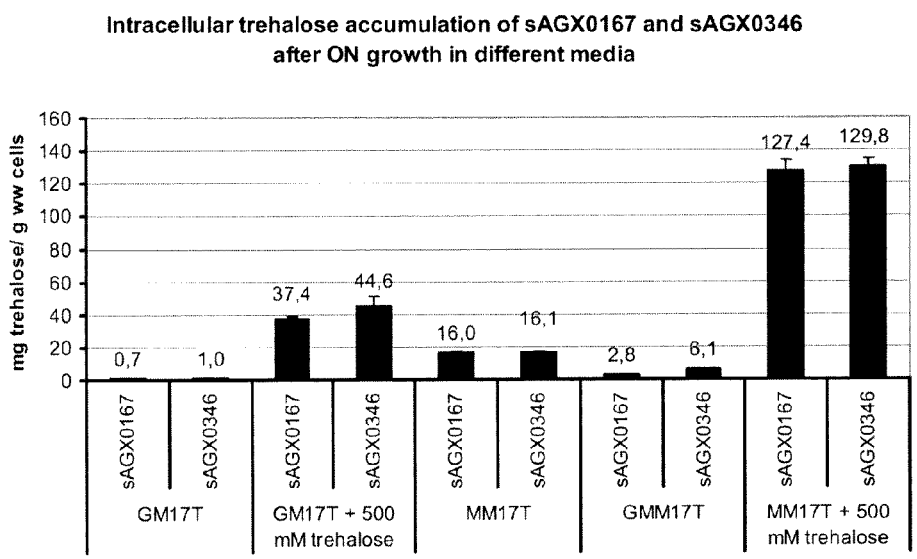
FIG. 7: trePP KO strains (both ptcC wt as well as ptcC KO) are capable of converting glucose or maltose to intracellular trehalose

FIG. 7 indicates that trePP KO strains (both ptcC wt as well as ptcC KO) are capable of converting glucose or maltose to intracellular trehalose (columns 1 and 2, columns 5-8). Maltose enhances the uptake and accumulation of extracellular trehalose from the growth medium in trePP KO strains (columns 9 and 10).

trePP KO strains accumulate trehalose when grown:

1. With glucose as a carbon source (GM17T; columns 1 and 2)
2. With glucose as a carbon source and extracellular trehalose (GM17T+500 mM trehalose; columns 3 and 4)
3. With maltose as a carbon source (MM17T; columns 5 and 6)
4. With glucose and maltose as a carbon source (GM M17T; columns 7 and 8)
5. With maltose as a carbon source and extracellular trehalose (MM17T+500 mM trehalose; columns 9 and 10)

EXAMPLE 8

Survival after Lyophylization

Experimental

Table 3 A: Growth optimized 200 L culture (animal protein free fermentation medium) was 10 fold concentrated through ultrafiltration and diafiltration and re-suspension in concentrated cryoprotectant mix (as described in WO 2010/124855). CFU count per ml was determined for the bacterial suspension. The suspension was filled out in bulk and analytical trays, trays were weighed and lyophilized. For viability assessment, lyophilized appropriate weight portions were reconstituted with appropriate volumes of purified water and CFU count per ml was determined. Viability % was determined from the ratio of CFU before and after lyophilization.

Table 3 B: Overnight 20 L culture (GM17T+500 mM trehalose) was 100 fold concentrated by centrifugation and re-suspension in concentrated cryoprotectant mix (as described in WO 2010/124855). CFU count per ml was determined for the bacterial suspension. The suspension was lyophilized in bulk and in vials (2.5 ml fill volume). For viability assessment, lyophilized 2.5 ml vials were reconstituted with 2.5 ml purified water and CFU count per ml was determined. Viability % was determined from the ratio of CFU before and after lyophilization. 2 independent production batches (sAGX0167 and sAGX0309) yield>100% survival after lyophilization.

Both (A) and (B) lyophilized powders were further formulated with suitable excipients to standardize CFU/g. sAGX0037, sAGX0167 and sAGX0309 were filled in HPMC capsules to a minimum of $1.2 \times 10^{11}$ CFU/capsule. Capsules were banded with a cellulose film and coated with methacrylic acid—ethylacrylate co-polymers as an enteric coating film, for targeted delivery to the small intestine and colon.

Trehalose was determined essentially as described in Example 1.

Results

As indicated in Table 3, strains that can accumulate trehalose show greatly enhanced resistance to drying stress as experienced during freeze-drying.

TABLE 3

| Strain | | CFU/ml formulated biomass | CFU/ml freeze-dried cake | Trehalose content | survival |
|---|---|---|---|---|---|
| sAGX0037 exp. 1 | A | $1.60 \times 10^{11}$ | $1.26 \times 10^{11}$ | n/a | 79% |
| sAGX0037 exp. 2 | | $1.50 \times 10^{11}$ | $1.47 \times 10^{11}$ | n/a | 98% |
| sAGX0037 exp. 3 | | $1.40 \times 10^{11}$ | $1.02 \times 10^{11}$ | n/a | 73% |
| sAGX0037 exp. 4 | | $1.50 \times 10^{11}$ | $1.26 \times 10^{11}$ | n/a | 84% |
| sAGX0085 exp. 1 | | $2.00 \times 10^{11}$ | $1.40 \times 10^{11}$ | n/a | 70% |
| sAGX0085 exp. 2 | | $1.60 \times 10^{11}$ | $1.42 \times 10^{11}$ | n/a | 89% |
| sAGX0167 exp. 1 | B | $1.14 \times 10^{11}$ | $1.21 \times 10^{11}$ | 16.29 mg/g ww | 106% |
| sAGX0309 exp. 1 | | $1.21 \times 10^{11}$ | $1.45 \times 10^{11}$ | 16.72 mg/g ww | 120% |

EXAMPLE 9

Survival During Intestinal Passage Through Porcine Intestine

Experimental

Sows (>150 kg) were surgically equipped with cannulae at the proximal duodenum and proximal colon. In the duodenal cannula, encapsulated, freeze-dried sAGX0037 and sAGX0167 were inserted. Colonic content was sampled from the colon cannula at 0, 2, 4, 6, 8 and 10 hours post administration. Viability % was determined as the ratio between live (CFU count) and total (live and dead; Q-PCR analysis) *L. lactis* in the samples. Numbers are given in Table 4.

Results

Strains that can accumulate trehalose show greatly enhanced survival, independent of the feeding or fasting status, in a large intestinal system (pig).

Figure 8:
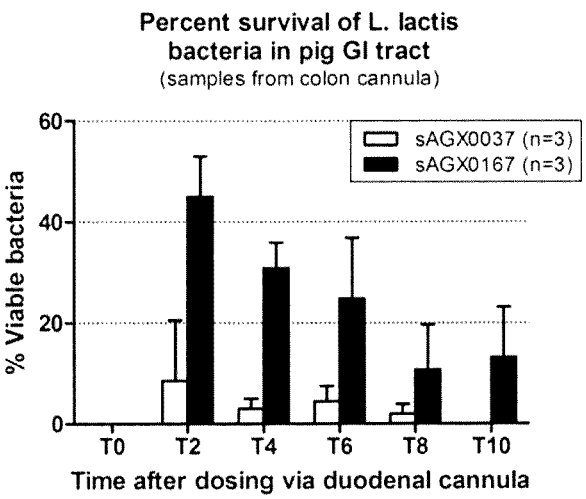
FIG. 8: Enhanced survival during intestinal passage through porcine intestine, both when pigs were fasted for 24 hours (A) as well as during ad libitum food availability (B).
Figure 8:
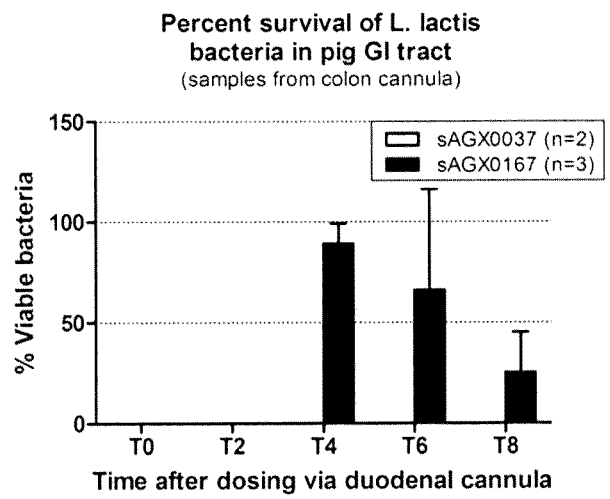

Table 4 and FIG. 8 indicate that when compared to freeze dried and encapsulated sAGX0037 (Table 4 A), freeze dried and encapsulated sAGX0167 (pregrown for intracellular trehalose accumulation; Table 4 B) show enhance survival during intestinal passage through porcine intestine, both when pigs were fasted for 24 hours (FIG. 8 A) as well as during ad libitum food availability (FIG. 8 B).

TABLE 4

|  | Time-point | sAGX0037 | sAGX0167 | p-value |
|---|---|---|---|---|
| Fasted | T0 | — | — |  |
|  | T2 | 8.5% | 45.1% | 0.033 |
|  | T4 | 3.0% | 30.9% | 0.001 |
|  | T6 | 4.5% | 24.8% | 0.044 |
|  | T8 | 1.9% | 10.7% | 0.176 |
|  | T10 | 0.0% | 13.2% |  |
| Fed | T0 | — | — |  |
|  | T2 | — | — |  |
|  | T4 | 0.0% | 89% | 0.001 |
|  | T6 | 0.0% | 66% | 0.173 |
|  | T8 | 0.0% | 25% | 0.203 |

EXAMPLE 10

Trehalose can be Accumulated after Production of Biomass

Experimental

Indicated strains were grown overnight in GM17T (16 hrs at 30° C.) and were collected by centrifugation (15 min at 4000 rpm). Bacterial pellets were resuspended in fresh GM17T+500 mM trehalose and incubated. Intracellular trehalose content was determined at T=0, 1, 2 and 4 hours as described in Example 1.

Results

Figure 9:
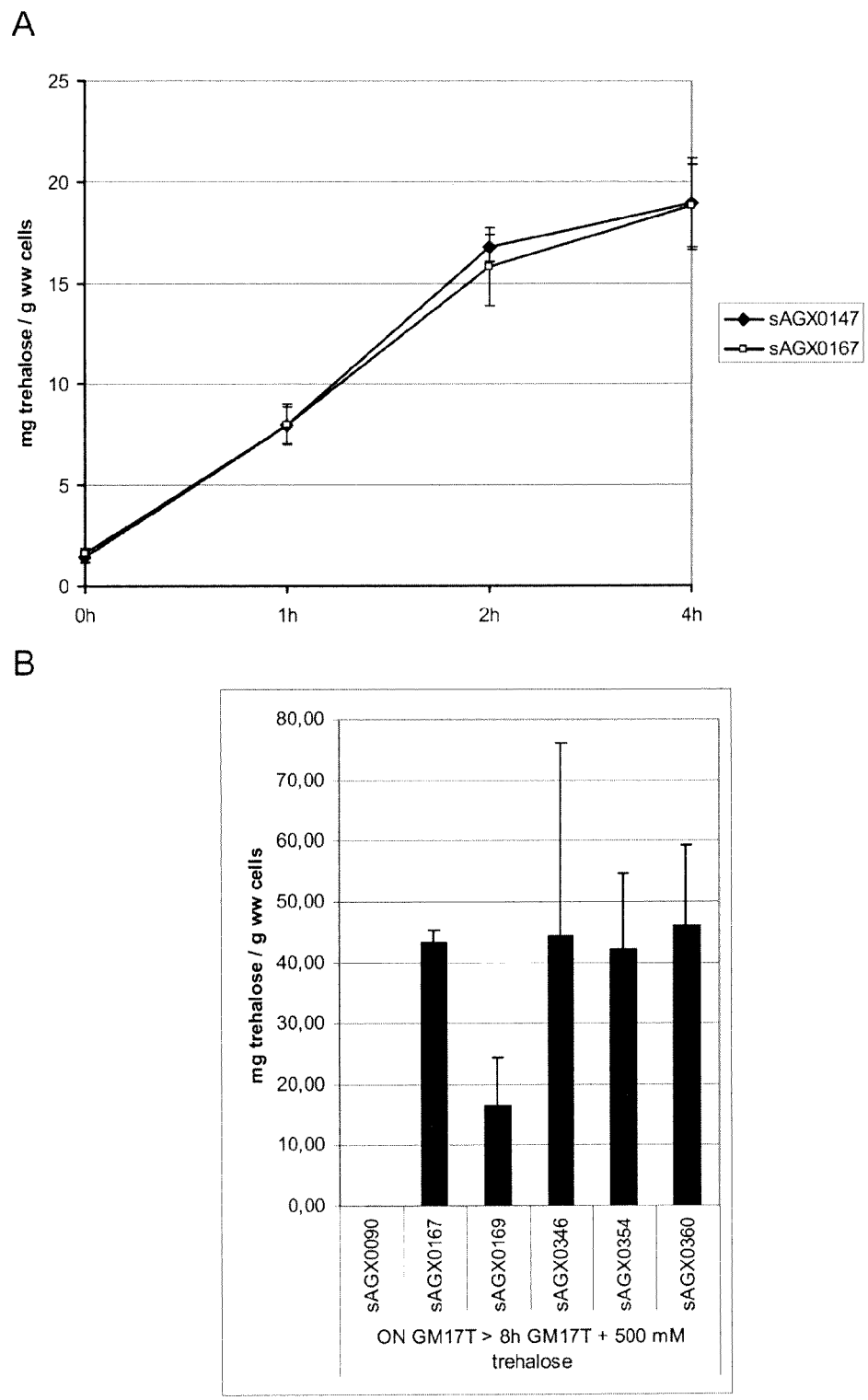
FIG. 9: Trehalose accumulation after production of biomass.

As indicated in FIG. 9 A, trehalose can be accumulated after biomass production, when the bacteria are incubated over time. As indicated in FIG. 9 B, this can be achieved only in trePP KO strains (sAGX0090 vs other) and does not require further gene insertion or deletion (sAGX0169). The additional presence of otsB (sAGX0167, sAGX0346, sAGX0354, sAGX0360) stimulates trehalose accumulation.

EXAMPLE 11

Maltose can Stimulate the Accumulation of Intracellular Trehalose

Experimental

Indicated strains were grown overnight (ON; 16 hrs at 30° C.) in GM17T, +/−500 mM trehalose, GM17T+0.5% maltose (GMM17T)+500 mM trehalose or M17T+0.5% maltose (MM17T)+500 mM trehalose and were collected by centrifugation (15 min at 4000 rpm). Intracellular trehalose content was determined as described in Example 1.

Results

Figure 10:
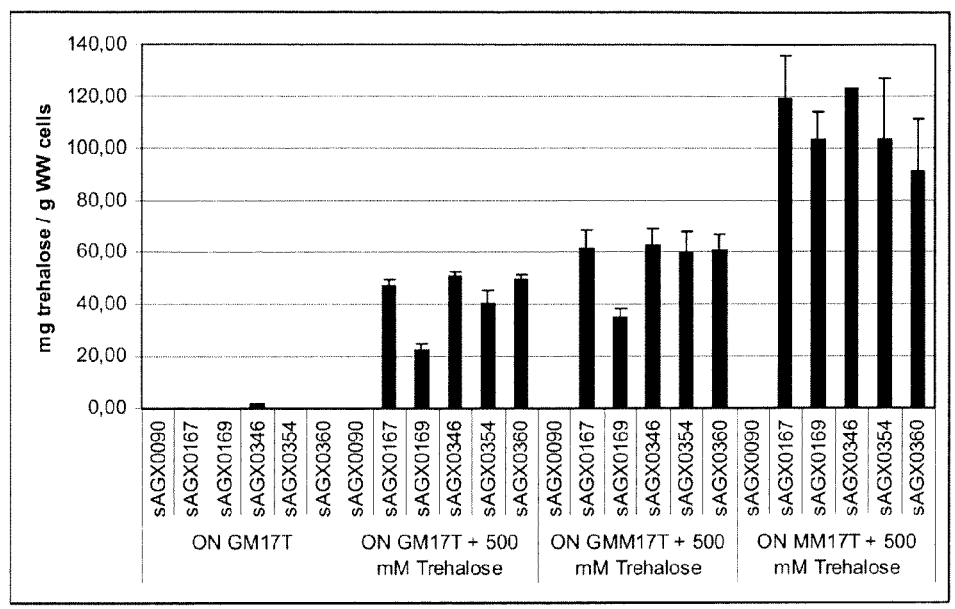
FIG. 10: Stimulation of the accumulation of intracellular trehalose by maltose.

As indicated in FIG. 10, maltose stimulates the accumulation of intracellular trehalose in over night grown cultures.

EXAMPLE 12

Maltose can be Converted to Intracellular Trehalose During or after Production of Biomass Experimental Indicated strains were grown overnight (ON, 16 hrs at 30° C.) in GM17T, cells were collected by centrifugation (15 min at 4000 rpm), resuspended in M17T+0.5% maltose (MM17T and incubated for 8 hours (>8 h MM17T). Alternatively, indicated strains were grown ON in MM17T. Intracellular trehalose content was determined as described in Example 1.

Results

Figure 11:
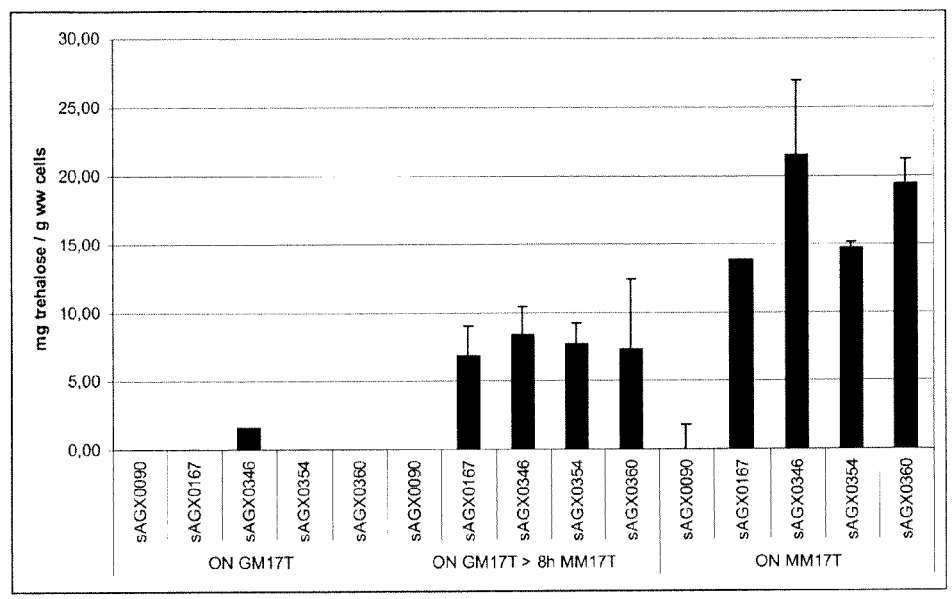
FIG. 11: Conversion of maltose to intracellular trehalose during or after production of biomass.

As indicated in FIG. 11, maltose can be converted to intracellular trehalose during or after production of biomass.

abbreviations

| | |
|---|---|
| ADP | adenosine-5'diphosphate |
| anti-TNF | Antibody recognizing tumor necrosis factor |
| ATP | adenosine-5'triphoshate |
| celB | cellobiose-specific PTS system IIC component |
| CFU | Colony forming unit |
| COGs | Clusters of Orthologous Groups of proteins |
| eno | enolase (phosphopyruvate hydratase) gene (Gene ID: 4797432) |
| gapB | glyceraldehyde-3-phosphate dehydrogenase gene (Gene ID: 4797877) |
| Gene ID | Gene identifier |
| GM17 | Oxoid M17 + glucose at 0.5% |
| GM17T | Oxoid M17 + glucose at 0.5% + thymidine at 0.2 mM |
| GMM17T | Oxoid M17 + glucose at 0.5% + maltose at 0.5% + thymidine at 0.2 mM |
| hIL-10 | Human interleukin-10 |
| HPMC | Hydroxypropylmethylcellulose |
| hTFF-1 | Human trefoil factor-1 |
| KO | Knock-out; gene deletion, gene replacement, gene disruption |
| M | maltose at 0.5% |
| M17 | Oxoid M17 |
| M9 | M9 salts (Difco) |
| MM17 | Oxoid M17 + maltose at 0.5% |
| MM17T | Oxoid M17 + maltose at 0.5% + thymidine at 0.2 mM |
| n/a | not applicable |
| NADP+ | nicotinamide-adenine dinucleotide phosphate |
| NADPH | reduced nicotinamide-adenine dinucleotide phosphate |
| ODx | Optical density at x nm wavelength |
| otsA | *Escherichia coli* osmoregulatory trehalose synthesis A; trehalose-6-phosphate synthase |
| otsB | *Escherichia coli* osmoregulatory trehalose synthesis B; trehalose-6-phosphate phosphatase |
| otsBA | Coupled expression unit for otsB and otsA |
| pgmB | β-phosphoglucomutase (Gene ID: 4797271) |
| PhllA | Promoter of the HU-like DNA-binding protein gene (Gene ID: 4797353) |
| ptcC | cellobiose-specific PTS system IIC component |
| Ptre | trehalose operon promoter |

| | |
|---|---|
| PTS | phosphotransferase system |
| rpmD | Intergenic region preceding the 50 S ribosomal protein L30 gene |
| T | thymidine at 0.2 mM |
| thyA | Thymidylate synthase gene (Gene ID: 4798358) |
| TNF | Tumor necrosis factor |
| trePP | trehalose-6-phosphate phosphorylase (Gene ID: 4797140) |

| | |
|---|---|
| trePTC | Putative phosphotransferase genes in the *L. lactis* trehalose operon (llmg_0453 and llmg_0454; Gene ID: 4797778 and Gene ID: 4797093 respectively) |
| TX | Time point X hours |
| uidA | *Escherichia coli* beta-D-glucuronidase gene |
| usp45 | unidentified secreted 45-kDa protein gene (Gene ID: 4797218) |
| wt | wild type |
| ww | wet cell pellet weight |

What is claimed is:

1. A composition comprising a gram positive bacterium selected from a lactic acid bacterium (LAB) and a *Bifidobacterium*, the gram positive bacterium lacking trehalose 6-phosphate phosphorylase (TrePP) activity and cellobiose-specific PTS system IIc component ("ptcC") activity, and pharmaceutically acceptable carrier.

2. The composition according to claim 1, wherein the gram positive bacterium does not contain functional heterologous trehalose 6-phosphate phosphatase.

3. The composition according to claim 1, wherein the gram positive bacterium overexpresses one or more genes encoding a trehalose transporter.

4. The composition according to claim 1, wherein the gram positive bacterium contains one or more heterologous gene product.

5. The composition according to claim 1, wherein the gram positive bacterium is dried, spray-dried, frozen or freeze-dried.

6. A food additive, a probiotic composition or a starter culture comprising a gram positive bacterium selected from a lactic acid bacterium (LAB) and a *Bifidobacterium*, the gram positive bacterium lacking TrePP activity and ptcC activity.

7. The starter culture according to claim 6, wherein the starter culture is a starter culture for the preparation of a food product.

8. The food additive, probiotic composition or starter culture according to claim 6, wherein the gram positive bacterium does not contain functional heterologous trehalose 6-phosphate phosphatase.

9. The food additive, probiotic composition or starter culture according to claim 6, wherein the gram positive bacterium overexpresses one or more genes encoding a trehalose transporter.

10. The food additive, probiotic composition or starter culture according to claim 6, wherein the gram positive bacterium expresses one or more heterologous gene products.

11. The food additive, probiotic composition or starter culture according to claim 6, wherein the food additive or starter culture is frozen, dried, spray-dried or freeze-dried.

12. A method for preparing a food product, comprising admixing the food additive, the probiotic composition or the starter culture according to claim 6 with a substrate material capable of being fermented by the gram positive bacterium, optionally further comprising fermenting said substrate material.

13. A food product comprising the food additive according to claim 6, and a substrate material capable of being fermented by the gram positive bacterium.

14. The composition according to claim 1, wherein a gene encoding endogenous TrePP has been partially or completely deleted, disrupted or inactivated such as being incapable of producing functional TrePP gene product.

15. The composition according to claim 1, wherein a gene encoding endogenous ptcC has been partially or completely deleted, disrupted or inactivated such as being incapable of producing functional ptcC gene product.

16. The composition according to claim 3, wherein overexpression of the one or more genes encoding a trehalose transporter is constitutive.

17. The composition according to claim 3, wherein the one or more genes encoding a trehalose transporter is endogenous to the gram positive bacterium.

18. The composition according to claim 4, wherein the one or more heterologous gene product is one or more prophylactic or therapeutic gene product or antigen.

19. The food additive, the probiotic composition or the starter culture according to claim 6, wherein a gene encoding endogenous TrePP has been partially or completely deleted, disrupted or inactivated such as being incapable of producing functional TrePP gene product.

20. The food additive, the probiotic composition or the starter culture according to claim 6, wherein a gene encoding endogenous ptcC has been partially or completely deleted, disrupted or inactivated such as being incapable of producing functional ptcC gene product.

21. The food additive, the probiotic composition or the starter culture according to claim 9, wherein overexpression of the one or more genes encoding a trehalose transporter is constitutive.

22. The food additive, the probiotic composition or the starter culture according to claim 9, wherein the one or more genes encoding a trehalose transporter is endogenous to the gram positive bacterium.

23. The food additive, the probiotic composition or the starter culture according to claim 10, wherein the one or more heterologous gene product is one or more prophylactic or therapeutic gene product or antigen.

24. The composition according to claim 1, wherein the lactic acid bacterium is *Lactococcus lactis*.

25. The food additive, probiotic composition or starter culture according to claim 6, wherein the lactic acid bacterium is *Lactococcus lactis*.

* * * * *

SEQUENCE LISTING

```
<160> NUMBER OF SEQ ID NOS: 13

<210> SEQ ID NO 1
<211> LENGTH: 2310
<212> TYPE: DNA
<213> ORGANISM: Lactococcus lactis

<400> SEQUENCE: 1
atgactgata aagattggat gatccaatat gacaaacaag aagtagggaa gcgttcttat      60
gggcaagaat ctttaatgtc attgggaaat ggttatttag ggcttcgtgg ggcgcctttg     120
tgggcaactt gttcggataa tcattatccg ggactctatg tcgcaggggt ctttaatcac     180
acaagtacag aagttgcagg tcatgatgtt atcaacgaag atatggtcaa ttggccaaat     240
ccacaattga ttaaggttta tattgataat gaattggtta acttcgaggc agcaattgag     300
aaaaattctt cgattgattt caaaaatgga ttgcaaattg agagctataa tgtcagttta     360 gccaaggggag gtttgacttt agtgaccaca aaatttgttg atcccatcca ttttcacgat     420
tttgggttcg ttggagaaat catcgctgat ttttctggaa aattgcgaat agaaactttt     480
attgatggtt cggtattgaa tcaaaatgtt gaacgctatc gggcttttga cagcaaagaa     540
tttgaagtga ctcaaattgc tgatggactt ttggtggcaa aaactagaac gacggacata     600
gaattagcag ttgcgactaa aacttattta aatggtcagc cattgaaaaa agtagaatct     660
ggaaattctg aaattttaa agaatccatt gaagttgatt tactaaaaa ccaagaagtt      720 cagttttgaaa aatcgattgt tattgctagt tcttatgaaa ccaaaaaccc tgttgaattt     780
gtgctgacag aactggcagc aacttctgtc agtaaaattc aggaaaataa tgcaaattat     840
tgggagaaag tatggcagga tggcgatatt gtcatcgaat ctgatcatgc ggatttgcaa     900
agaatggtgc gaatgaatat tttccatatt cgccaagcgg cacaacacgg tgctaatcag     960 ttttttagatg cgtccgtagg ttcgcgtgga ttgactggtg aaggttatcg aggacatatt    1020
ttctgggatg aaattttgt tctaccttat tatgcggcga atgaaccaga aacagcgcgt     1080
gatttgcttt tgtaccgaat caatcgattg actgctgcac aggaaaatgc aaaggttgat    1140
ggagaaatag gggcaatgtt tccttggcaa tccggcttaa ttggggatga acaggcacaa    1200
tttgttcatt tgaatacagt aaataatgaa tgggaaccag ataatagtcg ccgtcaaaga    1260
catgtcagct tagctattgt ttacaatctg tggatttact tacagctgac agatgatgaa    1320
agtattttga ctgacggtgg actggatttg ctcgttgaaa ccacgaagtt ttggttaaac    1380
aaagcagaat tgggaagtga tagccgctat catatcgctg tgtcatggg tcctgatgaa    1440 tatcatgagg cttatccagg gcaagaaggt ggtatttgcg ataatgctta tacgaatttg    1500
atgctgactt ggcagttaaa ttggctgaca gagctgtcag tgaaaggttt tgaaattcca    1560
gcagatttgc ttgaagagtc acaaaaggtt cgggaaaatc tttatttaga tattgatgag    1620
aatggtgtga ttgcccaata tgctaagtat tttgagctta agaagttga ttttgcagct    1680
```

```
tatgaagcaa aatatggcga tattcatcgg attgaccgtt tgatgaaggc tgagggaatt      1740
tcgcctgacg aatatcaagt ggctaaacaa gctgatacct tgatgttaat gtacaatttg      1800
ggtcatgaac atgtgatcaa attggtcaaa caattaggtt atgagctacc caaaaattgg      1860
ttgaaagtta atcgtgatta ttatcttgca cgaactgtcc atggttcaac acatctcgt       1920 ccagttttg ctgggattga tgtcaaattg ggtgattttg atgaagcgct tgactttta        1980 atcactgcga ttgaagtga ttactatgat attcaaggcg aaccacggc cgaaggggtt        2040 cacattgggg tcatgggaga aacacttgaa gtgattcaaa atgaatttgc cggtttgaca      2100
ctacgcgatg gatactttc aattgctccg catttaccaa aaagttggac caaattgaaa       2160
ttcagtcaaa ttttcaaagg ttgtcaagtg gaaattttga ttgaaaaagg tcaattatta     2220
ctgacagctt catcgactt gctgattaaa gtttatgatg aggaagttca gttaaaagca      2280
ggagtacaag ctaattttga tttaaaataa                                        2310
```

<210> SEQ ID NO 2
<211> LENGTH: 769
<212> TYPE: PRT
<213> ORGANISM: Lactococcus lactis

<400> SEQUENCE: 2

```
Met Thr Asp Lys Asp Trp Met Ile Gln Tyr Asp Lys Gln Glu Val Gly
1               5                   10                  15

Lys Arg Ser Tyr Gly Gln Glu Ser Leu Met Ser Leu Gly Asn Gly Tyr
            20                  25                  30

Leu Gly Leu Arg Gly Ala Pro Leu Trp Ala Thr Cys Ser Asp Asn His
        35                  40                  45

Tyr Pro Gly Leu Tyr Val Ala Gly Val Phe Asn His Thr Ser Thr Glu
    50                  55                  60

Val Ala Gly His Asp Val Ile Asn Glu Asp Met Val Asn Trp Pro Asn
65                  70                  75                  80

Pro Gln Leu Ile Lys Val Tyr Ile Asp Asn Glu Leu Val Asp Phe Glu
                85                  90                  95

Ala Ala Ile Glu Lys Asn Ser Ser Ile Asp Phe Lys Asn Gly Leu Gln
            100                 105                 110

Ile Glu Ser Tyr Asn Val Ser Leu Ala Lys Gly Gly Leu Thr Leu Val
        115                 120                 125

Thr Thr Lys Phe Val Asp Pro Ile His Phe His Asp Phe Gly Phe Val
130                 135                 140

Gly Glu Ile Ile Ala Asp Phe Ser Gly Lys Leu Arg Ile Glu Thr Phe
145                 150                 155                 160

Ile Asp Gly Ser Val Leu Asn Gln Asn Val Glu Arg Tyr Arg Ala Phe
                165                 170                 175

Asp Ser Lys Glu Phe Glu Val Thr Gln Ile Ala Asp Gly Leu Leu Val
            180                 185                 190

Ala Lys Thr Arg Thr Thr Asp Ile Glu Leu Ala Val Ala Thr Lys Thr
        195                 200                 205

Tyr Leu Asn Gly Gln Pro Leu Lys Lys Val Glu Ser Gly Asn Ser Glu
    210                 215                 220

Ile Phe Lys Glu Ser Ile Glu Val Asp Leu Leu Lys Asn Gln Glu Val
225                 230                 235                 240

Gln Phe Glu Lys Ser Ile Val Ala Ser Ser Tyr Glu Thr Lys Asn
                245                 250                 255
```

-continued

```
Pro Val Glu Phe Val Leu Thr Glu Leu Ala Ala Thr Ser Val Ser Lys
            260                 265                 270
Ile Gln Glu Asn Asn Ala Asn Tyr Trp Glu Lys Val Trp Gln Asp Gly
        275                 280                 285
Asp Ile Val Ile Glu Ser Asp His Ala Asp Leu Gln Arg Met Val Arg
    290                 295                 300
Met Asn Ile Phe His Ile Arg Gln Ala Ala Gln His Gly Ala Asn Gln
305                 310                 315                 320
Phe Leu Asp Ala Ser Val Gly Ser Arg Gly Leu Thr Gly Glu Gly Tyr
                325                 330                 335
Arg Gly His Ile Phe Trp Asp Glu Ile Phe Val Leu Pro Tyr Tyr Ala
            340                 345                 350
Ala Asn Glu Pro Glu Thr Ala Arg Asp Leu Leu Tyr Arg Ile Asn
        355                 360                 365
Arg Leu Thr Ala Ala Gln Glu Asn Ala Lys Val Asp Gly Glu Ile Gly
    370                 375                 380
Ala Met Phe Pro Trp Gln Ser Gly Leu Ile Gly Asp Glu Gln Ala Gln
385                 390                 395                 400
Phe Val His Leu Asn Thr Val Asn Asn Glu Trp Glu Pro Asp Asn Ser
                405                 410                 415
Arg Arg Gln Arg His Val Ser Leu Ala Ile Val Tyr Asn Leu Trp Ile
            420                 425                 430
Tyr Leu Gln Leu Thr Asp Asp Glu Ser Ile Leu Thr Asp Gly Gly Leu
        435                 440                 445
Asp Leu Leu Val Glu Thr Thr Lys Phe Trp Leu Asn Lys Ala Glu Leu
    450                 455                 460
Gly Ser Asp Ser Arg Tyr His Ile Ala Gly Val Met Gly Pro Asp Glu
465                 470                 475                 480
Tyr His Glu Ala Tyr Pro Gly Gln Glu Gly Gly Ile Cys Asp Asn Ala
                485                 490                 495
Tyr Thr Asn Leu Met Leu Thr Trp Gln Leu Asn Trp Leu Thr Glu Leu
            500                 505                 510
Ser Val Lys Gly Phe Glu Ile Pro Ala Asp Leu Leu Glu Glu Ser Gln
        515                 520                 525
Lys Val Arg Glu Asn Leu Tyr Leu Asp Ile Asp Glu Asn Gly Val Ile
    530                 535                 540
Ala Gln Tyr Ala Lys Tyr Phe Glu Leu Lys Glu Val Asp Phe Ala Ala
545                 550                 555                 560
Tyr Glu Ala Lys Tyr Gly Asp Ile His Arg Ile Asp Arg Leu Met Lys
                565                 570                 575
Ala Glu Gly Ile Ser Pro Asp Glu Tyr Gln Val Ala Lys Gln Ala Asp
            580                 585                 590
Thr Leu Met Leu Met Tyr Asn Leu Gly His Glu His Val Ile Lys Leu
        595                 600                 605
Val Lys Gln Leu Gly Tyr Glu Leu Pro Lys Asn Trp Leu Lys Val Asn
    610                 615                 620
Arg Asp Tyr Tyr Leu Ala Arg Thr Val His Gly Ser Thr Thr Ser Arg
625                 630                 635                 640
Pro Val Phe Ala Gly Ile Asp Val Lys Leu Gly Asp Phe Asp Glu Ala
                645                 650                 655
Leu Asp Phe Leu Ile Thr Ala Ile Gly Ser Asp Tyr Tyr Asp Ile Gln
            660                 665                 670
Gly Gly Thr Thr Ala Glu Gly Val His Ile Gly Val Met Gly Glu Thr
```

```
                     675                 680                 685
Leu Glu Val Ile Gln Asn Glu Phe Ala Gly Leu Thr Leu Arg Asp Gly
            690                 695                 700

Tyr Phe Ser Ile Ala Pro His Leu Pro Lys Ser Trp Thr Lys Leu Lys
705                 710                 715                 720

Phe Ser Gln Ile Phe Lys Gly Cys Gln Val Glu Ile Leu Ile Glu Lys
                725                 730                 735

Gly Gln Leu Leu Leu Thr Ala Ser Ser Asp Leu Leu Ile Lys Val Tyr
            740                 745                 750

Asp Glu Glu Val Gln Leu Lys Ala Gly Val Gln Ala Asn Phe Asp Leu
        755                 760                 765

Lys

<210> SEQ ID NO 3
<211> LENGTH: 801
<212> TYPE: DNA
<213> ORGANISM: Escherichia coli

<400> SEQUENCE: 3
gtgacagaac cgttaaccga aacccctgaa ctatccgcga aatatgcctg gttttttgat      60
cttgatggaa cgctggcgga aatcaaaccg catcccgatc aggtcgtcgt gcctgacaat     120
attctgcaag gactacagct actggcaacc gcaagtgatg gtgcattggc attgatatca     180
gggcgctcaa tggtggagct tgacgcactg gcaaaacctt atcgcttccc gttagcgggc     240
gtgcatgggg cggagcgccg tgacatcaat ggtaaaacac atatcgttca tctgccggat     300
gcgattgcgc gtgatattag cgtgcaactg catacagtca tcgctcagta tcccggcgcg     360
gagctggagg cgaaagggat ggcttttgcg ctgcattatc gtcaggctcc gcagcatgaa     420
gacgcattaa tgacattagc gcaacgtatt actcagatct ggccacaaat ggcgttacag     480
cagggaaagt gtgttgtcga gatcaaaccg agaggtacca gtaaaggtga ggcaattgca     540
gcttttatgc aggaagctcc ctttatcggg cgaacgcccg tatttctggg cgatgattta     600
accgatgaat ctggcttcgc agtcgttaac cgactgggcg aatgtcagt aaaaattggc     660 acaggtgcaa ctcaggcatc atggcgactg gcgggtgtgc cggatgtctg gagctggctt     720
gaaatgataa ccaccgcatt acaacaaaaa agagaaaata acaggagtga tgactatgag     780
tcgtttagtc gtagtatcta a                                              801

<210> SEQ ID NO 4
<211> LENGTH: 266
<212> TYPE: PRT
<213> ORGANISM: Escherichia coli

<400> SEQUENCE: 4

Met Thr Glu Pro Leu Thr Glu Thr Pro Glu Leu Ser Ala Lys Tyr Ala
1               5                   10                  15

Trp Phe Phe Asp Leu Asp Gly Thr Leu Ala Glu Ile Lys Pro His Pro
            20                  25                  30

Asp Gln Val Val Pro Asp Asn Ile Leu Gln Gly Leu Gln Leu Leu
        35                  40                  45

Ala Thr Ala Ser Asp Gly Ala Leu Ala Leu Ile Ser Gly Arg Ser Met
    50                  55                  60

Val Glu Leu Asp Ala Leu Ala Lys Pro Tyr Arg Phe Pro Leu Ala Gly
65                  70                  75                  80

Val His Gly Ala Glu Arg Arg Asp Ile Asn Gly Lys Thr His Ile Val
```

|   |   | 85 |   |   |   | 90 |   |   |   | 95 |   |
|---|---|---|---|---|---|---|---|---|---|---|---|

His Leu Pro Asp Ala Ile Ala Arg Asp Ile Ser Val Gln Leu His Thr
                      100                  105                  110

Val Ile Ala Gln Tyr Pro Gly Ala Glu Leu Glu Ala Lys Gly Met Ala
     115                  120                  125

Phe Ala Leu His Tyr Arg Gln Ala Pro Gln His Glu Asp Ala Leu Met
 130                  135                  140

Thr Leu Ala Gln Arg Ile Thr Gln Ile Trp Pro Gln Met Ala Leu Gln
145                  150                  155                  160

Gln Gly Lys Cys Val Val Glu Ile Lys Pro Arg Gly Thr Ser Lys Gly
     165                  170                  175

Glu Ala Ile Ala Ala Phe Met Gln Glu Ala Pro Phe Ile Gly Arg Thr
         180                  185                  190

Pro Val Phe Leu Gly Asp Asp Leu Thr Asp Glu Ser Gly Phe Ala Val
     195                  200                  205

Val Asn Arg Leu Gly Gly Met Ser Val Lys Ile Gly Thr Gly Ala Thr
 210                  215                  220

Gln Ala Ser Trp Arg Leu Ala Gly Val Pro Asp Val Trp Ser Trp Leu
225                  230                  235                  240

Glu Met Ile Thr Thr Ala Leu Gln Gln Lys Arg Glu Asn Asn Arg Ser
         245                  250                  255

Asp Asp Tyr Glu Ser Phe Ser Arg Ser Ile
     260                  265

<210> SEQ ID NO 5
<211> LENGTH: 1425
<212> TYPE: DNA
<213> ORGANISM: Escherichia coli

<400> SEQUENCE: 5

| | | | | | |
|---|---|---|---|---|---|
| atgagtcgtt | tagtcgtagt | atctaaccgg | attgcaccac | cagacgagca | cgccgccagt | 60 |
| gccggtggcc | ttgccgttgg | catactgggg | gcactgaaag | ccgcaggcgg | actgtggttt | 120 |
| ggctggagtg | gtgaaacagg | gaatgaggat | cagccgctaa | aaaaggtgaa | aaaaggtaac | 180 |
| attacgtggg | cctcttttaa | cctcagcgaa | caggaccttg | acgaatacta | caaccaattc | 240 |
| tccaatgccg | ttctctggcc | cgcttttcat | tatcggctcg | atctggtgca | atttcagcgt | 300 |
| cctgcctggg | acggctatct | acgcgtaaat | gcgttgctgg | cagataaatt | actgccgctg | 360 |
| ttgcaagacg | atgacattat | ctggatccac | gattatcacc | tgttgccatt | gcgcatgaa  | 420 |
| ttacgcaaac | ggggagtgaa | taatcgcatt | ggtttctttc | tgcatattcc | tttcccgaca | 480 |
| ccggaaatct | tcaacgcgct | gccgacatat | gacaccttgc | ttgaacagct | ttgtgattat | 540 |
| gatttgctgg | gtttccagac | agaaaacgat | cgtctggcgt | tcctggattg | tctttctaac | 600 |
| ctgacccgcg | tcacgacacg | tagcgcaaaa | agccatacag | cctggggcaa | agcatttcga | 660 |
| acagaagtct | acccgatcgg | cattgaaccg | aaagaaatag | ccaaacaggc | tgccgggcca | 720 |
| ctgccgccaa | aactggcgca | acttaaagcg | gaactgaaaa | acgtacaaaa | tatctttttct | 780 |
| gtcgaacggc | tggattattc | caaaggtttg | ccagagcgtt | ttctcgccta | tgaagcgttg | 840 |
| ctggaaaaat | atccgcagca | tcatggtaaa | attcgttata | cccagattgc | accaacgtcg | 900 |
| cgtggtgatg | tgcaagccta | tcaggatatt | cgtcatcagc | tcgaaaatga | agctggacga | 960 |
| attaatggta | aatacgggca | attaggctgg | acgccgcttt | attatttgaa | tcagcatttt | 1020 |
| gaccgtaaat | tactgatgaa | aatattccgc | tactctgacg | tgggcttagt | gacgccactg | 1080 |

-continued

```
cgtgacggga tgaacctggt agcaaaagag tatgttgctg ctcaggaccc agccaatccg    1140
ggcgttcttg ttctttcgca atttgcggga gcggcaaacg agttaacgtc ggcgttaatt    1200
gttaacccct acgatcgtga cgaagttgca gctgcgctgg atcgtgcatt gactatgtcg    1260
ctggcggaac gtatttcccg tcatgcagaa atgctggacg ttatcgtgaa aaacgatatt    1320
aaccactggc aggagtgctt cattagcgac ctaaagcaga tagttccgcg aagcgcggaa    1380
agccagcagc gcgataaagt tgctaccttt ccaaagcttg cgtag                   1425
```

<210> SEQ ID NO 6
<211> LENGTH: 474
<212> TYPE: PRT
<213> ORGANISM: Escherichia coli

<400> SEQUENCE: 6

Met Ser Arg Leu Val Val Ser Asn Arg Ile Ala Pro Pro Asp Glu
1               5                   10                  15

His Ala Ala Ser Ala Gly Gly Leu Ala Val Gly Ile Leu Gly Ala Leu
            20                  25                  30

Lys Ala Ala Gly Gly Leu Trp Phe Gly Trp Ser Gly Glu Thr Gly Asn
        35                  40                  45

Glu Asp Gln Pro Leu Lys Lys Val Lys Lys Gly Asn Ile Thr Trp Ala
    50                  55                  60

Ser Phe Asn Leu Ser Glu Gln Asp Leu Asp Glu Tyr Tyr Asn Gln Phe
65                  70                  75                  80

Ser Asn Ala Val Leu Trp Pro Ala Phe His Tyr Arg Leu Asp Leu Val
                85                  90                  95

Gln Phe Gln Arg Pro Ala Trp Asp Gly Tyr Leu Arg Val Asn Ala Leu
            100                 105                 110

Leu Ala Asp Lys Leu Leu Pro Leu Leu Gln Asp Asp Asp Ile Ile Trp
        115                 120                 125

Ile His Asp Tyr His Leu Leu Pro Phe Ala His Glu Leu Arg Lys Arg
    130                 135                 140

Gly Val Asn Asn Arg Ile Gly Phe Phe Leu His Ile Pro Phe Pro Thr
145                 150                 155                 160

Pro Glu Ile Phe Asn Ala Leu Pro Thr Tyr Asp Thr Leu Leu Glu Gln
                165                 170                 175

Leu Cys Asp Tyr Asp Leu Leu Gly Phe Gln Thr Glu Asn Asp Arg Leu
            180                 185                 190

Ala Phe Leu Asp Cys Leu Ser Asn Leu Thr Arg Val Thr Thr Arg Ser
        195                 200                 205

Ala Lys Ser His Thr Ala Trp Gly Lys Ala Phe Arg Thr Glu Val Tyr
    210                 215                 220

Pro Ile Gly Ile Glu Pro Lys Glu Ile Ala Gln Ala Ala Gly Pro
225                 230                 235                 240

Leu Pro Pro Lys Leu Ala Gln Leu Lys Ala Glu Leu Lys Asn Val Gln
                245                 250                 255

Asn Ile Phe Ser Val Glu Arg Leu Asp Tyr Ser Lys Gly Leu Pro Glu
            260                 265                 270

Arg Phe Leu Ala Tyr Glu Ala Leu Leu Glu Lys Tyr Pro Gln His His
        275                 280                 285

Gly Lys Ile Arg Tyr Thr Gln Ile Ala Pro Thr Ser Arg Gly Asp Val
    290                 295                 300

Gln Ala Tyr Gln Asp Ile Arg His Gln Leu Glu Asn Glu Ala Gly Arg
305                 310                 315                 320

```
Ile Asn Gly Lys Tyr Gly Gln Leu Gly Trp Thr Pro Leu Tyr Tyr Leu
            325                 330                 335

Asn Gln His Phe Asp Arg Lys Leu Leu Met Lys Ile Phe Arg Tyr Ser
        340                 345                 350

Asp Val Gly Leu Val Thr Pro Leu Arg Asp Gly Met Asn Leu Val Ala
            355                 360                 365

Lys Glu Tyr Val Ala Ala Gln Asp Pro Ala Asn Pro Gly Val Leu Val
        370                 375                 380

Leu Ser Gln Phe Ala Gly Ala Ala Asn Glu Leu Thr Ser Ala Leu Ile
385                 390                 395                 400

Val Asn Pro Tyr Asp Arg Asp Glu Val Ala Ala Ala Leu Asp Arg Ala
            405                 410                 415

Leu Thr Met Ser Leu Ala Glu Arg Ile Ser Arg His Ala Glu Met Leu
                420                 425                 430

Asp Val Ile Val Lys Asn Asp Ile Asn His Trp Gln Glu Cys Phe Ile
            435                 440                 445

Ser Asp Leu Lys Gln Ile Val Pro Arg Ser Ala Glu Ser Gln Gln Arg
        450                 455                 460

Asp Lys Val Ala Thr Phe Pro Lys Leu Ala
465                 470

<210> SEQ ID NO 7
<211> LENGTH: 1338
<212> TYPE: DNA
<213> ORGANISM: Lactococcus lactis

<400> SEQUENCE: 7
atgaacaatt ttattcaaaa caaaatcatg cctccaatga tgaaattttt gaatacccgt      60
gcagtcacgg caatcaaaaa tggtatgatt tatcctatcc catttatcat tattggttca    120
gtattcttga ttcttggtca actgccattc caagcaggac aagacttcat gaacaaaatc    180
aaattgggcc cactcttttt acaaattaat aatgcttcat tggtattat ggctttgctt     240 gccgtgttcg gtattgctta cgcttgggtt cgagatgcag ttatgaagg agtacccgct     300 ggtttaacag gtgtcattgt tcacatcttg ttgcaaccaa cacaatcca tcaagtaaca     360 agtgttactg acccaactaa acatcaaca gcatttcaag taggtggtgt cattgaccga     420
gcttggttag gtgggaaagg gatggttctc tcaatcatcg ttggactctt agtaggttgg    480
atttacactg gctttatgcg tcggaacatc acaatcaaaa tgccagaaca agttccagaa    540
aacgttgccg catcatttac ttcacttgta cctgcaggag caatcattac aatggctggt    600
gtggttcatg gaatcacaac gattggcttc aacacaactt tcattgagtt agtttataaa    660
tggattcaaa caccattgca acacgtgact gacggtccgg ttggggtctt cgttattgcc    720
tttatgccag tatttatctg gtggttcggt gttcacggag cgacaatcat ggtgggatt    780 atgggaccat tgcttcaagc aaactctgct gacaatgctg ctctctacaa agcaggacat    840
cttagcctgt caaatggcgc ccatatcgtt actcaatcat ttatggacca atacttgaca    900
gttactggtt ctggttttgac cattggtttg gttatcttcc tcttagtgag tgcaaaatca    960
gttcaaggta aaactttagg acgaatggaa attggacctg cagtattcaa tatcaacgaa   1020
cctattctgt ttggacttcc tatcgttttg aatccaattc ttgctattcc attta tcttg    1080 gctccgttga tttcaggaat tttgacttac ttagtgattt atctaggaat cattccacca   1140
tttaatggtg cctatgttcc ttggacaacc cctgcggtct tgtcaggata tctagtaggt   1200
```

```
ggctggcaag gtatggtttg gcaaattatt attcttgctt tgaccacagt tctctattgg   1260
ccatttgcca aagcttatga caatattctt ctgaaagaag aagctgaaac agaagctgga   1320
attaatgctg ccgaataa                                                  1338
```

<210> SEQ ID NO 8
<211> LENGTH: 445
<212> TYPE: PRT
<213> ORGANISM: Lactococcus lactis

<400> SEQUENCE: 8

```
Met Asn Asn Phe Ile Gln Asn Lys Ile Met Pro Pro Met Met Lys Phe
1               5                   10                  15

Leu Asn Thr Arg Ala Val Thr Ala Ile Lys Asn Gly Met Ile Tyr Pro
            20                  25                  30

Ile Pro Phe Ile Ile Ile Gly Ser Val Phe Leu Ile Leu Gly Gln Leu
        35                  40                  45

Pro Phe Gln Ala Gly Gln Asp Phe Met Asn Lys Ile Lys Leu Gly Pro
    50                  55                  60

Leu Phe Leu Gln Ile Asn Asn Ala Ser Phe Gly Ile Met Ala Leu Leu
65                  70                  75                  80

Ala Val Phe Gly Ile Ala Tyr Ala Trp Val Arg Asp Ala Gly Tyr Glu
                85                  90                  95

Gly Val Pro Ala Gly Leu Thr Gly Val Ile Val His Ile Leu Leu Gln
            100                 105                 110

Pro Asp Thr Ile His Gln Val Thr Ser Val Thr Asp Pro Thr Lys Thr
        115                 120                 125

Ser Thr Ala Phe Gln Val Gly Gly Val Ile Asp Arg Ala Trp Leu Gly
    130                 135                 140

Gly Lys Gly Met Val Leu Ser Ile Ile Val Gly Leu Leu Val Gly Trp
145                 150                 155                 160

Ile Tyr Thr Gly Phe Met Arg Arg Asn Ile Thr Ile Lys Met Pro Glu
                165                 170                 175

Gln Val Pro Glu Asn Val Ala Ala Ser Phe Thr Ser Leu Val Pro Ala
            180                 185                 190

Gly Ala Ile Ile Thr Met Ala Gly Val Val His Gly Ile Thr Thr Ile
        195                 200                 205

Gly Phe Asn Thr Thr Phe Ile Glu Leu Val Tyr Lys Trp Ile Gln Thr
    210                 215                 220

Pro Leu Gln His Val Thr Asp Gly Pro Val Gly Val Phe Val Ile Ala
225                 230                 235                 240

Phe Met Pro Val Phe Ile Trp Trp Phe Gly Val His Gly Ala Thr Ile
                245                 250                 255

Ile Gly Gly Ile Met Gly Pro Leu Leu Gln Ala Asn Ser Ala Asp Asn
            260                 265                 270

Ala Ala Leu Tyr Lys Ala Gly His Leu Ser Leu Ser Asn Gly Ala His
        275                 280                 285

Ile Val Thr Gln Ser Phe Met Asp Gln Tyr Leu Thr Val Thr Gly Ser
    290                 295                 300

Gly Leu Thr Ile Gly Leu Val Ile Phe Leu Val Ser Ala Lys Ser
305                 310                 315                 320

Val Gln Gly Lys Thr Leu Gly Arg Met Glu Ile Gly Pro Ala Val Phe
                325                 330                 335

Asn Ile Asn Glu Pro Ile Leu Phe Gly Leu Pro Ile Val Leu Asn Pro
            340                 345                 350
```

```
Ile Leu Ala Ile Pro Phe Ile Leu Ala Pro Leu Ile Ser Gly Ile Leu
        355                 360                 365

Thr Tyr Leu Val Ile Tyr Leu Gly Ile Ile Pro Pro Phe Asn Gly Ala
        370                 375                 380

Tyr Val Pro Trp Thr Thr Pro Ala Val Leu Ser Gly Tyr Leu Val Gly
385                 390                 395                 400

Gly Trp Gln Gly Met Val Trp Gln Ile Ile Leu Ala Leu Thr Thr
                405                 410                 415

Val Leu Tyr Trp Pro Phe Ala Lys Ala Tyr Asp Asn Ile Leu Leu Lys
        420                 425                 430

Glu Glu Ala Glu Thr Glu Ala Gly Ile Asn Ala Ala Glu
        435                 440                 445

<210> SEQ ID NO 9
<211> LENGTH: 486
<212> TYPE: DNA
<213> ORGANISM: Lactococcus lactis

<400> SEQUENCE: 9
atgtttggaa taggaaaaaa gaaagaattg agagatgata aaagccttta tgctccagtt      60
tctggggaag ttatcaacct ttcaacagtc aacgaccccg tattttcaaa aaagataatg     120
ggagacgggt tcgcggttga gccaaaagaa aataaaattt tgccccagtt ttctgcaaaa     180
gtaactttgg ttcaaggaca tgcaattggt tttaaacgtg ctgatggctt agatgtactt     240
ttacatcttg gaattgatac agtagctctt aaaggtcttc attttaaaat caaggtcaaa     300
gttgatgata ttgtcaatgg tggtgatgag cttggaagcg ttgattgggc acagattgaa     360
gctgcaggtt tagataaaac gacaatggtt atctttacaa atacaaaaga taaactctct     420
gagttcaatg tcaattatgg accagctact tctggaagtg aacttggtaa ggcaagtgtt     480
aaataa                                                                486

<210> SEQ ID NO 10
<211> LENGTH: 161
<212> TYPE: PRT
<213> ORGANISM: Lactococcus lactis

<400> SEQUENCE: 10

Met Phe Gly Ile Gly Lys Lys Lys Glu Leu Arg Asp Asp Lys Ser Leu
1               5                   10                  15

Tyr Ala Pro Val Ser Gly Glu Val Ile Asn Leu Ser Thr Val Asn Asp
        20                  25                  30

Pro Val Phe Ser Lys Lys Ile Met Gly Asp Gly Phe Ala Val Glu Pro
        35                  40                  45

Lys Glu Asn Lys Ile Phe Ala Pro Val Ser Ala Lys Val Thr Leu Val
    50                  55                  60

Gln Gly His Ala Ile Gly Phe Lys Arg Ala Asp Gly Leu Asp Val Leu
65                  70                  75                  80

Leu His Leu Gly Ile Asp Thr Val Ala Leu Lys Gly Leu His Phe Lys
            85                  90                  95

Ile Lys Val Lys Val Asp Asp Ile Val Asn Gly Gly Asp Glu Leu Gly
            100                 105                 110

Ser Val Asp Trp Ala Gln Ile Glu Ala Ala Gly Leu Asp Lys Thr Thr
        115                 120                 125

Met Val Ile Phe Thr Asn Thr Lys Asp Lys Leu Ser Glu Phe Asn Val
        130                 135                 140
```

Asn Tyr Gly Pro Ala Thr Ser Gly Ser Glu Leu Gly Lys Ala Ser Val
145                 150                 155                 160

Lys

<210> SEQ ID NO 11
<211> LENGTH: 1566
<212> TYPE: DNA
<213> ORGANISM: Lactococcus lactis

<400> SEQUENCE: 11

```
atggcaaatt attcacaact tgcgacagaa attatcgcaa atgtaggtgg cgctgagaat      60
gtcacaaaag ttattcactg tatcactcgt cttcgtttta ccttgaaaga caaagataaa     120
gcagatacgg cggcgattga agccttacct ggtgtcgctg agctgtttta taactcaaac     180
ttgaatcaat atcaagtagt tattggacaa gctgtagaag atgtttatga cgaggttgtt     240
gaacagcttg gagattcagt tgttgatgaa atgcaacgg cgcaagcact tgctgcaaca     300
gcaccggcta gtggtaaaaa acaaaatcca attgttcatg ctttccaagt ggttattggg     360
acaattacag gttcgatgat tccaattatt ggtttacttg cggctggtgg atgattaat     420
ggattattaa gtatctttgt taaaggaaat cgtttaattg aagtgattga ccctgcaagt     480
tcaacttacg tcattatctc aactctagca atgacaccat tttatttctt acctgtttta     540
gtaggatttt cagcagcaaa acaattagca cctaaagata ctgttttaca atttattggt     600
gctgctgttg gtggtttcat gattaatcca gggattacta acttggtaaa tgctcatgtt     660
ggaacaaatg cggccggtaa aatgttgtt gttgaagcag cagctccagt agcaaatttc     720
cttggagtca cttttaatac aagttatttt ggaattccgg ttgctttgcc aagttatgct     780
tatacaattt tcccaatcat tgtggcggta gcaatcgcta aacctttgaa tgcttggttg     840
aaaaaggttt taccacttgc cttgcgtcca attttccaac cgatgattac tttcttcatc     900
actgcttcaa tcattttact cttggtcggt cctgttattt caacaatttc atctggtttg     960
tcattcgtta ttgaccatat cttgtcatta aacttaggga ttgcaagtat atcgtcggt    1020
ggtttgtatc aatgtttggt tatatttggt ttgcactggt tggttgtacc acttattcca    1080
caagagttgg cagcaacagg agcaagctca cttaatatga ttgttagctt cacaatgctt    1140
gcgcaaggag ttggtgcctt gactgtcttc tttaaatcta aaaagctga ccttaaagga    1200
ctttctgctc cagctgccat ttcggctttt tgtggagtaa ctgaacctgc catgtacgga    1260
attaacttga aatatgttcg cgtcttcatc atgtcttcaa ttggtgcagc aattggtgct    1320
gggattgccg gatttggtgg cttacaaatg tttggatttt cagggtcatt gattagtttt    1380
cctaacttta tctctaatcc attgacgcat catgcacctg cgggtaactt aatgctcttc    1440
tggattgcca ctgcggtatg tgctgttgcc actttcttat tagtttggtt ctttggttac    1500
aaggatactg atgtcatggg acaaggagtt gaacaaaaaa atgcatttaa ggatgctgta    1560
aaataa                                                               1566
```

<210> SEQ ID NO 12
<211> LENGTH: 521
<212> TYPE: PRT
<213> ORGANISM: Lactococcus lactis

<400> SEQUENCE: 12

Met Ala Asn Tyr Ser Gln Leu Ala Thr Glu Ile Ile Ala Asn Val Gly
1               5                   10                  15

```
Gly Ala Glu Asn Val Thr Lys Val Ile His Cys Ile Thr Arg Leu Arg
            20                  25                  30

Phe Thr Leu Lys Asp Lys Asp Lys Ala Asp Thr Ala Ala Ile Glu Ala
        35                  40                  45

Leu Pro Gly Val Ala Gly Ala Val Tyr Asn Ser Asn Leu Asn Gln Tyr
    50                  55                  60

Gln Val Val Ile Gly Gln Ala Val Glu Asp Val Tyr Asp Glu Val Val
65                  70                  75                  80

Glu Gln Leu Gly Asp Ser Val Val Asp Glu Asp Ala Thr Ala Gln Ala
                85                  90                  95

Leu Ala Ala Thr Ala Pro Ala Ser Gly Lys Lys Gln Asn Pro Ile Val
            100                 105                 110

His Ala Phe Gln Val Val Ile Gly Thr Ile Thr Gly Ser Met Ile Pro
        115                 120                 125

Ile Ile Gly Leu Leu Ala Ala Gly Gly Met Ile Asn Gly Leu Leu Ser
    130                 135                 140

Ile Phe Val Lys Gly Asn Arg Leu Ile Glu Val Ile Asp Pro Ala Ser
145                 150                 155                 160

Ser Thr Tyr Val Ile Ile Ser Thr Leu Ala Met Thr Pro Phe Tyr Phe
                165                 170                 175

Leu Pro Val Leu Val Gly Phe Ser Ala Ala Lys Gln Leu Ala Pro Lys
            180                 185                 190

Asp Thr Val Leu Gln Phe Ile Gly Ala Ala Val Gly Phe Met Ile
        195                 200                 205

Asn Pro Gly Ile Thr Asn Leu Val Asn Ala His Val Gly Thr Asn Ala
    210                 215                 220

Ala Gly Lys Asn Val Val Glu Ala Ala Pro Val Ala Asn Phe
225                 230                 235                 240

Leu Gly Val Thr Phe Asn Thr Ser Tyr Phe Gly Ile Pro Val Ala Leu
            245                 250                 255

Pro Ser Tyr Ala Tyr Thr Ile Phe Pro Ile Ile Val Ala Val Ala Ile
        260                 265                 270

Ala Lys Pro Leu Asn Ala Trp Leu Lys Lys Val Leu Pro Leu Ala Leu
    275                 280                 285

Arg Pro Ile Phe Gln Pro Met Ile Thr Phe Phe Ile Thr Ala Ser Ile
290                 295                 300

Ile Leu Leu Leu Val Gly Pro Val Ile Ser Thr Ile Ser Ser Gly Leu
305                 310                 315                 320

Ser Phe Val Ile Asp His Ile Leu Ser Leu Asn Leu Gly Ile Ala Ser
            325                 330                 335

Ile Ile Val Gly Gly Leu Tyr Gln Cys Leu Val Ile Phe Gly Leu His
        340                 345                 350

Trp Leu Val Val Pro Leu Ile Ser Gln Glu Leu Ala Ala Thr Gly Ala
    355                 360                 365

Ser Ser Leu Asn Met Ile Val Ser Phe Thr Met Leu Ala Gln Gly Val
370                 375                 380

Gly Ala Leu Thr Val Phe Phe Lys Ser Lys Lys Ala Asp Leu Lys Gly
385                 390                 395                 400

Leu Ser Ala Pro Ala Ala Ile Ser Ala Phe Cys Gly Val Thr Glu Pro
            405                 410                 415

Ala Met Tyr Gly Ile Asn Leu Lys Tyr Val Arg Val Phe Ile Met Ser
        420                 425                 430

Ser Ile Gly Ala Ala Ile Gly Ala Gly Ile Ala Gly Phe Gly Gly Leu
```

```
                           435                 440                 445
Gln Met Phe Gly Phe Ser Gly Ser Leu Ile Ser Phe Pro Asn Phe Ile
    450                 455                 460

Ser Asn Pro Leu Thr His His Ala Pro Ala Gly Asn Leu Met Leu Phe
465                 470                 475                 480

Trp Ile Ala Thr Ala Val Cys Ala Val Ala Thr Phe Leu Leu Val Trp
                485                 490                 495

Phe Phe Gly Tyr Lys Asp Thr Asp Val Met Gly Gln Gly Val Glu Gln
                500                 505                 510

Lys Asn Ala Phe Lys Asp Ala Val Lys
                515                 520

<210> SEQ ID NO 13
<211> LENGTH: 107
<212> TYPE: DNA
<213> ORGANISM: Lactococcus lactis

<400> SEQUENCE: 13
aaaacgcctt aaaatggcat tttgacttgc aaactgggct aagatttgct aaaatgaaaa        60
atgcctatgt ttaaggtaaa aaacaaatgg aggcatttc taaaatg                     107
```